(12) United States Patent
Elton et al.

(10) Patent No.: US 7,718,789 B2
(45) Date of Patent: May 18, 2010

(54) COMPOSITIONS AND METHODS FOR THE MODIFICATION OF GENE EXPRESSION

(76) Inventors: Clare K. Elton, 149 Beach Haven Road, Beach Haven, Auckland (NZ); Claire Hall, 3-253 Kepa Road, Mission Bay, Auckland (NZ); Jeroen Demmer, 33B Glenvar Road, Torbay, Auckland (NZ)

(*) Notice: Subject to any disclaimer, the term of this patent is extended or adjusted under 35 U.S.C. 154(b) by 354 days.

(21) Appl. No.: 11/138,987

(22) Filed: May 25, 2005

(65) Prior Publication Data

US 2005/0278800 A1    Dec. 15, 2005

Related U.S. Application Data

(60) Provisional application No. 60/580,007, filed on Jun. 15, 2004.

(51) Int. Cl.
C07H 19/073    (2006.01)
C07H 21/02     (2006.01)
C12N 15/82     (2006.01)
C12N 15/63     (2006.01)

(52) U.S. Cl. .............. 536/24.1; 536/23.1; 800/278; 800/287; 800/295; 435/320.1; 435/410; 435/468

(58) Field of Classification Search .............. None
See application file for complete search history.

(56) References Cited

OTHER PUBLICATIONS

GenBank Accession: AP004115 GI:15375101, Mar. 21, 2002, pp. 1-32.*
Kim et al 1994, Plant Molecular Biology 24:105-117.*
Dolferus et al 1994, Plant Physiology 105:1075-1087.*

* cited by examiner

*Primary Examiner*—Anne Marie Grunberg
*Assistant Examiner*—Brent Page
(74) *Attorney, Agent, or Firm*—Janet Sleath; Speckman Law Group PLLC

(57) ABSTRACT

Novel isolated plant polynucleotide promoter sequences are provided, together with genetic constructs comprising such polynucleotides. Methods for using such constructs in modulating the transcription of DNA sequences of interest are also disclosed, together with transgenic plants comprising such constructs.

19 Claims, 32 Drawing Sheets

```
        I                       XII                     II
      ┌────┐                  ┌─────┐                 ┌──────┐
      AAAGTGTCCATCTACTAAAACAGTTGTGGAGGACATATCAAATAATTTATTCCCGTGAGT

TGTACATATCAGTAAACATGAAATTAAGGACTTGTTAAGGTGGGATTAAACTAGCAGTTT
          IV                              XXIX              I,XIV
      TAATATTCATTATTCAAATATAGGCGTTCCACACTGTTGTTAGGTCCAAAGAAATAACTT
        I   VIII              XXXIII
      CGAAAG GATATCTTCGATGCCCTTTTGTGTCTAGAATCCTTGCATTTTCCTTTCACGCGT
               XVI               XI           XLV
      GTGTTGGATCAACATTTCATGAGTTTATTTAGCGTAATTTTTGGTTCTTCTAAACATACC
          XXI      XLVI    XXXI      XI
      CGGTACACATAAACATAACGTT CACGTG TTATTTTGTACTCGCTTCGATCCATAATAAGT
                    I                                   XVI
      ATCGGAAACTTAGTACAAAAGTTGTACTTACTAGTACAAAATTCTCAACATTTTTTATAG
                                        XVI
      ATCGGAGGGAGGGAGTAGTAGTTTTCAAACAACATGATTCCAACTCTCAAAACATGGCTT
                V                    XLVII
      TTTTGTGAGGTACACAATTTTACAAACTCTAATTCAAATCTTTGCTAGAGAATACCTGTC
        IX                                       XVII
      GAAAAAGTAGAAGGTCTTAATTGTTTGTTATTCCATGCCAACCATTTTCTCTCTTTCCAT
                    XIV,IX    XLIII,XI     I,XIV,IX
      TTCCCACCAAAACTGACAGAAAAATACTTTATTTTTCCCAAAGAAAATCACGAGAGGGCT
          I
      GAGTAAAAAAAAGATGTCCATATAAAACAGGGCACAAGGCCAAGGCTAGCGCTTGGTTCT
                                                XLVIII
      CCTGCCTCTTGCCTTAGTTCGCCACCACCGCCGCCACCTACCCCCTCATCCTTTCTCCTC

CCCCGCTCTCGCAGCGTCCGCTCATCTCGGTGAGAGGTCTTCAGGCGAGCAGGTTCCCCT

ACATCCCCCGAGTCACTTAAT
```

Figure 1

```
                XXXIII
ATCTTCGATGC CCTTTT GTGTCTAGAATCCTTGCATTTTCCTTTCACGCGTGTGTTGGAT
    XVI              XI         XLV
 CAACA TTTCATGAGT TTATTT AGCGTA ATTTTTG GTTCTTCTAAACATACCCGGTACACA
          XLVI    XXXI    XI
TAAACAT AACGTT  CACGTG  TTATTT TGTACTCGCTTCGATCCATAATAAGTATCGGAAAC
         I                              XVI
TTAGTACA AAAG TTGTACTTACTAGTACAAAATTCT CAACA TTTTTTATAGATCGGAGGG
                          XVI
AGGGAGTAGTAGTTTTCAAA CAACA TGATTCCAACTCTCAAAACATGGCTTTTTTGTGAG
      V              XLVII                              IX
GTACA CAAT TTTACAAACTCT AATTCAAA TCTTTGCTAGAGAATACCTGTC GAAAAA GTA
                                   XVII
GAAGGTCTTAATTGTTTGTTATTCCATG CCAACC ATTTTCTCTCTTTCCATTTCCCACCA
           XIV,IX  XLIII,XI       I,XIV,IX
AAACTGAC AGAAA AAT ACTTTA TTTTTCCC AAAG AAAA TCACGAGAGGGCTGAGTAAAAA
   I
 AAAG ATGTCCATATAAAACAGGGCACAAGGCCAAGGCTAGCGCTTGGTTCTCCTGCCTCT
                            XLVIII
TGCCTTAGTTCGCCACCACCGCCGC CACCTACC CCCTCATCCTTTCTCCTCCCCGCTCT

CGCAGCGTCCGCTCATCTCGGTGAGAGGTCTTCAGGCGAGCAGGTTCCCCTACATCCCCC

GAGTCACTTAAT
```

Figure 2

```
        XI              XLV                                    XXI
AGT TTATTT AGCTA ATTTTTG GTTCTTCTAAACATACCCGG TACACAT AAACATAACGT
    XXXI    XI                                                       I
T CACGTG  TTATTT TGTACTCGCTTCGATCCATAATAAGTATCGGAAACTTAGTA AAAG TT
                            XVI
GTACTTACTAGTACAAAATCCT CAACA TTTTTTATAGATCGGAGGGAGGGAGTAGTAGTT
      XVI                                              V
TTCAAA CAACA TGATTCCAACTCTCAAAACATGGCTTTTTTGTGAGGTACA CAAT TTTAC
         XLVII                          IX       XXX
AAACTCT AATTCAAA TCTTTGCTAGAGAATACCTGTC GAAAAA  ATAGAA GGTCTTAATTG
              XVII                                                XIV
TTTGTTATTCCATG CCAACC ATTTTCTCTCTTTCCATTTCCCACCAAAACTGAC AGAAA A
    XLIII,XI      I,XIV,IX                      I
AT ACTTTA TTTTTCCC AAAG AAAAT CACGAGAGGGCTGAGTA AAAG ATGTCCATATAAAA

CAGGGCACAAGGCCAAGGCTAGCGCTTGGTTCTCCTGCCTCTTGCCTTAGTTCGCCACCA

CCGCCGCCACCCACCCCCTCATCCTTTCTCCTCCCCGCTCTCGCAGCGTCCGCTCATCT

CGGTGAGAGGTCTTCAGGCGAGCAGGTTCCCCTACATCCCCCGAGTCACTTAAT
```

Figure 3

```
                                                    VIII,IV
AAAAATGTCAAAAAATTCTGAAACAAAATTTCTGGTGTACATCAT GATA TTCTATGTTCG
                  IX      XVI                         I
TACACAAATTTCGTG GGAAAA   CAACA TTTTATGTGGCATGTACAAA AAAG ACAAAAAAAT
       XXXV                                     III
ATCATG TACGTA GTCGTGTTGGAGCATAAAAAATTGTCTTTTTT ACACGGG ACACAAAAA
    IV,XI      VII                         XXX              VI
AA ATATT ATTTTTC CCGAAA ACTTGTGCACGAAC ATAGAA TGTCTAGATGTA CATGTG CA
   XI,XLVII     VIII,IV                      III           XXII
ATT TTATTT CAAATTTTTTT GATA TTTTGAAATATGTTTTCAC ACACTGG GTT CATATG
              VII   II
CACCCATGAG CCGAAA TAAATATCCTGTTTGTTTAAGTCAAACTACTCTAGGTTTCATC
                                                              IV
AGGTTTATAAAAAAAACATCACCAACTTAGTTTCATTAGATTCATCATAACATT ATATT A
                                    XIV,IX              XXX,XIV
ACATAATTTCTTATAAACTCGATCGAACTT AGAAA AAATATGTTAATATAT ATAGAA AAC
   V   XI
CT CAAT TATTTTGGAACCGTTTCCCTTCGTGACTTTTGTTTTCGATTTTTTTTCTTGAA
            XXXIV                               XXXI
ACGTGACTGCCATAGG TAACTG ACCGGAACGGCGGGAAGCATTGGCCGGCT CACGTG AAT
            I                                              XIV
CGTGTCCACGGAGCATTGGCCCACGTA AAAG CAACCGCTCCTCACCGCCGCACCC AGAAA
                                                         XXXIII
CTACCCCGATCTCTCATCCCCTTCTCCCCCTCTCTCCTCCGCCCTGCCC CCTTTT ATC
                     XIV
TCCCGATCTCACACGTTTTGGGAAGAGAG AGAAA GAGAGCGGTTTCGAGAGGGCCATTCT

TCGTACCCAAGGAGAGATCCA
```

Figure 4

```
          I
CTGAAAGCGAAGTAATTGTGAAGAGAGGGAGTACAAACTAGTAATACGCATACCAACTTA
            I                        XIV                     XXXIII
GCTCATACAAAAAGGTTGTTGTTGGCCAGGAGAAACTATGGAAGTTTGTTCCTTTTAAAA
                  XXI  XV
AGGCACTTTTTTACGTGTACACATTTGAGTTTCGTTCGTCGAAGACCAAGTAAAAATGGG
       XIV                                    XV
CGAACAGAAACGGCGACTTTGAGAGTTGAGACATGGTTGTCAAATGGAACGATCACCGTA
              XVI                                        I
GACCACAAAATCAACAAATTTGAACCCCAAAATACGAGGAAGTCTAGCATGAAAGTTGTA
XVII                           VIII
CCAACCGCTGCTATTTCCGTCTCCTTCACCAGATATGGAATACAGCCCTGCCGCTGGTGA
  XII                                           XV       V
CACATGTATCTGAGCAGGTTTGGGCATGACCTGGGACATGGATGTCAAATGGAACAATC
                    XVI, LX   XXV
ACCGTAGACCACTAAATATCAACAAACTTGACCCCCAAAATACCAGGAAGCCTAATATAT
       I        XVII              XXIV          XVI
AACATGAAAGTTGTACCAACCTCTGCTATTTCTGTCTCCTTCACCTGAGATGGTGTAATG
                          XII      XI      IX      XIV
CAAAATACAGCCTTGAATGTGGTGACACATGTTTTATTTTCGAAAAAAGAAAAGGTGACA

GATGTATCTGAAGCAGGTTTGGGCATGACTTTTTGCAGCCTGAGAAGCAACCATCGTCAC
                       XVIII  V
CAACCCCGGCGCACGAATGACCGACCAATGCGGGGAGGATTCTGTCGAACGGCTGGCCAA
             XXVI
GCCAAGCTGCCGCTTTTTTTTTTTTTTTTGCGAAGGAAGCCAAGCTGCCGCTGATCATG
      IX       XIX
GAGTAGGTAAACGAGGTCGACGTGGCACCCCTGCCCCAGTCAACGAACCCCAGCCATTC
      XXIV      XVII   XX                    XXIII      XIII
TCTCCCTGTCTCGCCAACCCTCCCACTCTGACTGCCATGTTGGTCCACACGTCATCCTC
                            XVIII      IV    III
TCAGGCCCCACTCACCAACTCCCCGACTCCTTCCCCCGTATATT ACACCCGCCATCTTCC

GTTCCTCCCTTCTTCTTCAGGAGATCAAGTAAGCACGCGCACGCAGTCGCACAAGCCATC
  XVIII,XIX
TCCGACGACTAATTTAACCACCTTAGAAGATTTAGTCTCCGTTTCTCTCTCGATCGC
```

Figure 5

```
     I                     XXI,XV
AA AAAG GCACTTTTTTTACGTG TACACAT TTGAGTTTCGTTCGTCGAAGACCAAGTAAAAA
          XIV                                    XV
TGGGCGAAC AGAAA CGGCGACTTTGAGAGTTGAGACATGGTTGT CAAATG GAACGATCAC
                  XVI                                    I
CGTAGACCACAAAAT CAACA AATTTGAACCCCAAAATACGAGGAAGTCTAGCATG AAAG T
          XVII                          VIII
TGTA CCAACC GCTGCTATTTCCGTCTCCTTCACCA GATA TGGAATACAGCCCTGCCGCTG
     XII                                              XV
GTG ACACATG TATCTGAGCAGGTTTTGGGCATGACCTGGGACATGGATGT CAAATG GAAC
              XVI,LX    XXV
AATCACCGTAGACCACTAAATAT CAACA AAC TTGACC CCCAAAATACCAGGAAGCCTAAT
     I        XVII              XXIV         XVI
ATATAACATG AAAG TTGTA CCAACC TCTGCTATTTC TGTCTC CTT CACCTG AGATGGTGT
   XXII                     XII         XI      IX      XIV
AA TGCAAAAT ACAGCCTTGAATGTGGTG ACACATG TT TTATTT TC GAAAAA AGAAA AGGT
    XII
GA CAGATG TATCTGAAGCAGGTTTGGGCATGACTTTTTGCAGCCTGAGAAGCAACCATCG
       XVII                XVIII   V
TCA CCAACC CCGGCGCACGAATGA CCGAC CAAT GCGGGGAGGATTCTGTCGAACGGCTGG
                                XXVI
CCAAGCCAAGCTGCCGC TTTTTTTTTT TTTTTTTGCAAGGAAGCCAAGCTGCCGCTGAT
            IX      XIX
CATGGAGTA GGTAAA CGAGGT CGACG TGGCACCCCTGCCCCAGTCAACGAACCCCAGCC
          XXIV   XVII         XX                  XXIII     XIII
ATTCTCTCC TGTCTC G CCAACC CTCCCAC TCTGACTGCCATGT TGGTCCCAC ACGTCA T
                           XVIII      IV      III
CCTCTCAGGCCCCACTCACCAACTCC CCGAC TCCTTCCCCGT ATATT ACACCCG CCATC

TTCCGTTCCTCCCTTCTTCTTCAGGAGATCAAGTAAGCACGCGCACGCAGTCGCACAAGC
         XVIII,XIX
CATCT CCGAC GACTAATTTAACCACCTTAGAAGATTTAGTCTCCGTTTCTCTCTCGATCG

```
CCTGGAGTGAATCCAGGAAGTGTTAGTGCCATTAGTTAGTGGAGTAGTGGGTCAGAGAGT
                                                    IV
GGCGTGAGTTGCGTGGCAGAGAAGTGCCTAAACTTGTATAT|ATATT|CTGCATTGAGTTAA
        VIII        X             XIV
TGAGAA|GATA|GCCCG|TGACG|GCTGAAG|AGAAA|AGATGTAGCCTCTCTCGTACACCATGGA
           I              XI
TAGAATTCCTCTTGGC|AAAG|CCATGG|TTATTT|CTCCATGGTGTGTGCGCGTGTGTCTTCT
                            VI
TTCTTGAGTTTTCCTGATCTTTCTCAC|CATGTG|TGTGTTCTTGTGAGGTGAGAGAGACAA

GAGAGATTGTGAGAGATCAGAGGTAGAAGAAGAAGATGGGGCTTCGAGATGCAGCCCCCA

ACACCCCGCCCTCGAAGAAGGAACCCTTGAGAGTGCTCGCCGCCTGCCACCTCGCGATCG
                                      V       IX       XI
CTCTGATGACCATCGCGGGCTGGCCTCTCTCCG|CAAT|ACA|GGTAAA|A|TTATTT|CATTCAG
    II              VII    XLV
AA|AATAAT|TGTACCATTAA|CCGAAA|TTTTTGTGCCATAACCGGCTGTAGCTATAGTCGGC
                    I
CGATCCCCGGAGTTCGCCAGGACAA|AAAG|GAGTAGGTAGTGTGTGTGGTAGGTGAAGGGA
  I                                       V      III,XVI
G|AAAG|CCCCATATATATAGCCCCTTCTCACCCTCCCT|CCAAT|GT|ACACCTG|ATCGCTCGG
                                          III
GTCTCTCGCTCATACTACCAAAAACACCCAGCAGC|ACACCAG|CGTCTCTCGGCCCAGGAG
         III
AAGCAG|ACACAGG|CAGAGAT
```

Figure 7

```
                           II                  IX
AAATGAGATCTAGTTTGATCATG AATTAAA AGTGGTCT GAAAAT AGACTTAAATTCTGTT
              XLIV,IX                   IV, XI
AAACTTCTAATATAT ATGGTA AATGCACGGCGTTCATACC ATATT AATACTTTCATAATT
         XV,VIII
TGTTTTTT CATCTG ATACTTAGTTTAGAAGCAAATTTATTCGAATCCTCTTCTTTCACCA
                            V
GTTCTTCCCAGTCCCCACTA CCAAT CTTAGAAGTATCTTTGCATCTTAATCCTCTCCTTT
                      II        IX
CTGATGCCCCGGAAACA AATTAAA AT GGAAAT ATATATGCGGCGCTGCACGCCATCACCG
LIV,   XXIV            XIV,IX                      LII,XLVIII
 TACGTGTCTC AACCTAATCT AGAAA ATCTCCCATCCTCCTCACGA CCTCACCTACC CCTC
          III                                       XL
CAACTATATAT ACACCAG CACCCTCCACCTTTGTCCTCAGCTCTACTC CAAGAGCATC AA
      XXXIX      LIII         XIV,IX
TCTAA AACCCA CGCGAT CGAACAC CCCT AGAAA AAAAAAC
```

Figure 8

```
                                     XXXIII              X       XVI
CCTCTTCTCCACTAGTGAATGGGTGGGTCCCTTTTCTACTAGTGTGACGCACCTGGCGCA
                 XLI,VIII,XXXVI           XVI
GGATCGAGAAGGATCCGAGGAGGATAGCGGGCTTCCTCGGCAACAGGAACTTCCCTTTGG
                                                   VIII
ACCATCCACCGCCGCCTCGTCATCGAAATGCGTCGCCCCGCTGGGAGATACCCTAAATCT

AGATGCTACATGCCCCATACCCCACGTTACTTAGTGCACCAGCGAACAAGGACAGAACAA
                             XXXIX
CCGGTCTTTCTGTATTCATCAACCCATACGGACAAAATCAGACACCACAGCCGCGTTGGA
         XIII           III                XXXVIII
GTTTCCCTTACGTCACACACACACCAGGGACGTGAGTTCTGTGGTTTGTTATCGGTAG
                                V
CTGTAATCCAGTTCCCTCTCTGAATCAATACATATCGGAGTAGCACACATTTTTTGTTG
        IV                              VIII
AAATATATTAGTGCTGGGCTACGTGCTACGATCGATCGATATAGCTGGGTAGACTTCTCG
                 XIV       XII
AAGGTTATACTCGGGCAGCAGAAATCACACATGCATGCCGTGCGTGTAGCATTGATGTAT
                         I        XL
CTAGACTGCGTGACTGGTTGTTCCTAAAGATCCAAGAGGATCCATAAGGTCGACATAGGG
              XV
CGGGAGCGCATCCAAGCAGCTGGGCAGGCCCAAGGCCAAGCGAGCCAACTAACTCCCATT

CGGCCGGATTGGTTGGTAGACGTGTCGCACGCGCCACCCATCCCCTCCCTCCGCAGGCGT
            XXXVII,XV
GGCCTTCCATCCTCCCGTCCAACTGACCTAACCCCTCACCCCGCGGCCGGCTCTCCTTCA
                                          XII
ACCACCCTTCCCGCCTATATATCTCGTCCGCGCACACATGGCACCACACCACAGCAGTAC
    XVI         XV              XV
TACAACAAGGAGCAACTGTCACTCATTCATCTGTCGTCTCCTGCTTCCCTCAAGCTTAGA

TCGATTGCAGC
```

Figure 9

```
XXXVI              XVI
AGCGGGCTTCCTCGGCAACAGGAACTTCCCTTTGGACCATCCACCGCCGCCTCGTCATCG
                       VIII
AAATGCGTCGCCCCGCTGGGAGATACCCTAAATCTAGATGTTACATGCCCCATACCCCAC

GTTACTTAGTGCACCAGCGAACAAGGACAGAACAACCGGTCTTTCTGTATTCATCAACCC
                                                  XIII
ATACGGACAAAATCAGACACCACAGCCGCGTTGGAGTTTCCCTTACGTCACACACACACA
                 XXXVIII
CCAGGGACGTGAGTTCTGTGGTTTGTTATCGGTAGCTGTAATCCAGTTCCCTCTCTGAAT
 V                                         IV
CAATACATATCGGAGTAGCACACATTTTTTGTTGAAATATATTAGTGCTGGGCTACGTG
         VIII                                        XIV
CTACGATCGATCGATATAGCTGGGTAGACTTCTCGAAGGTTATACTCGGGCAGCAGAAAT
     XII
CACACATGCATGCCGTGCGTGTAGCATTGATGTATCTAGACTGCGTGACTGGTTGTTCCT
 I         XL                                          XV
AAAGATCCAAGAGGATCCATAAGGTCGACATAGGGCGGGAGCGCATCCAAGCAGCTGGGC

AGGCCCAAGGCCAAGCGAGCCAACTAACTCCCATTCGGCCGGATTGGTTGGTAGACGTGT
                                                XXXVII,XV
CGCACGCGCCACCCATCCCCTCCCTCCGCAGGCGTGGCCTTCCATCCTCCGTCCAACTG

ACCTAACCCCTCACCCCGCGGCCGGCTCTCCTTCAACCACCCTTCCCGCCTATATATCTC
         XII                            XVI       XV
GTCCGCGCACACATGGCACCACACCACAGCAGTACTACAACAAGGAGCAACTGTCACTCA
       XV
TTCATCTGTCGTCTCCTGCTTCCCTCAAGCTTAGATCGATTGCAGC
```

Figure 10

```
ACCCTAAATCTAGATGTTACATGCCCCATACCCCACGTTACTTAGTGCACCAGCGAACAA
                                XXXIX
GGACAGAACAACCGGTCTTTCTGTATTCATCAACCCATACGGACAAAATCAGACACCACA
                 XIII           III              XXXVIII
GCCGCGTTGGAGTTTCCCTTACGTCACACACACACCAGGGACGTGAGTTCTGTGGTTT
                                  V
GTTATCGGTAGCTGTAATCCAGTTCCCTCTCTGAATCAATACATATCGGAGTAGCACACA
         IV                                VIII
TTTTTTTGTTGAAATATATTAGTGCTGGGCTACGTGCTACGATCGATATAGCTGGG
                           XIV     XII
TAGACTTCTCGAAGGTTATACTCGGGCAGCAGAAATCACACATGCATGCCGTGCGTGTAG
                                I        XL
CATTGATGTATCTAGACTGCGTGACTGGTTGTTCCTAAAGATCCAAGAGGATCCATAAGG
                   XV
TCGACATAGGGCGGGAGCGCATCCAAGCAGCTGGGCAGGCCCAAGGCCAAGCGAGCCAAC

TAACTCCCATTCGGCCGGATTGGTTGGTAGACGTGTCGCACGCGCCACCCATCCCCTCCC
                              XXXVII,XV
TCCGCAGGCGTGGCCTTCCATCCTCCCGTCCAACTGACCTAACCCCTCACCCCGCGGCCG
                                                   XII
GCTCTCCTTCAACCACCCTTCCCGCCTATATATCTCGTCCGCGCACACATGGCACCACAC
         XVI          XV              XV
CACAGCAGTACTACAACAAGGAGCAACTGTCACTCATTCATCTGTCGTCTCCTGCTTCCC

TCAAGCTTAGATCGATTGCAGC
```

Figure 11

```
                                                                  XIV,IX
AAATTATGTAAATAGCGGTATTTTTTTTGCGGTATTATTGACATACCATTCG|AGAAA|AAA
        XXV                      I              V
AAAC|TTGACC|CAGATTACATACA|AAAG|AGGGAC|CCAAT|TCATTATTCTCCTGTGTAGGCG
                      XXVII                        I      V
AAGCAGTTTCCCTGCCACTAAGAC|AACGTGT|TGTGTACTCTAC|AAAG| |CAAT|TTAGCTTG
    IX          XIV,IX                    XXIX      IV
AC|GGAAAA|CGTACCT|AGAAA|AACATCGAGGTGATCAAGA|CTGTTG|C|ATATT|CGCTCTCGG
                          XV          XV
CCTCTCCTGCGCCGCCCGTA|CAAGTG|CACTAG|CATTTG|CCCCTTTCCTAGACGAGCTAGC
         XV,XXV                              XXVIII
AAACAGGAATAGGC|CATTTG|ACCCACCCACTCCCCCTTTCC|CAAACAC|GTCTCTTCTCTT

CTCTCTTCGTCATCACCACCAGCACGCGCGCGCGCGAGTAGTAGTAGTAGCCCTCCAG

AGAGTCCACCAGACAGAGAGTAA
```

Figure 12

```
CCTTGATGGAGGATGCTTGGCTCTTGGATGTTTCTGGAGAGTTGTCCATTGATGGGTGGA
        V                                                IX
TG CAAT GCACCCTACTTTGGGAAGAGTTGGGGAGAGTGCCTCGTGAT GAAAAT AGGCCGG
        III    I                                              XVI
ATCAAAT CACTTG GAAAG GATCGGCGTCTAGGCGGTACTCCACCAGGGAGACTTA CAACA
                                V
TGCTTTGCATGGGGAGGATTACTTGGAGTATGGCCAAGC CAAT TTGAAGATCCTTTGCAC
    XV      XXII      XII      L,VIII,I                    XLIX,XLI
CTCT CAAGTG CAAAATCTT CAGATG GTTGGC GATAA AGCGCCGGCTATAGACTT CGGATA
                                VI    XII
GGAGGGCTAGGCATGGCCTACAGGCCTGACC CATGTG CACATG CCTTCAGGAGGAGGAT
                IV
AATGTTGATC ATATT CTGGCACAGTGCCCATACACCAAGATGGTCTGGTTCGGCTGTCTG

AGAAGAATGGGATCGCAGCTACAGGAGCCGCAGGAGAACACAAATTTGGAGAGATGGTGG
                         IX
ATGGAAGCGA GGAAAA GGCTGCGTAGGGAGGACAAGAGAGGCTTCGACACATTCGTTTG
                   I                                  XLI,VIII
TTGATCGCCTGGACGCTTTGGAAGC AAAG GAACGCCCGGGTGTTTGGGAACTT GGATA GA
                   VIII
CAACTCTCCACGGCGCAGATCATT GATA CAGTCCTCGAGGAGTTTAGCCTTTGGTGGGCT

GCGAGGGGAGGAGAGCGGCGAGTGATGCTGCGAGAGTAGGCGTGAGTCCTGGGTGTGTGC
                    XII
GTGGGTTGGCCAAGGG CAGATG TTCGCATCCCCCTCTGGTTTCTTGTAATTGTTGTTGCT
         I                          IX             V
CCCTTCTAT AAAG ATTCGGCACGCTTTTCGCGTGCCCGC GAAAAA GAATAT CAAT AGGGT
    LI    LXVII                           IV           XLIII
CCC TACTATT AACAG ATTTCTCCCAGATTTTAGATTAGT ATATT TGAAATT ACTTTA AAA
                     II    V                   V
CAGTATGAACTTTCAAAA AATAAT  CAAT ACAAAAATGTTTCA CAAT TTCTGTAGATTACT
              XXIX,XXX
GCACTACAAC CGGTTA TAGAA TACCCCGGCTATATATATATATCTATTTATAAGTACT
           II                 V
AGCAAGAGCA AATTAAA GTCTGACTTTGATGA CAAT TCGCACGCCGCATTATTGGACTGG
    IX                                   XXIX           XIII
TCACGG GGAAAT GACAACGCAGCCAAGAGCCAAGCGTGT CGGTTA CACAGCTCG CCGTCG
       XLI,VIII                            II                I
TCTCTCTA GGATA GATTCATCGTCCGTGTGACCGTGTCTGCAT AATAAA ATCTCC AAAG
VIII,IV                V
 GATA TTTTGTGTCCTCATACTG CAAT GTGGCCTCTCTTATCTAATTACCTATCCAGCTCA
    XIII                                                  XIX
CCT CCGAC CCTATATGGACTAGAATTGGTCCATGCCAGCCACGGATTTCAGT CGACG CAC
    XVI                             XII
AA CAACA AAAACGAAGGTTGAATTGGGAGG CAGTTG TGGGCCACAAACTAGCTAGTACTG
                  XXVIII
AGCCCCTTGCAACCTCGCATGCTTA CAAACAC ACAGAGGACACTATAAGATGGGATGCAC
          XVI     III     III          XLII     I
ATGCACCACCCAGA CAACA  ACACTTG CGAGT CACTTG CAT TGCAGG  AAAG GTTTCT
```

Figure 13

```
            XLV                             XXX         XLI,VIII
ATC ATTTTTA ACAAATTCCAAACAGTGCGA ATAGAA TTCTATTG GGATA CTATCAGTTCC
               XXIX                       IV    XIV,IX
AGGAGATTTTTTCT CCGTTG CAAATAAGGCAAATTTCACCTC ATATT C AGAAA AGGTTT

TATCATATCACTATTATCTTCCTCATTAAGCTTTTCATTAGGACTCCATAAGTTTTGGTC
     IX,IX                      XL
AATAC GGAAAA AATTGCCATGGGCAGGAC CAAAAAGATC TTTATAATACTTCAGTAGCAT
   XXV                    V     VIII
GA TTGACC GAGTTGTATGCCCCTTCCA CAAT  GATA CCATTATTATCCAAGGAGAGTCCTC
        V        I
CCATTAG CAAT TATATG AAAG TAAGCAGTATTTTGATCCTCTTCTAACAACCATTTCCAT
      XXXIII   V                        I       V
GGG CCTTTT GATGG CAAT AACTTTCCTCCTCCTCAT AAAG TTTAAA CAAT TCTTCCTGCA
                         XV                           IX
TCTTAACTCTGTAAGACATTT CATCTG TAGTTAACTTCCCATTCTCCTCT GGAAAT TCCA
        I                                        I
GCACCA AAAG CTCCTTCTTGAGCTCTAACTTCCTCTTTTTATTACTACC AAAG TACCAAA
             XVII            XI              VIII,IV
AGTATTTGCACC CCAACC TTTACCATACT TATTAAT CCTCACTATCTT GATA TTAAGAAT
    V   LI                          IV           XLIII
GT CAAT ACTATTAACAGGTTTCTCCTAGATTTTAGATTAGT ATATT TGAGATT ACTTTA A
     XI          II         V                    V
AACTG TATAAAT TTCAAAA AATAAT  CAAT ACAAAAATGTTTCA CAAT TTCTGTAGCTATC
                    V                    IX            IX
CAACGGTATATCATTTTCT CAAT TCCGATTAGCTATT GAAAAA CCGTAGT GAAAAA ACAG
     VIII       XXXVI, IX
TA GATA TAAGTACTAT AGCGGG AAATTCAAGAGTTTAAGGAAGTACATGGGAAGTTCATC
      I                 XXIX                           XXIX
TGCATTTATG AAAG AAGTTCATAAT CGGTTG TAGATTACTGCACTACAAC CGGTTA TAGA
                      XI                          II
ATAGCTCGGCTATATATATCTA TATATAA GTACTAGCAGGAGCA AATTAAA GTCTGACTT
    V                                       IX
TGATGA CAAT TCGCACGCCGCATTATTGGACTGGTCACGG GGAAAT GACAACGTACGCAG
                   XXIX                        XLI,VIII
CCAAGAGCCAAGCCTGT CAGTTA CACGTACAGCTCGCCATCGTCTCTA GGATA GATTC
            II            I    VIII,IV                    V
ATCGTCCGTGTCTGCAT AATAAA ATCTCCC AAAG  GATA TTTTGTGTCCTCATACTG CAAT
                                             XVIII       XLIV
GTGGCCTCTCTTATCTAATTACCTATCCAGCTCACCT CCGAC CCTAT ATGGTA GGTTCAT
                                          XIX     XVI,XVI
GGACTAGAATTGGTCCATGCCAGCCACGGATTTCAGT CGACG CA CAACA ACAAAAACGAA
             XII
GGTTGAATTGGAGG CAGTTG TGGGCCACAAACTAGCTAGTACTGAGCCCCTTGCAACCT
         XXVIII
CGCATGCTTA CAAACAC ACAGAGGACACTATAAGATGGGATGCACATGCACCACCCAGAC
    XVI       III     XLII    I
AA CAACA CTTGCGAGT CACTTG CAT TGCAGG  AAAG GTTTCT
```

Figure 14

```
                                II           V                            V
AAAACAGTATGAACTTTCAAAA[AATAAT] [CAAT]ACAAAAATGTTTCA[CAAT]TTCTGTAGAT
                 XXIX     XXX
TACTGCACTACAAC[CGGTTA][TAGAA]TACCCCGGCTATATATATATATCTATTTATAAG
                       II                       V
TACTAGCAAGAGCA[AATTAAA]GTCTGACTTTGATGA[CAAT]TCGCACGCCGCATTATTGGA
              IX                              XXIX
CTGGTCACGG[GGAAAT]GACAACGCAGCCAAGAGCCAAGCGTGT[CGGTTA]CACAGCTCGCC
           XLI,VIII                                   II
GTCGTCTCTA[GGATA]GATTCATCGTCCGTGTGACCGTGTCTGCAT[AATAAA]ATCTCCC
    I  VIII,IV                V
[AAAG] [GATA]TTTGTGTCCTCATACTG[CAAT]GTGGCCTCTCTTATCTAATTACCTATCCAG
            XVIII
CTCACCT[CCGAC]CCTATATGGACTAGAATTGGTCCATGCCAGCCACGGATTTCAGTCGAC
    XVI,XVI                              XII
GCA[CAACA]ACAAAAACGAAGGTTGAATTGGGAGG[CAGTTG]TGGGCCACAAACTAGCTAGT
                                 XXVIII
ACTGAGCCCCTTGCAACCTCGCATGCTTA[CAAACAC]ACAGAGGACACTATAAGATGGGAT
                   XVI      III       III       XLII      I
GCACATGCACCACCCAGA[CAACA] [ACACTTG]CGAGT[CACTTG]CAT[TGCAGG] [AAAG]GTTT
```

Figure 15

```
ACCACTTAGGAGGAAGGTACTGAACATTCTGCGCGTTTACCTGATTCTTATGGTTGAAAC
                XXXV        I                                I
TGAAATTGTATTTGGCTTGACCGTCGAAAGTGAACACTCCCCAGTGCCTCTCAAAGTTCC
         L                         V              XVI
CAGCAGATAAGTTTCTCTGATCTTCGTCCAAGAGACTTTCAATGTAGGTTTCAACAGGAG
                                 XV                I
GACGCGGGAGAGAGGCCGTCTTTTTCTCCAAGTGAACTATCAGTCCTTTAAAGAACGCCT
                                XV              XVII
CAGCAGTCAGTGATGTTGCATTTTCTGCTCCATCTGTAGGCCAACCGATCTTTGACACAA
    VIII         VII        V         V       XV
CGATATCCACCTCCGAAAACCCAATTGTGAACAATGCAGAGACAAGTGTGTCATAGCTTA
     I
GATCAAAGCTGTTTCTGTAGGTTTTACGTCCGTCTTTGTGAGCCTTTGCTGTTTCTTTAA
       I                           I                  I
AGAGGCTAAAGTCAAGGGAGATGTTCTTGTTCTGGTGAAAGCTTAGGAAAGGAGAGATTG
       I                   XIV                V
TCACAAAAAAAGGAGAGTGGTGCTTTGTGAGAAAGGAGAGGAGTTCAATCATCGTCTTGT
       LXII       I                              XIV      I
TGAGGTCAGCCCTAAAGTGTCCTGAAGAAGGTCGACCAGATTCAGAAAGAAAGGAATCAA
                                  XV                      I
AGCTTGAGGGGACTACAACCTTCACTTCATTTGCCAAGTTCGCCTTAACTAAAGCATTTT
    XLI                 V        I
GGATATTCATAGCTGCCCCAATCACAAAAGGCTTATACTGATTGCCATAGCTCTGGAGAA
               XV          IX    V                    L
ATGGCTCTTCTCCAACTGCTACATACCTGAAAAT CAATTCTTTTCTTTAATGATAATTTC
      V               V                  XVIII
ACAATAAGAAGATTGGCAATTTGGCATTGAAACAAATCCGACTCATTCACATTCCATAAG
               LXIII                XI    XLI
TTAAATTCCAGCTTAAAAATCTTAAATCTATATATATATAACTGGATAAGCAGAAGAGAA
     XIV     VIII                     XXIX
GGAGAAAGAAGATACTCGATTCGAACTCTGTTTCCACCGTTGAAGTAACGAGTGACATTG

TCATGTACCCAGCTCTCTGCTACCTTTACGGATGCATTCAAGCTCTTGAGCATCGAATTT
       VIII         V
TGGATTCCGATAGTGACACCAATATTAGAACCAGAGAGAGCTCGGAGAACTTTTGGGTCG
               V
GCATCGAAGAGCTTCACTTTGACAATGCCGTTTGATTTCAGAAGCTCTACAACCTTTGAA
               XIX              V        XV        X, XXIX
GGCGGAAGAGGGTGCGACGCTTCTGTCCCCCAATTTATGCCAACTGCTCTGACGGTTGTT
                         X              XIV      XVIII
CCCGTCAAGCTCAACCCTGCCGTGACGGCGAGGAGGAGGAGAAACAGCCGACGAGCCATC
                         L                XIV    V
AAATCCAGTGAATCTCGTACTTCCACGATAATGTCGGGCCGAAAATTCAATGTTTAAAA
                                       XXIX
AAACAAAACACTGCGTGCCGTTTCACGACTCAGCATCTCACTGTTATTTAGCTATCAAAA
                XIV
CGACACGGTGTTTAGAAATTGGGCTTGGGCTTCACATTCCCTAATCATCATCATCTCTGA
    XXX                                    XIV              V
AATAGAAATTATCTGAAACTTAGAGAGACAGAGAGAGAGAAAGCTCAAATTCAATCATCA
A
```

Figure 16

```
                                                                XLI
TAGTCTGAAATAACTATTTCTTTGATCATTAATTGAAGCATTTCTTTGGCTTA GGATA TT
            XV                  IX         XXII           XXIX
TTTGTTAATGA CATCTG TTCGAGGAGTGGA GGAAAA  TGTAAAGT GCCATGGA CTGTTA CA
    VIII                           V
CCT GATA TGGATCTTCTCGCTGCCCAAA CAAT CATGAACAAGCATGAACTTTCTCATGTT
                                           XXIX        XLI
GCAGTCGTTTCAGGCAGCATTGATGCTCCCAGAATACACC CTGTTG GGGTCCT GGATA GA
          LXIV        IX                              XXXIV
GAATGTATCACT CTAACAC GCA GGTAAA CCTGCATCTATTTCCCCTCGGTT TAACTG TTT
           XXXIII  XXXII       XLV       XLVIII
GTCCCAAGATCA CCTTTT  CATATG GATT GTTTTTA ATG AACCTAAC TGACTAACCTAGTC
     XXXII
TTC CATATG ACAAGAGTGTGTAGAGAGTCTGTGTAACTATAACTTGGGCTGCCAGGTTTC

CCACATTGGATGTAGTAGAAGTTAAATTAGTTAAAAAAAATTACTTGCAACTTTTTGTTT
               I          I            XLV
GCTCATCAGAGG AAAG GAGTGAGTCGC AAAG TCCAGTTTGCTAG ATTTTTA ATTTTAGAG
        XV            VIII  VII    IV                            V
CTTT CATCTG TATTAGAGTT GATA   CCGAAA   ATATT GACCCAGCAAATAAGGTTCCT CAAT
    XV                                  VIII
T CATTTG AAACTTTTCGGTGTAGATGCTGCATTGGAGAT GATA CTGGTTTTTCTTAACCT
         XXXV
TTTCTCTTGC TTGACC TGGCAGGGCTCTAGCAACCAGAATGTACCTCCTAAATTCGCTGT
                                                            V
ATCTGTAAATGGTCTTGCTTTGTAACTCTTCTGAGCTGACCAGGGTGATTT CAAT TTGTT
                 V
TCTTCTGTGAGGCTCCGGG CCAAT TTTTGTTCTTTGTATTAAGAGATTTGGGGAGAATGA
                                             XV
GTTGGCTGGTGCAGCGTGGATGTTTTTTGTCTACTC CATCTG TTGGTTTAAATGGTGAAG
                   V, LVI,I
CCCCCATTTCTCACTTAAGGTGCTGAG CAAT CC AAAG GGAATCGAAACATGGAGCGTGGT
      XIV         XIV            LXI    VIII       XV
TCTG AGAAA ATCTTC AGAAA TTTTCCTGA AACCAA AGATA TGTGCT CAGGTG ATTCGTTA

CCATTTACACTTTTTTCTTACAGATTGTTACTGTACCTTACTTAGTATTGTCTATTTTGT
 I                    IV       XIV     LXV         I
 AAAG TGCTTTCTGACTTATATC ATATT GAGAAA GT TTTGACT ACTT AAAG ACTAACAGTG
 XVI                                       IV
T CAACA ATTGTAAGGGTTTCCTTGTCCACTATTTTGT ATATT GAAGAACATTGAAATATA
              XI              XXIV
TTGGAATGCCC TTATTT CTGGTGTGTG TGTCTC TCTCGGTGAGCCGCAAGGGCATGTTGA
                XLI                XIV           XIV
CATCTAATTGTAT GGATA TTTTTCTCTA AGAAA ATTCCTAG AGAAA ACAGTAGTCAGGCC
      LVII                      XXXIII    IX
ATTGTGTT GGTTAA ACAACCCTCCTAAAA CCTTTT A GGTAAA GAAGAAGCAACCCCGCAT
              XLVIII                          VIII
GGGTTGAATGA CCTACC TAACCTATACTTACCTCCATCAT GATA TAGCTAGTACCCTCTG
       LXVI  VIII     XII       XI
AA CATGCATG  GATA  CACATG CTATATAA TCATTCGGGTGTGATTCCATTTATACCGGAAA
A
```

Figure 17

```
                  XVIII         I                              V
CTGGCACGACAGGTTTC CCGAC TGG AAAG CGGGCAGTGAGCGCAACG CAAT TAATGTGAG
                 LXXI              XLIII
TTAGCTCACTCATTAGGCA CCCCAGGC TTTAC ACTTTA TGCTTCCGGCTCGTATGTTGTG
         XLIX      V          III
TGGAATTGTGAG CGGATA A CAAT TTC ACACAGG AAACAGCTATGACCATGATTACGCCAA
                XXX                         LXX
GCTATTTAGGTGACACT ATAGAA TACTCAAGCTATG CATCCAACG CGTTGGGAGCTCTCC
XXXII        XLII
CATATG GTCGACC TGCAGG CGGCCGCGAATTCACTAGTGATTGGACACTGAC
```

Figure 21

```
                    XXXV
AAACAAAATACGGACGG TACGTA GGACGACCAGGGAGACGTTGAAGTATACGATCGCGAC
       LXVII      XV
GGCTCGGC GGGCGG C CAAGTG GATGAGAAGGAGGCCGTACCCTAGTACCGGGTTGGGAGA

AGAAGGCGGCTATAAGAATCGGCGGTCGGTCGTCTACTTGTGTCAGCCCATAGTTCCGTG
                                              LXVIII
CTTAATTGTAACCTTGCTGTGGGTGGGTGTGAGTGAGAC TGACTCA GTAGTACGTTGGAA
             XIX
GAAGGAGAAGCAGA CGACG ACGCGGACGGCCCCTGTTCCTCCGCCGTGATCGATCGCTCG

AGGAGACGCGTGCGTGTCGGTGTGTGTGAAGATCGCTCGAGGGTTTAA
```

Figure 22

```
                                                    III              LXXII
CTGTACTTCCAGAATCACATCCCGAACTTCCCACCCCTGGCCACCTGCTCCTTCCCGGAT
    XV           V                XXIX
ACAAATGGGAAGCCAATTCGATGCACCAGTTATGGCCAGGCTCTGTACAGCCTTCCGGGT

AGTAAACTGATTCCCCAAGAAGCGGCAGAATGGTTCAGAGTTTTCTACCAAGGTCTGGAC
                                IX              XXXIX
AACCCTCTCTTCATCCCTTACAGGGAGTCTGAAAATTTTGAAAACCCAGTCTCCTTCAGG
                       XVIII         XXIX
TTAGACAGCTTTGCCGATGATGCCGACACTCGGCAGTTATATTCCATCATGATCCGCCCT

TGCTTCCTCCCAGGTTGGCATGATCACCTCTAACATGATCATCAAGCCTGGTTATGAGTC
                                            XV
TTATCAGCCGGTCGTAGTGGCCCGGCAACTTGGTCTTGGGCAGGTGCCTCCTCATTTCTT
          XLVIII                    XLVIII
CCTTCACCACCTAACAGAGAGCAGAGCAGAATCTCCTACCCAGACCAC
```

Figure 23

```
                                                                    XII
AAACTCTCTTCCAAAACAGAGTGCACAAGCTGGGGTGTTTATCTTAGGATC|CACATG|AAA
      I              L
ACCA|AAAG|CCCTGTGACA|GATAA|AGAGCACACGGCTTTTCTGAATTTCTGGTTGGAACAT
      IV                        XVII
TTC|ATATT|CTGTGGTTCTTCGCTTGCT|CCAACC|AAGAACTACCTTTCCTTGGCCTATGAA

CTTGCCAGAGGCACTCAGCTTGGCATCGGCAAACTGTTCCTTGGAGAAGTCTATCGGTATC

XVI                            I                XV
TC|CAGCTG|ATGTCTGTCAACCTATTTTCTCA|AAAG|ACAGTCAAAA|CAGGTG|GTCCCTGGT
              XXIX          XVI
GGTTTATT|CAGTTA|TGGGCT|CAGCTG|TACTTCCAGAATCACATCCCGAACTTCCCACCCC
        III          LXXII        XV        V              XXIX
TGGC|CACCTG|CTCCTTCC|CGGATA|  |CAAATG|GGAAG|CCAAT|TCGATGCAC|CAGTTA|TGG

CCAGGCTCTGTACAGCCTTCCGGGTAGTAAACTGATTCCCCAAGAAGCGGCAGAATGGTT
                                                                    IX
CAGAGTTTTCTACCAAGGTCTGGACAACCCTCTCTTCATCCCTTACAGGGAGTCT|GAAAA|
        XXXIX                                    XVIII      XXIX
|T|TTTGAA|AACCCA|GTCTCCTTCAGGTTAGACAGCTTTGCCGATGATG|CCGAC|ACTCGG|CA|

|GTTA|TATTCCATCATGATCCGCCCTTGCTTCCTCCCAGGTTGGCATGATCACCTCTAACA

TGATCATCAAGCCTGGTTATGAGTCTTATCAGCCGGTCGTAGTGGCCCGGCAACTTGGTC
        XV                              XLVIII
TTGGG|CAGGTG|CCTCCTCATTTCTTCCTTCAC|CACCTAAC|AGAGAGCAGAGCAGAATCT
XLVIII
|CCTACC|CAGACCAC
```

Figure 24

```
AAAACCATAAGGGATTCATATAGAGCATCGTTAGTACTAGTACAGTTCTTGTCTATCAAG
                            XV
TTTTACTAGTGCAGTATAATTTTGTA CAAGTG ATTGAATATCGTCAGTAGATTCAGTCTA
         III              V   XI              XV        XIV
ATCGTGC CACTTG GAATATAACACATA CAAT TATTTAACATAGTGT CAAATG TATG AGA
       I    VIII
AA CCT AAAG AC GATA GTCAAGAGTAGTATCTCACAAATACTGGAGTGCCTACTCCTGCA

GGTGGACATAGTGGCGCCACCAATGGTTCATTGGCTTGGGGTCTTTGCTACAAACGTGAA
                          X                          XXIX
TTGAGCCCAAGCCAGAGCTATTG TGACG ACAGCAACGAATTGTA CCGTTG TGCTGAAGGA
                                              VIII
GTCGAGTACTATGGTCGAGGCGCCCTTCCTGTTTACTGGTCAGGCT GATA TGTTATTTCT
  XII
CC CAGTTG TTGTTTATTATGAACTAGCTGGGCCAAGCTATTGATTTTGTATCTACTTGTA
      XLII                                I       XXIX
AACGATC TGCAGG AACTACAACTACGGTATCGTGGGTAAGGGCAT AAAG CAGGAT CTGTTG
                                  XV
AACCACCCAGAGTTATTGGAACAGAATGCGACCCTAG CATTTG AAGCGGCAATCTGGAGG
           V                                              XV
TGGATGACT CCAAT GAAGAGAAGGCAGCCATCAGCGCATGATGTCTTTGTTGG CAACTG G
   LXI, LXI XIV,I
A AACCAA CCAAG AAAG ACACCTTGTCCAAGAGGTATCCTGGCTTTGGTGCTACCATGAAC
             XXXII   IX, I       XXV
ATCTTGTATGGCGATCT CATATG TGGT AAAG GGACCA TTGACC GTATGAATGTCATTGTA
      XVI                                           VIII,L
TCCCACTAT CAACA TTATCTTAATTTGATGGGAGTTGGTGATCAGCAGTCTGGA GATA AC
     XVII          V               I
TTGGATTGTG CCGAC CAAGTTCCATT CAAT CCGTCATC AAAG AATCTAGACTCATGAGCA
              IV
AGTTGCTTGTCAGATCTATGT ATATT TCCTTTAAGGCACATCCATCTTGCTTCCCAAACT
                         IV, XI                                LI
GTATAAATCTTGTATGCGAATCTATAAGGT ATATT ATTTAGTAGCTCTGAGGAC TACTATT

GCGTCTTGGAAGTTTGTGATCTACTTATGTAATCTCGTAATCTTCTCTCACTATGTGATCT
       IV                               VI, X
GCCCTGC ATATT ACAGGAGATAAAATTACATTCTAA CATGTG ACGCCTTTGTTACTGTCG
XLI,VIII         XVI      XV
TG GATA TGTTGTCAG CAACA CATCTGTCATCGTTCTCTTGTTATGTGGACATGATTCATG
    V, VIII,L
TAA CAAT GATAA CTTCTAATCGAACTGTGTGGAGGGATCTTGTCTTACTTTGTTTTCTGA
                                                      IV
ATTCCTTCAGCTACACAGTTTTTTCTTCAAATTTTCTCTATTTTGGATTA ATATT TTGAT

GTTAATTTTGTAAGGCACAAACAGTGAAACCAGACTTTGTTGTAGAAGTGTAAACATACA
      XXXII           XVI
TGGAAG CATATG TGTGGAAAATATC CAACA TACAGACAAAAACTCAAAATCTATTGTGAA
        VIII                       IV
TTTACTGA GATA ATATGCGTAGGGAGTTCAGTGGC ATATT CTTGCAAAACTATAGATGGG
   VIII,IV                    XV              XXXVII
TTG ATATT TACCACTGAAACAGCTTATC CAAGTG CCGGAAGGGGA CCGTCC TCTGGACAC
    XII      XLI,VIII        VIII
C ACACATG GGCCTG GATA GCCAGGTACA GATA GACTGACTAGAGAGTTCTGTCTTTTCC

TCTTCCATTTCAGGGCAGTAGAACTGGCATTCAAACAAGGCAAGCAGGAAGGGGATGAAG
     V
CTCA CCAAT ATCCCCCATCTTGCCTCCTCCTCCTCCAGCTTCTTCTTCTCCAACT
```

Figure 25

```
               I    LXVIII
CCTATAAAGAAGGGCGGCTATCTGGCCCATGGGAGTACAAGCTCCCCGGGTGAGATGTAAATTTTCCA
    II       XIV              IV                                   I
AATAATGGTTAGAAAAATATGAAAACATATTTGTTGTGTCCATGTCTGATGTGCATGCAAAGTTTTAT
    LV                                XXXIX
TAACAAAAAACAAGTTTTGTGCCCAGCAAAAAAACCCAGTGCTCTATAGTGAAAATTCTCTAAATCGA
                                           XI            XIV,I
AACACTTATTGAACACACAACCTCAACCACCTTGTCTAATTATTTCAAGAATCCAGAAAAGAAAATTG
        VIII   V              XL,I                    XIV
ACATGGAGATAGGCAATTTTTCATTGAAAACGAACAAAGCTATCCACGCCACTCAGAAACGTAGCTAT
        XXXIII        XIV                                XXXIII
GGTGGGCTCCTTTTCTTATATAGAAATGGCCATGAAATCTTCGCATTTCGAAAATCGTTCCTTTTCAT
                         LXXIII         LXVI
AGAGTCTGGCCTGGGTGCAACTTTGAATTTCCCGCGTGTATATACATGCATATAGCCATAGGACGGAG
                       V                V
AACCGATTGTGCATCAATATATGGCCCACTCCCAATTTTGTTTCTATTATCGTCCACTCAGCTATATA
                                                                    IX
TCAGCTCCCTCGCTCACTGCTGAAGAGCACACGTACAGGCACCCATCCACCGGAGTATACTAGCCAGGA
ATATCCTGCAACTCGA
```

Figure 26

```
                                VI                                    V
CCTTATGTATAAAACCAT[CATGTG]ATGTATGATTAGTATTAGAAGTA[CAAT]GGTTGTACA
         XXIX
TATAAG[CTGTTA]AAGAATTATGGTTTTTCTAATTCTCAGCTAACCGGGATTTAGACTAGT
              V
GCTCGGTCAACT[CCAAT]ACTATTTGATTATTGTTTCAAGACTCGTGCCCATTGTTTCAAG

ATTCGTGCTTATGGGCTCACCCAGCTTTATCTCTTCTCTTCCCTTCTCTTGGGCACGGCC
XVI,XIV,I      XXXIX                                 XVIII  LXXV
[CAACA][GAAAG]ATGAGA[GAACCCA]CCGCCCACCTCGTCGGAATTGAAG[CCGAC] [GACGTC]GA
          I                  XIV
GCCTGGACCAAGCTAGAGG[AAAG]GCTGACTCTGGCGAGGA[AGAAA]CTTAGGTTGGGGGAG
       LXXVI
AGG[GTACGTG]ATCACTGGAGCGAACCGGAGAAGGTGGGGGTTTAGAGGGATGGCCAGGGG
          LXVI           XVIII,XIX
TGGCACTG[CATGCATG]GA[CCGAC]GAGAAGCAAGAGCTTGGGGCAGGACGAGGCATCACGA
                                              XL
TAGTGCGCCGCCCACGGGTGGGATGGCGGCGAT[CAAGTCCATC]GTCGATGCTCGCCGAAG
            XVI      VIII            XIX           V
GAGGAGGA[CAACA]AGGC[GATA]GGAGGGACGATGG[CGACG]TCAGT[CCAAT]GGGAATTTGGT
       XIII                                        V
TAATTCT[CCGTCG]ACTGCGCCCTAAACGGACCTTTAGAAT[CAAT]ATGATGCATGATTAAA
                   IX                       IX
TATTTATACCGTCATACT[GGAAAT]TTGACTATGTGAGCACGTACG[GGAAAA]TGAACCTCA
  IX       XLV                       XLVI
[GAAAAT]C[ATTTTTA]TGTTCATCACTTCATACC[AACGTT]GGTAAGAGCAAGTTAGATTACT
     IX              XV            XIV
GTGGAT[GAAAAA]CGCACAGCAGTG[CATCTG]CCTGCTTAAG[AGAAA]CGACCAAGTCCCCT
 LXVII                                          XLVIII,LXXIV
[CACGAAAA]GGCCATCCGCAACGCTCCTCCGCCTCTTCCTCGCCGTG[CACCAACC]CCCTGC
                      XXXV
CACGAAGGTGCCAACGCGCTCATC[TACGTA]GCCACCACCCGGTCCGTCATGGCTCATGGC
           V            V
CACTGGAGCTCCACCCA[CCAAT]GA[CCAAT]CCAGACATCCAGTGGTCAACCTCGCCTTCCA
   LXXIV,XXXIX      XVIII       XLVIII
GGTCCATA[CCAACC]CACACC[CCGAC]ACCCG[CACCTACC]TGCTCTGCCTATTTAATCCCT
                                        III
GCCCTGCCTCCATTCCCCTCCAAGAAGAGCCT[CACCTG]CTTCCTCTGCAACTCGAGCTCC
                                              XVI
TCTTCAGTCTTACTCGCTCTAGTAGTTCTTTGCAACGAT[CAACA]CTGTCAGAATCCAGAT

```
                              I
CTGCACAGGCGACCAAGACGCGAACA AAAG CGGGTCCTCAACTTGCCTTGAAATGAACCT
    XV
T CAGATG TAAGTGGTGTCTGCCAGGACTCCTTAGTCCTTATTGATTGACTGACCCATTTT
          XXIV       III                     I      XXXII
AAACA TAACTG ATCGTGAA ACACGAG AGACTCTTGGCAGC AAAG GGATT CATATG CAGGA
  I           XIV           V       IX      IX
 AAAG AGCCAGCA AGAAA GGGTCGTACTG CAAT A GGAAAT A GGAAAT ACTCACGGTCACGA
              XX          XV                              XXX
TCGAGCTGAA CTCCCAC ATGGC CATGTG TGCTAGCTAGCTTAATTGAAT ATAGAA TACGT
                                      XXXIV    XV     IV      I
GTGGTGAACAACTAAACCATGGTGAACAA CTAACCAT CATCTG  ATATTAT AAAG CTTGG
                              VI                              V
CCAAGGCCTTATGTATAAAACCAT CATGTG ATGTATGATTAGTATTAGAAGTA CAAT GGTT
                 XXIX
GTACATATAAG CTGTTA AAGAATTATGGTTTTTCTAATTCTCAGCTAACCGGGATTTAGAC
               V
TAGTGCTCGGTCAACT CCAAT ACTATTTGATTATTGTTTCAAGACTCGTGCCCATTGTTTC

AAGATTCGTGCTTATGGGCTCACCCAGCTTTATCTCTTCTCTTCCCTTCTCTTGGGCACGGCC
XVI,XIV,I           XXXIX                           XVIII   LXXV
 CAACA GAAAG ATGAGAG AACCCA CCGCCCACCTCGTCGGAATTGAAG CCGAC  GACGTC GA
              I                          XIV
GCCTGGACCAAGCTAGAGG AAAG GCTGACTCTGGCGAGGA AGAAA CTTAGGTTGGGGGAG
      LXXVI
AGG GTACGTG ATCACTGGAGCGAACCGGAGAAGGTGGGGGTTTAGAGGGATGGCCAGGGG
        LXVI      XVIII,XIX
TGGCACTG CATGCATG GA CCGAC GAGAAGCAAGAGCTTGGGCAGGACGAGGCATCACGA
                                       XL
TAGTGCGCCGCCCACGGGTGGGATGGCGGCGAT CAAGTCCATC GTCGATGCTCGCCGAAG
           XVI       VIII              XIX           V
GAGGAGGA CAACA AGGC GATA GGAGGGACGATGG CGACG TCAGT CCAAT GGGAATTTGGT
         XIII                                 V
TAATTCT CCGTCG ACTGCGCCCTAAACGGACCTTTAGAAT CAAT ATGATGCATGATTAAA
                IX                        IX
TATTTATACCGTCATACT GGAAAT TTGACTATGTGAGCACGTACG GGAAAA TGAACCTCA
 IX      XLV                       XLVI
 GAAAAT C ATTTTTA TGTTCATCACTTCATACC AACGTT GGTAAGAGCAAGTTAGATTACT
    IX           XV              XIV
GTGGAT GAAAAA CGCACAGCAGTG CATCTG CCTGCTTAAG AGAAA CGACCAAGTCCCCCT
 LXVII                                     XLVIII,LXXIV
 CACGAAAA GGCCATCCGCAACGCTCCTCCGCCTCTTCCTCGCCGTG CACCAACC CCCTGC
                                XXXV
CACGAAGGTGCCAACGCGCTCATC TACGTA GCCACCACCCGGTCCGTCATGGCTCATGGC
                           V        V
CACTGGAGCTCCACCCA CCAAT GA CCAAT CCAGACATCCAGTGGTCAACCTCGCCTTCCA
           LXXIV,XXXIX   XVIII       XLVIII
GGTCCATA CCAACC CACACC CCGAC ACCCG CACCTACC CTGCTCTGCCTATTTAATCCCT
                                       III
GCCCTGCCTCCATTCCCCTCCAAGAAGAGCCT CACCTG CTTCCTCTGCAACTCGAGCTCC
                                            XVI
TCTTCAGTCTTACTCGCTCTAGTAGTTCTTTGCAACGAT CAACA CTGTCAGAATCCAGAT
A
```

Figure 28

```
                                    LXXIX           IV
CTGAAGTCGTTGCCTTGGCGCCCAGAGTCC|ACACGAG|GTGAC|ATATT|GATGGCCACACCA
    XIX                                 XVI
CCACCTTCGT|CGACG|TCATGCGACCACCTAAGGCAC|CAACA|AGGAGAAGGGGAGAGGGGT
                   LXXX
GGCAGTCTACGATTTCCT|TGAGTCA|CCTCTGAGAGAGAGATGCAATGGAGGGTGGTTGCA
                         I    LXXVIII
AAATTAGTGCTGGGTGTCC|AAAG| |AAACCCTAA|ATCGCCTTTGTATGTCTTGGGGCTGTAC
          XII  VIII,XXX  XI      V                         I
CGGCTCG|CACATG|C|GATA|GAAT|TTATTT|TGTT|CAAT|AGAGACAGACCATTTCT|AAAG|AAA
    IV                II                           XII
|ATATT|ACTTCCTCTATCCA|AATTAAA|TTTCATGAACTATTCTAAATT|CACATG|TATCTAT
                                                              I
ACATACTCCCTCCACCACAAATAAGTGGACATCTAGCCCTAAACTTTGTCCATA|AAAG|AG
              V       XLIII                       XXX
TGTACTCCTATCTTC|CCAAT|GC|ACTTTA|ATTGCTTCTCTCTCATCGC|ATAGAA|ATCAAAC
   II, IV           IV        XI
CT|AATAAT|ATTGAGCAT|ATATT|TTCT|TTATTT|CTACAAGCACTTAGCTCATTACAGCTA
   II      I           VIII                           XLIII
A|AATAAT|T|AAAG|AGGAGA|GATA|TATCTTTCACTGCATTTTCACTTC|ACTTTA|TAATTTA
    IX                  XI
TCTT|GAAAAA|CCTGCATGTATAC|TTATTT|GTAACGGAGGGAGTATATGTTACAAGTAAT
                          I                I       LXI
TAATTTGGGACGGTGGGAGTATA|AAAG|GAGATTAAATAGGG|AAAG|A|AACCAA|AGAAGTGG
         XLV          IV          II
CTAGAGGCA|GTTTTTA|TATAAT|ATATT|AAA|AATAAA|AAGGAGTGTGGCCTGCGTTTGGTT
                                          XII
CGACCGTACGAGGTGCAGAGTGCAGACACATC|ACACATG|GCGATGGAGTAAACCTGCATT
    XXIX
G|CAGTTA|ATCAGCACAGGGGCACAGCAGCAGCAGTATATACTGCCATCGATTAATTGTTT
                                 LXIV         VIII         V
TAATCCGTATTATCTTGTTGCTAACAGCG|CTAACAC|AC|GATA|CCGGGG|CCAAT|TAGCAGG
             XXXVI                     XXIV      V
GAGAGACTG|AGCGGG|TGGGGGCACGGTGAG|TGTCTC|CG|CCAAT|CAGCGCTCGACAGCATC
                              V        V
CTGCCCCCCCCCAAACCACACCC|CCAAT|TA|CAAT|CCATCCTCTTCTCCTCCATCTTCCCT
    I
CTTT|AAAG|CTGCATCCCTTGCCTGGCCTCGCCGCCGCGGTGACTCCTCCGATCCACTCCA
             V
CTCCACTCCGG|CCAAT|TCCTTGGTAGACAGCCGGCAGCTA
```

Figure 29

```
                                                      LXI, IV
TATTGGTTTTCATAGACATGGACATAGTTTCACTTATTAACG|AGGTCA|TATTATTAAGGA
      II             XXV                  I      XXIX,XXV
G|AATAAT|ATGATGGAC|TTGACC|TAATC|AAAG|CATAG|CAATTG|ACCACGTTACATGGATCT
                XXIX              LI              XXV
AATTGCGAAACTTTT|CCGTTA|TCATCTA|TACTATT|CCT|TTGACC|ATAAGATTATACAACT
                                        XIII
CTCGAGTATTGGAAGAATTCATAACTTGTTGCAA|ACGTCA|CTTCGTTATTGGGTGATCAT
      I        LXVI         XI         VIII
|AAAG|CTATCTCT|CATGCAT| |TATATAA| |GATA|CTTGTTGTTGTATGTTATCAAGAGTGGG
        V                 I             IV              IX           V
ATTTTT|CAAT|CCAAGTAACGG|AAAG| |ATATT|CTCTGGCCCTCTT|GGTAAT|ACGCACT|CAAT|
        V           LXI                            XIV
TTCTTG|CAAT|CCCGTGACT|AGGTCA|CATGAGGGTGCGCTATTATGAT|GAAAA|GAGTAC
            L              V         I                   XLIX,L
TTACCAGTAACGA|GATAA|GGA|CAAT|GTATG|AAAG|GTATCAACGATCAAATCT|CGGATA|AC
      VIII                                                L
TAA|GATA|CCGCAGGACATGGGAATTATATATGAATGACATAAGTGGTTCACTA|GATAA|GA

TGATTGTTGAATATGTGGGAGTTAATATGGATCTCTAGATCCCTCTATTAACCATTAGCT
                                         LVII
ATGTACATAGTCATGTCCGCATAATCGCGAATCTGTAG|GGTTAA|ACACTTAAGATTCGAC
        XLI              XV
GTTGCTA|GGATA|GAGAGATGT|CAAGTG|CAGTATTTTCGGTGTCCCGAATGGATTCGGGA
    XXIX
TATCA|CGGTTG|GACTCGGAAGGGCAAAAACCCCATAGGAACATATATGGGAAGTATCGGA
           I    XXIX          I           XXXIX
ATGGTTCCGG|AAAGT|CGGTTG|TACCGG|AAAG|TTCCAAGGGGG|AACCCA|CCTAGCCTAGG
             XXXI    XV                  XXII
GCCGG|GTGGGCCCG|ACC|CACGTG|C|CAAGTG|GGCTATAATC|TGCAAAAT|AAGGGCCGAAGT
    LV       XLII, LXI                            XXXV
G|TAACAAA|AAAAA|TGCAGG|TCAAATTGTTGGCTCAAACTCATA|TACGTA|GACTCTTTTC
          III      IX                                  XXXV
GTTTTGATCT|CACTTG| |GGAAAT|CAAACGGCTACACAAAATCTTAGAGCATC|TACGTA|CCC
          I                                VIII        LXXVI
CAAGACAGAGGTG|AAAG|GGAAGGAGCAACCCCAAGACA|GATA|GACGTACC|GTACGTG|CAT

GTGTAGGGTAGCAACCACACTAATTTACATCCATCTACTCATCCATCCATCTTAGCATAT
      I          I
CAT|AAAG|AGAGGG|AAAG|TAGCACTGCTAGTCCTCGGCTTGGTAGTGCTATCTGAGTAGGG

AGAAGGAGCAGGGAGAAGAAGAGAGAGATC
```

Figure 30

```
       II, I
A AATAAAG AGCGCCCTTTGTAAAAAAAAACATTTTGCGTGTACGCGGGTGTTCATGCCTG

XXIX                                    VIII
GC CGGTTG AGACCTGCCAGTAGTGGTGGTGTCTA GATA TGGTAGCAGTACCCTAATTAAG
                         V                    I        I,XXII..
CTAG GGCGAGTGCGAGAGCCGAGAT CCAAT CCGATCTGTACCCCACG AAAG GG AAAGGA

XXII,I                                            I        XVI
AAAAG ATTCTTGCCTTGCCCCGCCCCGCCTCCCTCTCCTCGGC AAAG CTATA CAACA CCA

XV
CCACCACAGCCACAGAGCCACAGCCAGTCGCCCGGCA CAACTG CAGCCTGACCAGGGCCCT

I                   V
C AAAG AAAACAAATCTAGGA CAAT CAAGCCGCTGCTAGCTAGG
```

COMPOSITIONS AND METHODS FOR THE MODIFICATION OF GENE EXPRESSION

REFERENCE TO RELATED APPLICATIONS

This application claims priority to U.S. provisional patent application No. 60/580,007, filed Jun. 15, 2004.

TECHNICAL FIELD OF THE INVENTION

This invention relates to the regulation of polynucleotide transcription and/or expression. More specifically, this invention relates to polynucleotide regulatory sequences isolated from plants that are capable of initiating and driving the transcription of polynucleotides, and the use of such regulatory sequences in the modification of transcription of endogenous and/or heterologous polynucleotides and production of polypeptides.

BACKGROUND OF THE INVENTION

Gene expression is regulated, in part, by the cellular processes involved in transcription. During transcription, a single-stranded RNA complementary to the DNA sequence to be transcribed is formed by the action of RNA polymerases. Initiation of transcription in eukaryotic cells is regulated by complex interactions between cis-acting DNA motifs, located within the gene to be transcribed, and trans-acting protein factors. Among the cis-acting regulatory regions are sequences of DNA, termed promoters, to which RNA polymerase is first bound, either directly or indirectly. As used herein, the term "promoter" refers to the 5' untranslated region of a gene that is associated with transcription and which generally includes a transcription start site. Other cis-acting DNA motifs, such as enhancers, may be situated further up- and/or down-stream from the initiation site.

Both promoters and enhancers are generally composed of several discrete, often redundant elements, each of which may be recognized by one or more trans-acting regulatory proteins, known as transcription factors. Promoters generally comprise both proximal and more distant elements. For example, the so-called TATA box, which is important for the binding of regulatory proteins, is generally found about 25 basepairs upstream from the initiation site. The so-called CAAT box is generally found about 75 basepairs upstream of the initiation site. Promoters generally contain between about 100 and 1000 nucleotides, although longer promoter sequences are possible.

To date, although numerous promoters have been isolated from various plants, only a few of these are usefully employed for expression of a transgene in a plant. Currently CaMV (cauliflower mosaic virus) 35S promoter and its derivatives have been most widely used. This promoter is constitutive, i.e. continuously active in all plant tissues. However, the CaMV 35S promoter exhibits lower activity in monocot plants, such as rice and maize, than in dicot plants, and does not exhibit any activity in certain cells such as pollen. Many other promoters that have originated from dicot plants have also been used for transgene expression in monocot plants, but exhibit lower activity than promoters originating from monocot plants.

Intron sequences inside monocot promoters have been shown to enhance promoter activity. These include the first intron of rice actin (McEloy et al., *Mol. Gen. Genet.* 231:150-160, 1991), intron 1 of the maize ubiquitin gene (Christensen and Quail, *Transgenic Res.* 5:213-218, 1996), and the maize sucrose synthase gene (Clancy and Hannah, *Plant Physiol.* 130:918-929, 2002). Using the actin intron next to the 35S promoter increased expression 10-fold in rice, compared to 35S promoter alone (McElroy et al., *Mol. Gen. Genet.* 231:150-160, 1991). Studies have shown that the introns used must be within the transcribed portion of the gene and preferably within the 5' untranslated leader sequence (Bourdon et al., *EMBO Rep.* 2:394-398, 2001; Callis et al., *Genes Dev.* 1:1183-1200, 1987; Mascarenhas et al., *Plant Mol. Biol.* 15:913-920, 1990). It has also been shown that the intron plays a role in tissue specificity in some cases (Deyholos and Sieburth, *Plant Cell* 12:1799-1810, 2000).

In addition to introns, untranslated leader sequences (5'UTLs) have also been shown to enhance expression. It appears that 5'UTLs from dicots work better in dicot hosts and those from monocots work better in monocots (Koziel et al., *Plant Mol. Biol.* 32:393-405, 1996).

Constitutive promoters have been isolated from monocots, characterized, and used to drive transgene expression, for example the rice actin1 promoter and the maize ubiquitin 1 promoter. However, even within monocots, using a promoter in a heterologous system may give unexpected expression patterns. For example, the rbcS promoter from rice has a different pattern of expression than the endogenous maize rbcS when transformed into a maize plant (Nomura et al., *Plant Mol. Biol.* 44:99-106, 2000). Therefore, there is a need for the development of promoter systems from monocots and, in particular, important target species such as forage grasses.

Constitutive promoters for use in monocots, especially the forage grasses, are not abundant. Examples of these may be promoters from the genes of actin, tubulin or ubiquitin. Actin is a fundamental cytoskeletal component that is expressed in nearly every plant cell. The alpha- and beta-tubulin monomers associate to form tubulin dimers that are the basic units of microtubules, found in most cells. Ubiquitin is one of the most highly conserved proteins in nature. It has been linked to many cellular processes such as protein degradation, chromatin structure and DNA repair, and is highly abundant in nearly every plant cell (Kawalleck et al., *Plant Mol. Biol.* 21:673-684, 1993).

In some cases, constitutive over-expression of a transgene may interfere with the normal processes in a plant. The development of tissue-specific promoters, designed specifically to drive a particular gene of interest should help to alleviate these problems. For example, to manipulate the plant secondary cell wall, vascular specific promoters may be preferred, and to manipulate flowering habit, floral specific promoters may be preferred.

A number of genes in the pathway for lignin biosynthesis from *Lolium perenne* and *Festuca arundinacea* are described in International Patent Publications WO03/040306 and WO03/93464. These include Phenylalanine Ammonia Lyase (PAL), the first enzyme of the general phenylpropanoid pathway. Isoforms of this gene from *Arabidopsis* have been shown to be stem and vascular specific in expression (Ohl et al., *Plant Cell* 2:837-848, 1990; Leyva et al., *Plant Cell* 4:263-271, 1992). Several isoforms of 4-Coumarate:CoA ligase (4CL) have been isolated. 4CL is an enzyme that catalyzes the formation of CoA esters from p-coumaric acid, caffeic acid, ferilic acid, 5-hydroxyferulic acid and sinapic acid. A number of caffeic acid O-methyltransferase (COMT) grass genes have also been identified. COMT genes, such as those from *Arabidopsis* and the monocot alfalfa, are expressed in lignifying tissues (Goujon et al., *Plant Mol. Biol.* 51:973-989, 2003; Inoue et al., *Plant Physiol.* 117:761-770, 1998). Cinnamyl alcohol dehydrogenase (CAD) catalyzes the last step in monolignol biosynthesis, and the grass CAD gene has also been identified. The promoters of these genes will be of use in manipulating cell wall modification and digestibility.

A number of genes involved in flowering development from *Lolium perenne* and *Festuca arundinacea* are described in International Patent Publication WO04/022755. The control of flowering has been extensively studied in model species, in particular *Arabidopsis thaliana*, and a large number of genes and transcription factors involved in floral development have been identified; for a review see Putterill et al., *BioEssays* 26:363-373, 2004, and Simpson & Dean, *Science* 296: 285-289, 2002. In particular, the MADs box family of transcription factors play a role in the transition of vegetative to floral growth and show differential expression through floral development (Petersen et al., *J. Plant Physiol.* 161:439-447, 2004. In the manipulation of floral development, it is a prerequisite that floral specific promoters will be required to drive transgene expression. Therefore, the isolation and development of floral specific promoters from monocots is necessary.

A number of genes involved in anthocyanin and condensed tannin biosynthesis from *Lolium perenne* and *Festuca arundinacea* are described in International Patent Publications WO03/040306 and WO03/93464. Many of the genes involved in anthocyanin biosynthesis show specific cell type and developmental patterns of expression. The promoters of these genes will be of use in transgenic expression of genes, particularly to manipulate anthocyanin and tannin biosynthesis. Dihydroflavonol-4-Reductase (DFR) catalyzes the reduction of dihydroflavonols to leucoanthocyanidins, the precursors of anthocyanins and condensed tannins. DFR is a later key enzyme that may control the flux into the pathways of anthocyanin and condensed tannin synthesis. Another key enzyme that may control flux into these pathways is chalcone synthase (CHS), which catalyzes the condensation of malonyl-CoA and coumaroyl-CoA into chalcone intermediates. In many species, several gene family members exist for each enzyme. These different family members are differentially expressed and reflect the types of tissue in which different species accumulate anthocyanins, such as fruit or petals (Jaakola et al., *Plant Physiol.* 130:729-739, 2002; Rosati et al., *Plant Mol. Biol.* 35:303-311, 1997). In particular, grasses accumulate higher levels of anthocyanins in the stem.

A number of antifreeze protein genes from *Lolium perenne* and *Festuca arundinacea* are described in International Patent Publication WO04/022700. Overwintering plants produce antifreeze proteins (AFPs) having the ability to adsorb onto the surface of ice crystals and modify their growth. AFPs may play a role in protecting the plant tissues from mechanical stress caused by ice formation (Atici and Nalbantoglu, *Phytochem.* 64:1187-1196, 2003). The expression of AFPs is induced by cold temperature, in specific plant tissues, and a system utilizing these specific promoters will be very powerful.

A number of fructosyltransferase genes from *Lolium perenne* and *Festuca arundinacea* are described in International Patent Publication WO 03/040306. Fructosyltransferases catalyze the synthesis of fructans, polymers of fructose found in a range of plant families including the Poaceae. Fructans are found in specific organs dependent on the plant species. In the grasses they are found in the stems and leaf base where expression of specific fructosyltransferases occurs (Luscher et al., *Plant Physiol.* 124:1217-1227, 2000). The promoters of these genes will be useful to drive specific expression of transgenes.

Plants produce a number of Class III plant peroxidase (POX) enzymes, and each isoenzyme has diverse expression profiles, suggesting their involvement in various physiological processes (for a review see Hiraga et al., *Plant Cell Physiol.* 42:462-468, 2001). POXs have been suggested to play a role in lignification, suberization, auxin catabolism, wound healing and defense against pathogen infection. The unique expression profile of these genes, captured by isolation of their promoters will provide a valuable tool for expression of transgenes.

SUMMARY OF THE INVENTION

Briefly, isolated polynucleotide regulatory sequences from *Lolium perenne* (perennial ryegrass), *Festuca arundinacea* (tall fescue) and *Arabidopsis thaliana* that are involved in the regulation of gene expression are disclosed, together with methods for the use of such polynucleotide regulatory regions in modifying the expression of endogenous and/or heterologous polynucleotides in transgenic plants. In particular, the present invention provides polynucleotide promoter sequences from 5' untranslated, or non-coding, regions of plant genes that initiate and regulate transcription of polynucleotides placed under their control, together with isolated polynucleotides comprising such promoter sequences.

In a first aspect, the present invention provides isolated polynucleotide sequences comprising a polynucleotide selected from the group consisting of: (a) sequences recited in SEQ ID NO: 1-17 and 38-48; (b) complements of the sequences recited in SEQ ID NO: 1-17 and 38-48; (c) reverse complements of the sequences recited in SEQ ID NO: 1-17 and 38-48; (d) reverse sequences of the sequences recited in SEQ ID NO: 1-17 and 38-48; and (e) sequences having at least 75%, 80%, 90%, 95% or 98% identity as defined herein, to a sequence of (a)-(d). Polynucleotides comprising at least a specified number of contiguous residues ("x-mers") of any of SEQ ID NO: 1-17 and 38-48, and oligonucleotide probes and primers corresponding to SEQ ID NO: 1-17 and 38-48 are also provided. All of the above polynucleotides are referred to herein as "polynucleotides of the present invention."

In another aspect, the present invention provides genetic constructs comprising a polynucleotide of the present invention, either alone, or in combination with one or more additional polynucleotides of the present invention, or in combination with one or more known polynucleotides, together with cells and target organisms comprising such constructs.

In a related aspect, the present invention provides genetic constructs comprising, in the 5'-3' direction, a polynucleotide promoter sequence of the present invention, a polynucleotide to be transcribed, and a gene termination sequence. The polynucleotide to be transcribed may comprise an open reading frame of a polynucleotide that encodes a polypeptide of interest, or it may be a non-coding, or untranslated, region of a polynucleotide of interest. The open reading frame may be orientated in either a sense or antisense direction. Preferably, the gene termination sequence is functional in a host plant. Most preferably, the gene termination sequence is that of the gene of interest, but others generally used in the art, such as the *Agrobacterium tumefaciens* nopalin synthase terminator may be usefully employed in the present invention. The genetic construct may further include a marker for the identification of transformed cells.

In a further aspect, transgenic cells comprising the genetic constructs of the present invention are provided, together with organisms, such as plants, comprising such transgenic cells, and fruits, seeds and other products, derivatives, or progeny of such plants. Propagules of the inventive transgenic plants are also included in the present invention. As used herein, the word "propagule" means any part of a plant that may be used in reproduction or propagation, sexual or asexual, including cuttings.

Plant varieties, particularly registerable plant varieties according to Plant Breeders' Rights, may be excluded from the present invention. A plant need not be considered a "plant variety" simply because it contains stably within its genome a transgene, introduced into a cell of the plant or an ancestor thereof.

In yet another aspect, methods for modifying gene expression in a target organism, such as a plant, are provided, such methods including stably incorporating into the genome of the organism a genetic construct of the present invention. In a preferred embodiment, the target organism is a plant, more preferably a monocotyledonous plant, most preferably selected from the group consisting of Lolium and Festuca species, most preferably from the group consisting of Lolium perenne and Festuca arundinacea.

In another aspect, methods for producing a target organism, such as a plant, having modified polypeptide expression are provided, such methods comprising transforming a plant cell with a genetic construct of the present invention to provide a transgenic cell, and cultivating the transgenic cell under conditions conducive to regeneration and mature plant growth.

In other aspects, methods for identifying a gene responsible for a desired function or phenotype are provided, the methods comprising transforming a plant cell with a genetic construct comprising a polynucleotide promoter sequence of the present invention operably linked to a polynucleotide to be tested; cultivating the plant cell under conditions conducive to regeneration and mature plant growth to provide a transgenic plant; and comparing the phenotype of the transgenic plant with the phenotype of non-transformed, or wild-type, plants.

The above-mentioned and additional features of the present invention and the manner of obtaining them will become apparent, and the invention will be best understood by reference to the following more detailed description. All references disclosed herein are hereby incorporated by reference in their entirety as if each was incorporated individually.

BRIEF DESCRIPTION OF THE DRAWINGS

FIGS. 1-17 show annotated versions of the promoter sequences of SEQ ID NO: 1-17, respectively. Motifs are identified by boxes, double underlining and bold font, and are described in detail below. Introns, where present, are underlined.

FIGS. 21-31 show annotated versions of the promoter sequences of SEQ ID NO: 38-48, respectively. Motifs are identified by boxes, double underlining and bold font, and are described in detail below.

DETAILED DESCRIPTION OF THE INVENTION

Figure 18:
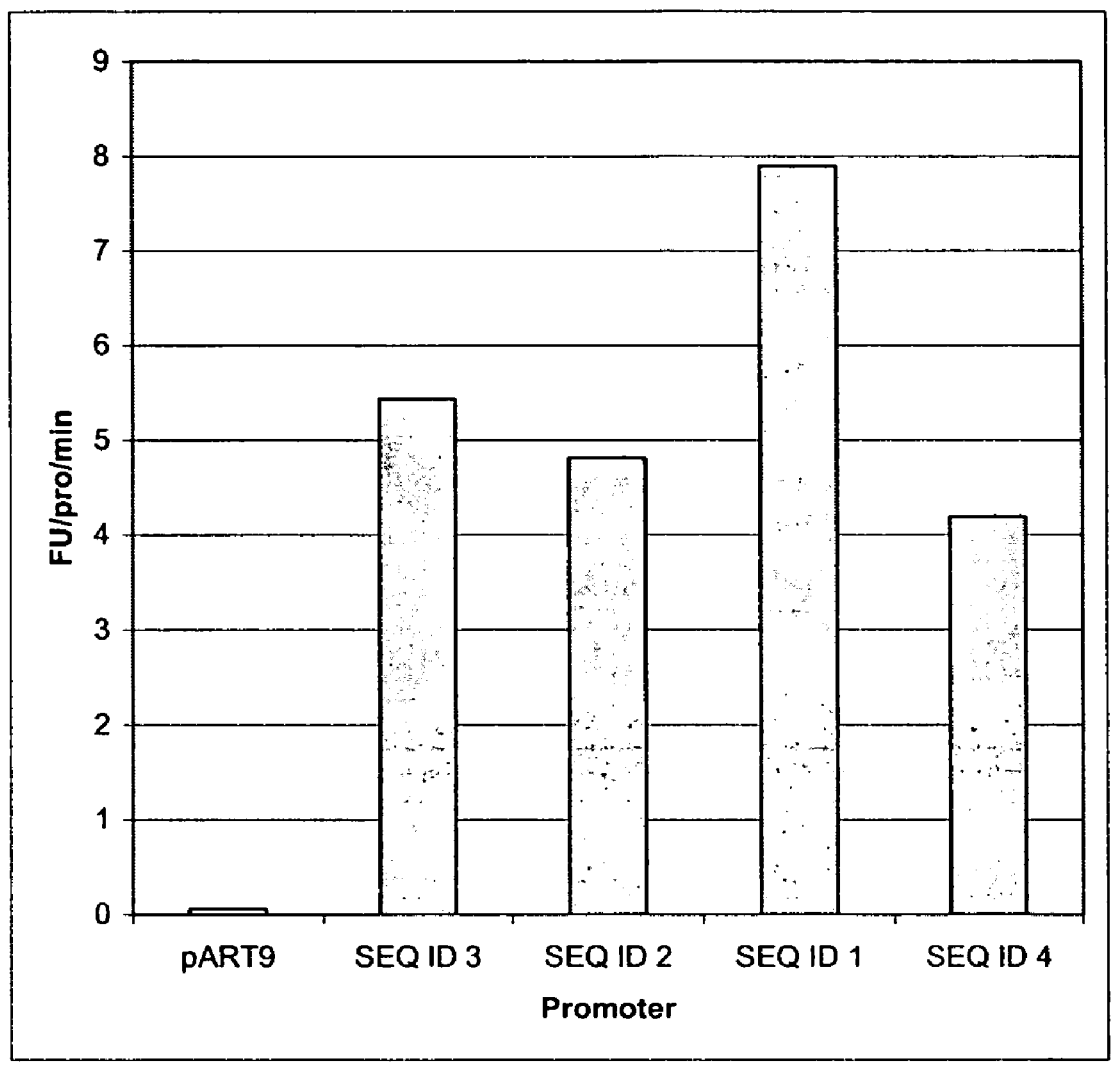
FIG. 18 shows expression levels in plant cells of the constitutive actin and tubulin promoters given in SEQ ID NO: 1-4, as determined by the level of GUS expression.

The present invention provides isolated polynucleotide regulatory regions that may be employed in the manipulation of plant phenotypes, together with isolated polynucleotides comprising such regulatory regions. More specifically, polynucleotide promoter sequences isolated from Lolium, Festuca and Arabidopsis are disclosed. As discussed above, promoters are components of the cellular "transcription apparatus" and are involved in the regulation of gene expression. Both tissue- and temporal-specific gene expression patterns are initiated and controlled by promoters during the natural development of a plant. The isolated polynucleotide promoter sequences of the present invention may thus be employed in the modification of growth and development of plants, and of cellular responses to external stimuli, such as environmental factors and disease pathogens.

Using the methods and materials of the present invention, the amount of a specific polypeptide of interest may be increased or reduced by incorporating additional copies of genes, or coding sequences, encoding the polypeptide, operably linked to an inventive promoter sequence, into the genome of a target organism, such as a plant. Similarly, an increase or decrease in the amount of the polypeptide may be obtained by transforming the target plant with antisense copies of such genes.

The polynucleotides of the present invention were isolated from plant sources, namely from Lolium perenne, Festuca arundinacea and Arabidopsis thaliana, but they may alternatively be synthesized using conventional synthesis techniques. Specifically, isolated polynucleotides of the present invention include polynucleotides comprising a sequence selected from the group consisting of: sequences identified as SEQ ID NO: 1-17 and 38-48; complements of the sequences identified as SEQ ID NO: 1-17 and 38-48; reverse complements of the sequences identified as SEQ ID NO: 1-17 and 38-48; sequences comprising at least a specified number of contiguous residues (x-mers) of any of the above-mentioned polynucleotides; extended sequences corresponding to any of the above polynucleotides; antisense sequences corresponding to any of the above polynucleotides; and variants of any of the above polynucleotides, as that term is described in this specification.

The polynucleotides of the present invention, were putatively identified by DNA similarity searches. The inventive polynucleotides have demonstrated similarity to promoters that are known to be involved in regulation of transcription and/or expression in plants. The identity of each of the inventive polynucleotides is shown below in Table 1. The cDNA sequences of SEQ ID NO: 1-15, 39-42 and 44-47 were determined to have less than 40% identity to sequences in the EMBL database using the computer algorithm BLASTN, as described below.

TABLE 1

| SEQ ID NO: | Identity | Description of Gene Function |
|---|---|---|
| 1-3 | Actin1 | Actins are molecules that play important roles in plant morphogenesis and development. The actin cytoskeleton is a key effector of signal transduction, which controls and maintains the shape of plant cells, as well as playing roles in plant morphogenesis (Vantard and Blanchoin, Curr. Opin. Plant Biol. 5: 502-506, 2002) and actin microfilaments play a role in delivery of materials required for growth to specified sites (Mathur and Hulskamp, Curr. Biol. 12: R669-676, 2002). |
| 4 | Tubulin | Microtubules play important roles in cell morphogenesis and are important for establishing and maintaining growth polarity (Mathur and Hulskamp, Curr. Biol. 12: R669-676, 2002) and other cellular processes such as cell division and cell elongation in plants (Yoshikawa et al., Plant Cell Physiol. 44: 1202-1207, 2003. |
| 5, 6 | 4CL3a | 4-Coumarate: coenzyme A ligase (4CL) plays a role in the phenylpropanoid pathway and lignin biosynthesis. 4CL is a key enzyme of general phenylpropanoid metabolism which provides the precursors for a large variety of important plant secondary products, such as lignin, flavonoids, or phytoalexins which serve important functions in plant growth and adaptation to environmental perturbations. Three isoforms have been identified with distinct substrate preference and specificities. Expression studies in angiosperms revealed a differential behavior of the three genes in various plant organs and upon external stimuli such as wounding and UV irradiation or upon challenge with fungi. One isoform is likely to participate in the biosynthetic pathway leading to flavonoids whereas the other two are probably involved in lignin formation and in the production of additional phenolic compounds other than flavonoids (Ehlting et al., Plant J. 19: 9-20, 1999). |
| 7 | COMT3 | Caffeic acid 3-O-methyltransferase (COMT) is involved in lignin biosynthesis. COMT catalyzes the conversion of caffeic acid to ferulic acid and of 5-hydroxyferulic acid to sinapic acid. Lignin is formed by polymerization of at least three different monolignols that are synthesized in a multistep pathway, each step in the pathway being catalyzed by a different enzyme. Manipulation of the number of copies of genes encoding certain enzymes in this pathway, such as COMT results in modification of the amount of lignin produced. |
| 8 | F5H | Ferulate-5-hydroxylase (F5H), also known as cytochrome P450 84A1, is involved in phenylpropanoid biosynthesis. F5H belongs to the cytochrome P450 family and the CYP84 subfamily. F5H enzymes are active in the pathways leading to the synthesis of sinapic acid esters, but has also been shown to have coniferaldehyde hydroxylase activity (Nair et al., Plant Physiol. 123: 1623-1634, 2000). In the generalized pathway for phenylpropanoid metabolism, F5H catalyzes the formation of 5-hydoxyferulate, a precursor of sinapate, and sinapate in turn is the precursor for sinapine and sinapoyl CoA in two bifurcated pathways (Chapple et al., Plant Cell 4: 1413-1424, 1992). Sinapoyl CoA has been considered as the precursor for sinapyl alcohol, which is then polymerized into syringyl (S) lignin. In addition, the CYP84 product carries out the hydroxylation of coniferaldehyde (ConAld) to 5-OH ConAld (Nair et al., Plant Physiol. 123: 1623-1634, 2000). |
| 9-11 | CHS | Chalcone Synthase (CHS) is an important enzyme in flavonoid synthesis. |
| 12 | FT | Flowering locus T (FT) and "Suppression of overexpression of CO1" (SOC1) interact with Arabidopsis CONSTANS (CO) to promote flowering in response to day length. FT and SOC1 can act independently on CO by acting within a different flowering-time pathway (Samach et al., Science 288: 1613-1616, 2000). |
| 13-15 | AFP5 | Antifreeze proteins (AFP) are involved in inhibition of ice crystal growth in plants. |
| 16, 17, 38 | DFR | Dihydroflavonal-4-reductase (DFR) belongs to the dihydroflavonol-4-reductases family and is involved in flavonoid synthesis and anthocyanidins biosynthesis. Flavonoids are secondary metabolites derived from phenylalanine and acetate metabolism that perform a variety of essential functions in higher plants. |

TABLE 1-continued

| SEQ ID NO: | Identity | Description of Gene Function |
|---|---|---|
| 39 | MYB transcription factor | The Myb family of transcription factors is a group of functionally diverse transcriptional activators found in both plants and animals that is characterized by a conserved amino-terminal DNA-binding domain containing either two (in plant species) or three (in animal species) imperfect tandem repeats of approximately 50 amino acids (Rosinski and Atchley, J. Mol. Evol. 46(1): 74-83, 1998; Stober-Grasser et al., Oncogene 7[3]: 589-596, 1992) |
| 40-42 | PER | Peroxidases are haem-containing enzymes that use hydrogen peroxide as the electron acceptor to catalyze a number of oxidative reactions. They belong to a superfamily consisting of 3 major classes. Class I contains intracellular peroxidases, Class II consists of secretory fungal peroxidases and Class III consists of the secretory plant peroxidases, which have multiple tissue-specific functions: e.g., removal of hydrogen peroxide from chloroplasts and cytosol, oxidation of toxic compounds, biosynthesis of the cell wall, defense responses towards wounding, indole-3-acetic acid (IAA) catabolism and ethylene biosynthesis. |
| 43 | 6-SFT | Sucrose-fructan 6-fructosyltransferase (6-SFT) is involved in plant fructan biosynthesis and contain the conserved signature of the glycosyl hydrolases family 32. The glycosyl hydrolases family 32 domain signature has a consensus of HYQPxxH/NxxNDPNG, where D is the active site residue (Henrissat, Biochem. J. 280: 309-316, 1991). |
| 44, 45 | PAL | Phenylalanine ammonia-lyase (PAL) catalyzes the first step in phenylpropanoid metabolism and plays a central role in the biosynthesis of phenylpropanoid compounds. |
| 46-48 | MADS box transcription factor | MADS box transcription factors play a role in regulation of transcription and interact with a conserved region of DNA known as the MADS box. All MADS box transcription factors contain a conserved DNA-binding/dimerization region, known as the MADS domain, which has been identified throughout the different kingdoms (Riechmann and Meyerowitz, Biol. Chem. 378: 1079-1101, 1997). Many of the MADS box genes isolated from plants are expressed primarily in floral meristems or floral organs, and are believed to play a role in either specifying inflorescence and floral meristem identity or in determining floral organ identity. |

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments. Anti-sense polynucleotides and techniques involving anti-sense polynucleotides are well known in the art and are described, for example, in Robinson-Benion et al., *Methods in Enzymol.* 254:363-375, 1995; and Kawasaki et al., *Artific. Organs* 20:836-848, 1996.

All of the polynucleotides described herein are isolated and purified, as those terms are commonly used in the art. Preferably, the polynucleotides are at least about 80% pure, more preferably at least about 90% pure, and most preferably at least about 99% pure.

The definition of the terms "complement", "reverse complement" and "reverse sequence", as used herein, is best illustrated by the following example. For the sequence 5' AGGACC 3', the complement, reverse complement and reverse sequence are as follows:

```
Complement              3' TCCTGG 5'
Reverse complement      3' GGTCCT 5'
Reverse sequence        5' CCAGGA 3'
```

Preferably, sequences that are complements of a specifically recited polynucleotide sequence are complementary over the entire length of the specific polynucleotide sequence.

As used herein, the term "x-mer," with reference to a specific value of "x," refers to a polynucleotide comprising at least a specified number ("x") of contiguous residues of any of the polynucleotides provided in SEQ ID NO: 1-17 and 38-48. The value of x may be from about 20 to about 600, depending upon the specific sequence.

Polynucleotides of the present invention comprehend polynucleotides comprising at least a specified number of contiguous residues (x-mers) of any of the polynucleotides identified as SEQ ID NO: 1-17 and 38-48, or their variants. According to preferred embodiments, the value of x is at least 20, more preferably at least 40, more preferably yet at least 60, and most preferably at least 80. Thus, polynucleotides of the present invention include polynucleotides comprising a 20-mer, a 40-mer, a 60-mer, an 80-mer, a 100-mer, a 120-mer, a 150-mer, a 180-mer, a 220-mer, a 250-mer, a 300-mer, 400-mer, 500-mer or 600-mer of a polynucleotide provided in SEQ ID NO: 1-17 and 38-48, or a variant of one of the polynucleotides corresponding to the polynucleotides provided in SEQ ID NO: 1-17 and 38-48.

RNA sequences, reverse sequences, complementary sequences, antisense sequences, and the like, corresponding to the polynucleotides of the present invention, may be routinely ascertained and obtained using the cDNA sequences identified as SEQ ID NO: 1-17 and 38-48.

The polynucleotides of the present invention may be isolated as described below. Alternatively, oligonucleotide probes and primers based on the sequences provided in SEQ ID NO: 1-17 and 38-48 can be synthesized as detailed below, and used to identify positive clones in DNA libraries from by means of hybridization or polymerase chain reaction (PCR) techniques. Hybridization and PCR techniques suitable for use with such oligonucleotide probes are well known in the art (see, for example, Mullis et al., *Cold Spring Harbor Symp. Quant. Biol.*, 51:263, 1987; Erlich, ed., *PCR technology*, Stockton Press: NY, 1989; Sambrook et al., eds., *Molecular cloning: a laboratory manual*, 2nd ed., CSHL Press: Cold Spring Harbor, N.Y., 1989; and Sambrook, ed., *Molecular cloning: a laboratory manual*, 3nd ed., CSHL Press: Cold Spring Harbor, N.Y., 2001). Artificial analogs of DNA hybridizing specifically to target sequences could also be employed. Positive clones may be analyzed by restriction enzyme digestion, DNA sequencing or the like.

The polynucleotides of the present invention may also, or alternatively, be synthesized using techniques that are well known in the art. The polynucleotides may be synthesized, for example, using automated oligonucleotide synthesizers (e.g., Beckman Oligo 1000M DNA Synthesizer; Beckman Coulter Ltd., Fullerton, Calif.) to obtain polynucleotide segments of up to 50 or more nucleic acids. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having, for example, 80 nucleic acids, and hybridizing that segment to a synthesized complementary 85 nucleic acid segment to produce a 5 nucleotide overhang. The next segment may then be synthesized in a similar fashion, with a 5 nucleotide overhang on the opposite strand. The "sticky" ends ensure proper ligation when the two portions are hybridized. In this way, a complete polynucleotide of the present invention may be synthesized entirely in vitro.

As used herein, the term "variant" comprehends nucleotide sequences different from the specifically identified sequences, wherein one or more nucleotides is deleted, substituted, or added. Variants may be naturally occurring allelic variants, or non-naturally occurring variants. Variant sequences preferably exhibit at least 75%, more preferably at least 80%, more preferably at least 85%, more preferably at least 90%, more preferably yet at least 95%, and most preferably at least 98% identity to a sequence of the present invention. The percentage identity is determined by aligning the two sequences to be compared as described below, determining the number of identical residues in the aligned portion, dividing that number by the total number of residues in the inventive (queried) sequence, and multiplying the result by 100.

Polynucleotides having a specified percentage identity to a polynucleotide identified in one of SEQ ID NO: 1-17 and 38-48 thus share a high degree of similarity in their primary structure. In addition to a specified percentage identity to a polynucleotide of the present invention, variant polynucleotides preferably have additional structural and/or functional features in common with a polynucleotide of the present invention. Polynucleotides having a specified degree of identity to, or capable of hybridizing to, a polynucleotide of the present invention preferably additionally have at least one of the following features: (1) they have substantially the same functional properties as a polynucleotide of SEQ ID NO: 1-17 and 3848; or (2) they contain identifiable domains in common.

Polynucleotide sequences may be aligned, and percentage of identical residues in a specified region may be determined against other polynucleotide sequences, using computer algorithms that are publicly available. Two exemplary algorithms for aligning and identifying the similarity of polynucleotide sequences are the BLASTN and FASTA algorithms. The BLASTN algorithm Version 2.2.6 [Apr.-9-2003] set to the default parameters described in the documentation and distributed with the algorithm, is preferred for use in the determination of polynucleotide variants of SEQ ID NO: 1-17 and 38-48. The use of the BLAST family of algorithms, including BLASTN, BLASTP, and BLASTX, is described in the publication of Altschul et al., *Nucleic Acids Res.* 25:3389-3402, 1997. The BLASTN software is available on the NCBI anonymous FTP server and from the National Center for Biotechnology Information (NCBI), National Library of Medicine, Building 38A, Room 8N805, Bethesda, Md. 20894, USA.

The FASTA software package is available from the University of Virginia (University of Virginia, PO Box 9025, Charlottesville, Va. 22906-9025). Version 2.0u4, February 1996, set to the default parameters described in the documentation and distributed with the algorithm, may be used in the determination of variants according to the present invention. The use of the FASTA algorithm is described in Pearson and Lipman, *Proc. Natl. Acad. Sci. USA* 85:2444-2448, 1988; and Pearson, *Methods in Enzymol.* 183:63-98, 1990.

The following running parameters are preferred for determination of alignments and similarities using BLASTN that contribute to the E values and percentage identity for polynucleotide sequences: Unix running command: blastall –p blastn –d embldb –e 10 –G 0 –E 0 –r 1 –F F –v 30 –b 30 –i queryseq –o results; the parameters are: –p Program Name [String]; –d Database [String]; –e Expectation value (E) [Real]; –G Cost to open a gap (zero invokes default behavior) [Integer]; –E Cost to extend a gap (zero invokes default behavior) [Integer]; –F low complexity filter; –r Reward for a nucleotide match (BLASTN only) [Integer]; –v Number of one-line descriptions (V) [Integer]; –b Number of alignments to show (B) [Integer]; –i Query File [File In]; and –o BLAST report Output File [File Out] Optional.

The "hits" to one or more database sequences by a queried sequence produced by BLASTN, FASTA, BLASTP or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, FASTA and BLASTP algorithms also produce "Expect" values for alignments. The Expect value (E) indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the polynucleotide sequences then have a probability of 90% of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides, with reference to each of the polynucleotides of the present invention, preferably comprise sequences having the same number or fewer base pairs than each of the polynucleotides of the present invention and producing an E value of 0.01 or less when compared to the polynucleotide of the present invention. That is, a variant polynucleotide is any sequence that has at least a 99% probability of being the same as the polynucleotide of the present invention, measured as having an E value of 0.01 or less using the BLASTN or FASTA algorithms set at parameters described above. According to a preferred embodiment, a variant polynucleotide is a sequence having the same number or fewer nucleic acids than a polynucleotide of the present invention that has at least a 99% probability of being the same as the polynucleotide of the present invention, measured as having an E value of 0.01 or less using the BLASTN or FASTA algorithms set at parameters described above.

In an alternative embodiment, variant polynucleotides are sequences that hybridize to a polynucleotide of the present invention under stringent conditions. Stringent hybridization conditions for determining complementarity include salt conditions of less than about 1 M, more usually less than about 500 mM, and preferably less than about 200 mM. Hybridization temperatures can be as low as 5° C., but are generally greater than about 22° C., more preferably greater than about 30° C., and most preferably greater than about 37° C. Longer DNA fragments may require higher hybridization temperatures for specific hybridization. Since the stringency of hybridization may be affected by other factors such as probe composition, presence of organic solvents, and extent of base mismatching, the combination of parameters is more important than the absolute measure of any one alone. An example of "stringent conditions" is prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

Polynucleotides comprising sequences that differ from the polynucleotide sequences recited in SEQ ID NO: 1-17 and 38-48, or complements, reverse complements or reverse sequences thereof, as a result of deletions and/or insertions totaling less than 10% of the total sequence length are also contemplated by and encompassed within the present invention.

In certain embodiments, variants of the inventive polynucleotides possess biological activities that are the same or similar to those of the inventive polynucleotides. Such variant polynucleotides function as promoter sequences and are thus capable of modifying gene expression in a plant.

As noted above, the inventive polynucleotide promoter sequences may be employed in genetic constructs to drive transcription and/or expression of a polynucleotide of interest. The polynucleotide of interest may be either endogenous or heterologous to an organism, for example a plant, to be transformed. The inventive genetic constructs may thus be employed to modulate levels of transcription and/or expression of a polynucleotide, for example a gene, that is present in the wild-type plant, or may be employed to provide transcription and/or expression of a DNA sequence that is not found in the wild-type plant.

In certain embodiments, the polynucleotide of interest comprises an open reading frame that encodes a target polypeptide. The open reading frame is inserted in the genetic construct in either a sense or antisense orientation, such that transformation of a target plant with the genetic construct will lead to a change in the amount of polypeptide compared to the wild-type plant. Transformation with a genetic construct comprising an open reading frame in a sense orientation will generally result in over-expression of the selected polypeptide, while transformation with a genetic construct comprising an open reading frame in an antisense orientation will generally result in reduced expression of the selected polypeptide. A population of plants transformed with a genetic construct comprising an open reading frame in either a sense or antisense orientation may be screened for increased or reduced expression of the polypeptide in question using techniques well known to those of skill in the art, and plants having the desired phenotypes may thus be isolated.

Alternatively, expression of a target polypeptide may be inhibited by inserting a portion of the open reading frame, in either sense or antisense orientation, in the genetic construct. Such portions need not be full-length but preferably comprise at least 25 and more preferably at least 50 residues of the open reading frame. A much longer portion, or even the full length DNA corresponding to the complete open reading frame, may be employed. The portion of the open reading frame does not need to be precisely the same as the endogenous sequence, provided that there is sufficient sequence similarity to achieve inhibition of the target gene. Thus a sequence derived from one species may be used to inhibit expression of a gene in a different species.

In further embodiments, the inventive genetic constructs comprise a polynucleotide including an untranslated, or non-coding, region of a gene coding for a target polypeptide, or a polynucleotide complementary to such an untranslated region. Examples of untranslated regions which may be usefully employed in such constructs include introns and 5'-untranslated leader sequences. Transformation of a target plant with such a genetic construct may lead to a reduction in the amount of the polypeptide expressed in the plant by the process of cosuppression, in a manner similar to that discussed, for example, by Napoli et al., *Plant Cell* 2:279-290, 1990 and de Carvalho Niebel et al., *Plant Cell* 7:347-358, 1995.

Alternatively, regulation of polypeptide expression can be achieved by inserting appropriate sequences or subsequences (e.g. DNA or RNA) in ribozyme constructs (McIntyre and Manners, *Transgenic Res.* 5:257-262, 1996). Ribozymes are synthetic RNA molecules that comprise a hybridizing region complementary to two regions, each of which comprises at least 5 contiguous nucleotides in a mRNA molecule encoded by one of the inventive polynucleotides. Ribozymes possess highly specific endonuclease activity, which autocatalytically cleaves the mRNA.

The polynucleotide of interest, such as a coding sequence, is operably linked to a polynucleotide promoter sequence of the present invention such that a host cell is able to transcribe an RNA from the promoter sequence linked to the polynucleotide of interest. The polynucleotide promoter sequence is generally positioned at the 5' end of the polynucleotide to be transcribed.

The inventive genetic constructs further comprise a gene termination sequence which is located 3' to the polynucleotide of interest. A variety of gene termination sequences which may be usefully employed in the genetic constructs of the present invention are well known in the art. One example of such a gene termination sequence is the 3' end of the *Agrobacterium tumefaciens* nopaline synthase gene. The gene termination sequence may be endogenous to the target plant or may be exogenous, provided the promoter is functional in the target plant. For example, the termination sequence may be from other plant species, plant viruses, bacterial plasmids and the like.

The genetic constructs of the present invention may also contain a selection marker that is effective in cells of the target organism, such as a plant, to allow for the detection of transformed cells containing the inventive construct. Such markers, which are well known in the art, typically confer resistance to one or more toxins. One example of such a marker is the nptII gene whose expression results in resistance to kanamycin or hygromycin, antibiotics which are usually toxic to plant cells at a moderate concentration (Rogers et al., in Weissbach A and H, eds. *Methods for Plant Molecular Biology*, Academic Press Inc.: San Diego, Calif., 1988). Transformed cells can thus be identified by their ability to grow in media containing the antibiotic in question. Alternatively, the presence of the desired construct in transformed cells can be determined by means of other techniques well known in the art, such as Southern and Western blots.

Techniques for operatively linking the components of the inventive genetic constructs are well known in the art and include the use of synthetic linkers containing one or more restriction endonuclease sites as described, for example, by Sambrook et al., (*Molecular cloning: a laboratory manual*, CSHL Press: Cold Spring Harbor, N.Y., 1989). The genetic construct of the present invention may be linked to a vector having at least one replication system, for example *E. coli*, whereby after each manipulation, the resulting construct can be cloned and sequenced and the correctness of the manipulation determined.

The genetic constructs of the present invention may be used to transform a variety of target organisms including, but not limited to, plants. Plants which may be transformed using the inventive constructs include both monocotyledonous angiosperms (e.g., grasses, corn, grains, oat, wheat and barley), dicotyledonous angiosperms (e.g., *Arabidopsis*, tobacco, legumes, alfalfa, oaks, eucalyptus, maple), and gymnosperms. In a preferred embodiment, the inventive genetic constructs are employed to transform monocotyledonous plants. Preferably the target plant is selected from the group consisting of *Lolium* and *Festuca* species, most preferably from the group consisting of *Lolium perenne* and *Festuca arundinacea*. Other species which may be usefully transformed with the genetic constructs of the present invention include, but are not limited to: fescues such as *Festuca californica, Festuca idahoensis, Festuca ovina, Festuca rubra, Festuca rubra, Festuca saximontana, Festuca viviparoidea, Festuca vivipara, Festuca airoides, Festuca altaica, Festuca ammobia, Festuca arizonica, Festuca arvernensis, Festuca auriculata, Festuca baffinensis, Festuca brachyphylla, Festuca brevissima, Festuca californica, Festuca calligera, Festuca campestris, Festuca dasyclada, Festuca drymeia, Festuca drymeja, Festuca earlei, Festuca edlundiae, Festuca elmeri, Festuca filiformis, Festuca groenlandica, Festuca hallii, Festuca hawaiiensis, Festuca hawiiensis, Festuca heteromalla, Festuca heterophylla, Festuca howellii, Festuca hyperborean, Festuca idahoensis, Festuca kashmiriana* Stapf, *Festuca kitaibeliana, Festuca lenensis, Festuca ligulata, Festuca minutiflora, Festuca occidentalis, Festuca paradoxa, Festuca parishii, Festuca prolifera, Festuca richardsonii, Festuca rigescens, Festuca roemeri, Festuca rubra, Festuca saximontana, Festuca sororia, Festuca subulata, Festuca subuliflora, Festuca subverticillata, Festuca thurberi, Festuca trachyphylla, Festuca valesiaca, Festuca versuta, Festuca viridula, Festuca washingtonica; Lolium* spp., such as *Lolium rigidum, Lolium arundinaceum, Lolium* X *aschersoniana, Lolium* X *festucaceum, Lolium giganteum, Lolium persicum, Lolium pratense, Lolium remotum, Lolium rigidum, Lolium temulentum*; other grasses from the Poaceae family (grasses), such as *Agrostis* spp. (bentgrass) e.g. *Agrostis stolonifera, Avena* spp. (oats) e.g. *Avena sativa, Brachypodium* spp. (brome grass), *Dactylis glomerata*, X *Festulolium braunii*, X *Festulolium fredericii*, X *Festulolium holmbergii, Hordeum* spp. (barley) e.g. *Hordeum vulgare, Oryza* spp. (rice) e.g. *Oryza sativa, Poa* spp. (bluegrass) e.g. *Poa pratensis, Saccharum* spp. (sugarcane) e.g. *Saccharum officinarum, Secale cereale, Sorghum* spp. e.g. *Sorghum bicolor, Triticum* spp. (wheat) e.g. *Triticum aestivum*, and *Zea* spp. (maize) e.g. *Zea mays*.

Techniques for stably incorporating genetic constructs into the genome of target plants are well known in the art and include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants, together with certain monocots and gymnosperms may be transformed by *Agrobacterium* Ti plasmid technology, as described, for example by Bevan, *Nucleic Acids Res.* 12:8711-8721, 1984. Targets for the introduction of the genetic constructs of the present invention include tissues, such as leaf tissue, dissociated cells, protoplasts, seeds, embryos, meristematic regions, cotyledons, hypocotyls, and the like. The most commonly used method for transforming lolium and fescue species is the biolistic method; for a review see Spangenberg et al., Biotechnology in Forage and Turf Grass Improvement, Monographs on Theoretical and Applied Genetics, 23, Springer-Verlag 1998. More recently *Agrobacterium* mediated transformation has been achieved for lolium and fescue species (Bettany et al., *Plant Cell Rep.* 21:437-444, 2003).

Once the cells are transformed, cells having the inventive genetic construct incorporated in their genome may be selected by means of a marker, such as the kanamycin resistance marker discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. For a review of regeneration from protoplasts see Folling and Olesen, *Methods Mol. Biol.* 111:183-193 (1999), and for a review of regeneration from other tissues see Spangenberg et al., Biotechnology in Forage and Turf Grass Improvement, Monographs on Theoretical and Applied Genetics, 23, Springer-Verlag 1998. Transformed plants having the desired phenotype may be selected using techniques well known in the art. The resulting transformed plants may be reproduced sexually or asexually, using methods well known in the art, to give successive generations of transgenic plants.

As discussed above, the production of RNA in target cells can be controlled by choice of the promoter sequence, or by selecting the number of functional copies or the site of integration of the polynucleotides incorporated into the genome of the target host. A target organism may be transformed with more than one genetic construct of the present invention, thereby modulating the activity of more than gene. Similarly, a genetic construct may be assembled containing more than one open reading frame coding for a polypeptide of interest or more than one untranslated region of a gene coding for such a polypeptide.

Polynucleotides of the present invention may also be used to specifically suppress gene expression by methods that operate post-transcriptionally to block the synthesis of products of targeted genes, such as RNA interference (RNAi), and quelling. For a review of techniques of gene suppression see Science, 288:1370-1372, 2000. Exemplary gene silencing methods are also provided in WO 99/49029 and WO 99/53050. Posttranscriptional gene silencing is brought about by a sequence-specific RNA degradation process which results in the rapid degradation of transcripts of sequence-related genes. Studies have provided evidence that double-stranded RNA may act as a mediator of sequence-specific gene silencing (see, e.g., review by Montgomery and Fire, Trends in Genetics, 14: 255-258, 1998). Gene constructs that produce transcripts with self-complementary regions are particularly efficient at gene silencing. A unique feature of this posttranscriptional gene silencing pathway is that silencing is not limited to the cells where it is initiated. The gene-silencing effects may be disseminated to other parts of an organism and even transmitted through the germ line to several generations.

The polynucleotides of the present invention may be employed to generate gene silencing constructs and or gene-specific self-complementary RNA sequences that can be delivered by conventional art-known methods to plant tissues, such as forage grass tissues. Within genetic constructs, sense and antisense sequences can be placed in regions flanking an intron sequence in proper splicing orientation with donor and acceptor splicing sites, such that intron sequences are removed during processing of the transcript and sense and antisense sequences, as well as splice junction sequences, bind together to form double-stranded RNA. Alternatively, spacer sequences of various lengths may be employed to separate self-complementary regions of sequence in the construct. During processing of the gene construct transcript, intron sequences are spliced-out, allowing sense and antisense sequences, as well as splice junction sequences, to bind forming double-stranded RNA. Select ribonucleases bind to and cleave the double-stranded RNA, thereby initiating the cascade of events leading to degradation of specific mRNA gene sequences, and silencing specific genes. Alternatively, rather than using a gene construct to express the self-complementary RNA sequences, the gene-specific double-stranded RNA segments are delivered to one or more targeted areas to be internalized into the cell cytoplasm to exert a gene silencing effect. Gene silencing RNA sequences comprising the polynucleotides of the present invention are useful for creating genetically modified plants with desired phenotypes as well as for characterizing genes (e.g., in high-throughput screening of sequences), and studying their functions in intact organisms.

The isolated polynucleotides of the present invention also have utility in genome mapping, in physical mapping, and in positional cloning of genes. As detailed below, the polynucleotide sequences identified as SEQ ID NO: 1-17 and 38-48, and their variants, may be used to design oligonucleotide probes and primers. Oligonucleotide probes designed using the polynucleotides of the present invention may be used to detect the presence and examine the expression patterns of genes in any organism having sufficiently similar DNA and RNA sequences in their cells using techniques that are well known in the art, such as slot blot DNA hybridization techniques. Oligonucleotide primers designed using the polynucleotides of the present invention may be used for PCR amplifications. Oligonucleotide probes and primers designed using the polynucleotides of the present invention may also be used in connection with various microarray technologies, including the microarray technology of Affymetrix (Santa Clara, Calif.).

As used herein, the term "oligonucleotide" refers to a relatively short segment of a polynucleotide sequence, generally comprising between 6 and 60 nucleotides, and comprehends both probes for use in hybridization assays and primers for use in the amplification of DNA by polymerase chain reaction.

An oligonucleotide probe or primer is described as "corresponding to" a polynucleotide of the present invention, including one of the sequences set out as SEQ ID NO: 1-17 and 38-48, or a variant, if the oligonucleotide probe or primer, or its complement, is contained within one of the sequences set out as SEQ ID NO: 1-17 and 38-48, or a variant of one of the specified sequences. Oligonucleotide probes and primers of the present invention are substantially complementary to a polynucleotide disclosed herein.

Two single stranded sequences are said to be substantially complementary when the nucleotides of one strand, optimally aligned and compared, with the appropriate nucleotide insertions and/or deletions, pair with at least 80%, preferably at least 90% to 95% and more preferably at least 98% to 100% of the nucleotides of the other strand. Alternatively, substantial complementarity exists when a first DNA strand will selectively hybridize to a second DNA strand under stringent hybridization conditions. Stringent hybridization conditions for determining complementarity include salt conditions of less than about 1 M, more usually less than about 500 mM, and preferably less than about 200 mM. Hybridization temperatures can be as low as 5° C., but are generally greater than about 22° C., more preferably greater than about 30° C., and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone.

In specific embodiments, the oligonucleotide probes and/or primers comprise at least about 6 contiguous residues, more preferably at least about 10 contiguous residues, and most preferably at least about 20 contiguous residues complementary to a polynucleotide sequence of the present invention. Probes and primers of the present invention may be from about 8 to 100 base pairs in length or, preferably from about 10 to 50 base pairs in length or, more preferably from about 15 to 40 base pairs in length. The probes can be easily selected using procedures well known in the art, taking into account DNA-DNA hybridization stringencies, annealing and melting temperatures, and potential for formation of loops and other factors, which are well known in the art. Preferred techniques for designing PCR primers are disclosed in Dieffenbach, C W and Dyksler, G S. *PCR Primer: a laboratory manual*, CSHL Press: Cold Spring Harbor, N.Y., 1995. A software program suitable for designing probes, and especially for designing PCR primers, is available from Premier Biosoft International, 3786 Corina Way, Palo Alto, Calif. 94303-4504.

A plurality of oligonucleotide probes or primers corresponding to a polynucleotide of the present invention may be provided in a kit form. Such kits generally comprise multiple DNA or oligonucleotide probes, each probe being specific for a polynucleotide sequence. Kits of the present invention may comprise one or more probes or primers corresponding to a polynucleotide of the present invention, including a polynucleotide sequence identified in SEQ ID NO: 1-17 and 38-48.

In one embodiment useful for high-throughput assays, the oligonucleotide probe kits of the present invention comprise multiple probes in an array format, wherein each probe is immobilized at a predefined, spatially addressable location on the surface of a solid substrate. Array formats which may be usefully employed in the present invention are disclosed, for example, in U.S. Pat. Nos. 5,412,087 and 5,545,451; and PCT Publication No. WO 95/00450, the disclosures of which are hereby incorporated by reference.

The following examples are offered by way of illustration and not by way of limitation.

EXAMPLE 1

Isolation of Gene Sequences from *L. perenne* and *F. arundinacea* cDNA Libraries

*L. perenne* and *F. arundinacea* cDNA expression libraries were constructed and screened as follows. Tissue was collected from *L. perenne* and *F. arundinacea* during winter and spring, and snap-frozen in liquid nitrogen. The tissues collected include those obtained from leaf blades, leaf base, pseudostem, floral stems, inflorescences, roots and stem. Total RNA was isolated from each tissue type using TRIzol Reagent (BRL Life Technologies, Gaithersburg, Md.). mRNA from each tissue type was obtained using a Poly(A) Quik mRNA isolation kit (Stratagene, La Jolla, Calif.), according to the manufacturer's specifications. cDNA expression libraries were constructed from the purified mRNA by reverse transcriptase synthesis followed by insertion of the resulting cDNA in Lambda ZAP using a ZAP Express cDNA Synthesis Kit (Stratagene, La Jolla, Calif.), according to the manufacturer's protocol. The resulting cDNA clones were packaged using a Gigapack II Packaging Extract (Stratagene, La Jolla, Calif.) employing 1 µl of sample DNA from the 5 µl ligation mix. Mass excision of the libraries was done using XL1-Blue MRF' cells and XLOLR cells (Stratagene, La Jolla, Calif.) with ExAssist helper phage (Stratagene, La Jolla, Calif.). The excised phagemids were diluted with NZY broth (Gibco BRL, Gaithersburg, Md.) and plated out onto LB-kanamycin agar plates containing 5-bromo-4-chloro-3-indolyl-beta-D-galactosidase (X-gal) and isopropylthio-beta-galactoside (IPTG). Of the colonies plated and picked for DNA preparations, the large majority contained an insert suitable for sequencing. Positive colonies were cultured in NZY broth with kanamycin and DNA was purified following standard protocols. Agarose gel at 1% was used to screen sequencing templates for chromosomal contamination. Dye terminator sequences were prepared using a Biomek 2000 robot (Beckman Coulter Inc., Fullerton, Calif.) for liquid handling and DNA amplification using a 9700 PCR machine (Perkin Elmer/Applied Biosystems, Foster City, Calif.) according to the manufacturer's protocol.

The DNA sequences for positive clones were obtained using a Perkin Elmer/Applied Biosystems Division Prism 377 sequencer. cDNA clones were sequenced from the 5' end. The determined sequences were assembled into consensus sequences using Stackpack™, version 1.2 (Electric Genetics Corporation, Cape Town, South Africa.). To identify polynucleotides of interest, these consensus sequences were compared to selected 'seed' sequences using BLAST analyses, described above.

EXAMPLE 2

Isolation of Grass Promoter Regions Using GenomeWalker Technology

The inventive promoter sequences were isolated using the following methodology.

The grass gene promoters were cloned using a GenomeWalker kit (Clontech, Palo Alto, Calif.). This is a PCR-based method, which requires two gene-specific PCR primers to be constructed for nested PCR. In brief, genomic DNA from *Lolium perenne* and *Festuca arundinacea* was isolated, purified and digested with one of four different restriction enzymes that recognize a 6-base site, leaving blunt ends. Following digestion, each pool of DNA fragments was ligated to the GenomeWalker Adaptor. Two rounds of PCR were performed with an adaptor primer and a gene-specific primer to amplify a promoter fragment. The polynucleotide fragments were cloned into the pART9 DNA vector and the insert DNA was sequenced using the methods described above. pART9 is a modified pART7 vector (Gleave, *Plant Mol. Biol.* 20:1203-1207, 1992), where the CaMV 35S promoter has been removed and replaced with a polylinker containing the following restriction enzyme sites: SstI NotI EcoRI XcmI (2 SITES), KpnI and NcoI.

The isolated promoter polynucleotide sequences were searched for cis motifs using a set of 340 specific motifs from the PLACE database (Higo et al., *Nucleic Acids Res.* 27: 297-300, 1999). Motifs were highlighted and numbered; the number and details of cis element identification is given in Table 2.

TABLE 2

Description of cis-motifs from PLACE database (Higo et al., Nucleic Acids Res. 27:297-300, 1999)

| Motif No | Motif Description | Description/ Identifier | Reference |
|---|---|---|---|
| I | AAAG | Core site for binding of Dof proteins in maize | Plant J. 17:209-214 (1999) |
| II | AATAAT/ AATAAA/ AATTAAA | Plant polyA signal | Nucleic Acids Res. 15:9627-9640 (1987) |
| III | ACACAGG/ ACACCAG/ ACACCTG/ | Novel class of bZIP transcription factors, DPBF-1 and 2 binding | Plant J. 11:1237-1251 (1997) |

TABLE 2-continued

Description of cis-motifs from PLACE database (Higo et al., Nucleic Acids Res. 27:297-300, 1999)

| Motif No | Motif Description | Description/ Identifier | Reference |
|---|---|---|---|
|  | ACACCCG/ ACACGGG/ ACACTGG/ ACACTTG | core sequence in carrot Dc3 gene promoter |  |
| IV | ATATT | Root motif TAPOX1 - found in promoters of rolD | Transgenic Res. 4:388-396 (1995) |
| V | CAAT/ CCAAT | CAAT box | Mol. Gen. Genet. 215:326-331 (1989) |
| VI | CATGTG | MYC recognition sequence necessary for expression of erd1 in dehydrated Arabidopsis | Plant J. 33:259-270 (2003) |
| VII | CCGAAA | LTRE (low temperature responsive element) in barley | Plant Mol. Bid. 38:551-564 (1998) |
| VIII | GATA | GATA box | Plant Cell 1:1147-1156 (1989) |
| IX | GGTAAA/ GAAAAA/ GGAAAA/ GGAAAT/ GAAAAT | Consensus GT-1 binding site in many light regulated genes | J. Bid. Chem. 271:32593-32598 (1996) |
| X | TGACG | ASF-1 binding site in CaMV 35S promoter - motif is found in many promoters and are involved in transcriptional activation of several genes by auxin and or salicylic acid | Plant Cell 15:2181-2191 (2003) |
| XI | TTATTT/ TATAAAT/ TATATAA/ TATTAAT | box - found in the 5' upstream region of pea | Plant Physiol. 108:1109-1117 (1995) |
| XII | ACACATG/ CAGATG/ CAGTTG | Binding site for MYC in Arabidopsis dehydration responsive gene rd22 | Plant J. 33:259-270 (2003) |
| XIII | ACGTCA/ CCGTCG | "hexamer motif" found in promoter of wheat histone genes H3 and H4. "hexamer motif" in type 1 element may play important roles in regulation of replication dependant but not replication independent expression of the wheat histone H3 gene | Plant J. 10:425-435 (1996) |
| XIV | AGAAA | One of two co-dependent regulatory elements responsible for pollen specific activation of tomato lat52 gene AGAAA and TCCACCATA are required for pollen specific expression | Plant Mol. Biol. 37:859-869 (1998) |
| XV | CAAATG/ CAAGT/ CATTTG/ CAACTG/ | E-box of napA storage protein gene of Brassica napus | Planta 199:515-519 (1996) |

TABLE 2-continued

Description of cis-motifs from PLACE database (Higo et al., Nucleic Acids Res. 27:297-300, 1999)

| Motif No | Motif Description | Description/ Identifier | Reference |
|---|---|---|---|
| | CATCTG/ CAGCTG/ CAGGTG | | |
| XVI | CAACA/ CACCTG | Binding consensus sequence of Arabidopsis transcription factor RAV1. | Nucleic Acids Res. 27:470-478 (1999) |
| XVII | CCAACC | Core of consensus maize P (myb homolog) binding site | Cell 76:543-553 (1994) |
| XVIII | CCGAC | Core of low temperature response element (LTRE) of cor15a gene in Arabidopsis | Plant Mol. Biol. 24:701-713 (1994) |
| XIX | CGACG | CGACG element found in the GC rich regions of the rice Amy3D and Amy3E amylase genes. May function as a coupling element for the G-box element | Plant Mol. Biol. 36:331-341 (1998) |
| XX | CTCCCAC | Box C in pea asparagine synthase (ASI) gene | Plant J. 12:1021-1234 (1997) |
| XXI | TACACAT | Sequence found in 5' upstream region of napin gene in Brassica napus. Binds nuclear protein in crude extracts from developing B. napus seeds | Eur. J. Biochem. 197:741-746 (1991) |
| XXII | TGCAAAAT/ TGAAAAAG/ TGTAAAGT | Present upstream of the promoter from the B-hordein gene of barley and the low molecular weight genes of wheat | Plant Cell 2:1171-1180 (1990) |
| XXIII | TGGTCCCAC | "Site lib" of rice PCNA (proliferating cell nuclear antigen) gene. Binding site for two nuclear proteins PCF1 and PCF2. | Plant J. 7:877-886 (1995) |
| XXIV | TGTCTC | ARF binding site found in the promoters of primary/early auxin response genes of Arabidopsis thaliana. | Plant J. 19:309-319 (1999) |
| XXV | TTGACC | "WA box" One of the W boxes found in the Parsley WRKY1 gene promoter | Plant Cell 13:1527-1540 (2001) |
| XXVI | TTTTTTTTT | "T-box" Motif found in SAR or MAR | Int. Rev. Cyto. 119: 57-96 (1989) |
| XXVII | AACGTGT | Promoter regions of the extA extensin gene from Brassica napus control activation in response to wounding and tensile stress | Plant Mol. Biol. 37:675-687 (1998) |

TABLE 2-continued

Description of cis-motifs from PLACE database (Higo et al., Nucleic Acids Res. 27:297-300, 1999)

| Motif No | Motif Description | Description/ Identifier | Reference |
| --- | --- | --- | --- |
| XXVIII | CAAACAC | Conserved in many storage protein gene promoters. May be important for high activity of the napA promoter | Planta 199:515-519 (1996) |
| XXIX | CTGTTG/ CGGTTA/ CAGTTA/ CCGTTG/ CAATTG/ CGGTTG/ CTGTTA | Binding site for all animal MYB and at least two plant MYB proteins ATMYB1 and ATMYB2 | EMBO J. 14:1773 (1995) |
| XXX | ATAGAA | "Box II" found in the tobacco plastid atpB gene promoter. Important for activity of NCII promoter | Plant Cell 11:1799-1810 (1999) |
| XXXI | CACGTG | "G-box" Binding site of Arabidopsis GBF4 | Trends in Biochem. 20:506-510 (1995) |
| XXXII | CATATG | Sequence found in NDE element in soya bean SAUR 15A gene promoter. Involved in auxin responsiveness | Plant Sci. 126:193-201 |
| XXXIII | CCTTTT | Pyrimidine box found in rice alpha-amylase gene. Gibberellin response cis element of GARE and pyrimidine box are partially involved in sugar repression; | FEBS Lett. 423:81-85 (1998) |
| XXXIV | TAACTG | Binding site for ATMYB2, and Arabidopsis MYB homolog. ATMYB2 is involved in regulation of genes that are responsive to water stress in Arabidopsis thaliana | Plant Cell 5:1529-1539 (1993) |
| XXXV | TACGTA | "A-box" high protein affinity ACGT element involved in bZIP protein binding specificity | Foster et al., FASEB J. 8:192-200 (1994) |
| XXXVI | AGCGGG | "BS1" found in Eucalyptus gunnii Cinnamoyl CoA Reductase (CCR) gene promoter; nuclear protein binding site; required for vascular expression | Plant J. 23:663-676 (2000) |
| XXXVII | CCGTCC | Box A; One of three putative cis-acting elements of phenylalanine ammonia lyase (PAL) genes in parsley. | Proc. Natl. Acad. Sci. USA 92:5905-5909 (1995) |
| XXXVIII | TGTGGTTT | MYB recognition site found in the promoters of the dehydration | Plant Cell 15:63-78 (2003) |

TABLE 2-continued

Description of cis-motifs from PLACE database (Higo et al., Nucleic Acids Res. 27:297-300, 1999)

| Motif No | Motif Description | Description/ Identifier | Reference |
|---|---|---|---|
| | | responsive gene rd22 and many other genes in *Arabidopsis thaliana* | |
| XXXIX | AACCCA | SEF3 binding site | Plant Cell 1:623-631 (1989) |
| XL | CAAGAGGATC/ (SEQ ID NO: 67) CAAAAAGATC/ (SEQ ID NO: 68) CAACCTAATC/ (SEQ ID NO: 69) CAAGAGCATC/ (SEQ ID NO: 70) CAAAATCATC/ (SEQ ID NO: 71) CAACTAAATC (SEQ ID NO: 72) | Region necessary for circadian expression of tomato LHc gene | Plant Mol. Bid. 38:655-662 (1998) |
| XLI | GGATA | Core motif of MybSt1. This motif is distinct from the plant Myb binding domain described so far | EMBO J. 13:5383-5392 (1994) |
| XLII | TGCAGG | 3' intron-exon splice junctions; Plant intron lower sequence | Nucleic Acids Res. 14:9549-9559 (1986) |
| XLIII ACTTTA | NtBBF1 binding site in | Plant Cell 11:323-333 | |
| | | *Agrobacterium rhizogenes* rolB gene; Required for tissue specific expression and auxin induction | (1999) |
| XLIV | ATGGTA | "S1F box" conserved both in spinach RPS1 and RPL21 genes encoding the plastid ribosomal protein S1 and L21. Negative element, may play a role in down regulating RPS1 and RPL21 promoter activity | J Bid. Chem. 267: 23515-23519 (1992) |
| XLV | ATTTTTA/ ATTTTTG/ GTTTTTA/ GTTTTTG | "SEF4" binding site in Soya bean | Plant Cell 1:623-631 (1989) |
| XLVI | AACGTT | "T-box" high protein affinity ACGT element involved in bZIP protein binding specificity | Foster et al., FASEB J. 8:192-200 (1994) |
| XLVII | AATTCAAA/ ATTTCAAA | ERE (ethylene responsive element) of tomato E4 and carnation GST1 genes | Proc. Natl. Acad. Sci. USA 91:8925-8929 (1994) |
| XLVIII | CACCTACC/ CACCAAAC/ | Plant MYB binding site. Consensus sequence related to | EMBO J. 13:128-137 (1994), Plant Cell |

TABLE 2-continued

Description of cis-motifs from PLACE database (Higo et al., Nucleic Acids Res. 27:297-300, 1999)

| Motif No | Motif Description | Description/ Identifier | Reference |
|---|---|---|---|
| | AACCTAAC | box in promoters of phenyl-propanoid biosynthetic genes such as PAL, CHS CHI, DFR, CL etc | 10:135-154 (1998) |
| XLIX | CGGATA | "Rebeta" found in *Lemna gibba* Lhcb21 gene promoter. Required for phytochrome regulation | Plant Cell 8:31-41 (1996) |
| L | GATAA | "I-box" conserved sequence upstream of light regulated genes; | Annu. Rev. Plant Physiol. Plant Mol. Biol. 46:445-474 (1995) |
| LI | TACTATT | One of SPBF binding site | Plant Mol. Biol. 18:97-108 (1992) |
| LII | CCTCACCTACC Box L; One of three putative cis | | Proc. Natl. Acad. Sci. |
| | | acting elements (boxes P, A and L) of phenylalanine ammonia lyase (PAL) genes in parsley | USA 92:5905-5909 (1995) |
| LIII | CGAACAC | Core of "(CA)n element" in storage protein genes in *Brassica napus* embryo and endosperm specific transcription of napin gene; activator and repressor | Plant Mol. Biol. 32:1019-1027 (1996) |
| LIV | TACGTGTC | "ABRE motif A" found in the promoter of the rice Osem gene | Proc. Natl. Acad. Sci. USA 96:15348-15353 (1999), Plant J. 7:913-925 (1995) |
| LV | TAACAAA | Central element of gibberellin (GA) response complex (GARC) in high-pI alpha-amylase gene in barley; Similar to c-myb and -myb consensus binding site | Plant Cell 7:1879-1891 (1995), FEBS Lett. 423:81-85 (1998) |
| LVI | AATCCAA | rbcS general consensus sequence | EMBO J. 9:1717-1726 (1990) |
| LVII | GGTTAA | Critical for GT-1 binding to box II of rbcS | EMBO J. 7:4035-4044 (1988), J. Bio. Chem. 271:32593-32598 (1996) |
| LVIII | CCACGTGG | The cis-regulatory element CCACGTGG is involved in ABA and water-stress responses of the maize gene rab28. | Plant Mol. Biol. 21:259-266 (1993) |
| LIX | ATATTTATA | "SEF1 (soybean embryo factor | Plant Cell 1:623-631 |

TABLE 2-continued

Description of cis-motifs from PLACE database (Higo et al., Nucleic Acids Res. 27:297-300, 1999)

| Motif No | Motif Description | Description/ Identifier | Reference |
|---|---|---|---|
| | | 1)" binding motif; Nuclear factors interact with a soybean beta-conglycinin enhancer. | (1989) |
| LX | AACAAAC | Core of AACA motifs found in rice glutelin genes, involved in controlling the endosperm-specific expression | Plant J. 23:415-421 (2000) |
| LXI | AACCAA | "REalpha" found in *Lemna gibba* Lhcb21 gene promoter; Binding site of proteins of whole-cell extracts | Plant Cell 8:31-41 (1996) |
| LXII | AGGTCA | "Q(quantitative)-element" in maize ZM13 gene promoter; involved in expression enhancing activity | Plant Mol. Biol. 38:663-669 (1998) |
| LXIII | AAAAATCT | CCA1 binding site; CCA1 protein (myb-related transcription factor) interact with two imperfect repeats of AAMAATCT in Lhcb1*3 gene of *Arabidopsis thaliana*; related to regulation by phytochrome | Plant Cell 9:491-507 (1997) |
| LXIV | CTAACAC | Core of "(CA)n element" in storage protein genes in *Brassica napus* ; promoter elements required for embryo and endosperm-specific transcription | Plant Mol. Biol. 32:1019-1027 (1996) |
| LXV | TTTGACT | WB box found in the Parsley WRKY1 gene promoter; required for elicitor responsiveness; WRKY transcriptional factor plays an important role in the regulation of early defense-response genes | EMBO J. 18:4689-4699; Trends Plant Sci. 5:199-206, 2002 |
| LXVI | CATGCATG | RY repeat motif; CATGCATG; quantitative seed expression; the conservative RY repeat CATGCATG within the legumin box is essential for tissue-specific expression of a legumin gene. | Nucleic Acids Res. 16:371 (1988); Plant J. 2:233-239 (1992) |
| LXVII | TAACAGA | Gibberellin-responsive element (GARE) found in the promoter region of a cysteine proteinase (REP-I) gene in rice | Plant J. 34:636-645 (2003) |

EXAMPLE 3

Determination of Promoter Activity by Transient Expression in Zinnia Plant Cells The promoter activity of the polynucleotide sequences of the present invention in Zinnia plant cells was determined as follows, according to the methods described by Fukuda and Komamine, Plant Physiol. 65:57-60, 1980. Promoter sequences were cloned upstream of a reporter gene sequence, either the GUS (beta-D-glucuronidase gene from Escherichia coli) gene or the EGFP (modified green fluorescent protein) gene.

Isolation and Culture of Zinnia elegans Mesophyll Cells in Tracheary Element (TE) Inducing (FKH) and Non-Inducing (FK) Medium The primary pair of leaves from Zinnia seedlings was harvested from 120 plants. Leaves were sterilized in 500 ml of 0.175% sodium hypochlorite solution for 15 minutes. Leaves were then rinsed three times in 500 ml of sterile water. Using 20-25 leaves in 50 ml of grinding buffer at a time, leaves were ground using a homogenizer at 8,000 rpm for 30 seconds. Cells were filtered through a 40 μm nylon mesh before pelleting by centrifuging at 200×g for 2 minutes at 20° C. The pellet was washed once more using an equal volume of grinding buffer. The pellet was re-suspended in 30 ml of FK medium or 30 ml of FKH medium, respectively. The cells were then cultured in the dark in 6-well plates, on a rotary shaker, set at 120 rpm and 23° C.

Isolation of Zinnia elegans Protoplasts from Leaves or Mesophyll Cells Cultured Overnight to Three Days in FK Medium and FKH Medium Sterile Zinnia elegans primary leaves (6-8 in number) were cut in slivers of 1 mm and placed in 15 ml of cell wall digesting enzyme mix (1% Cellulase Onozuka R-10 and 0.2% pectolyase Y23 in Protoplast isolation buffer). Mesophyll cells cultured in FK medium (40 ml) or FKH medium (40 ml) were pelleted by centrifuging at 200×g for 2 minutes at 20° C. Each pellet was re-suspended in 20 ml of sterile Protoplast isolation buffer containing 200 mg Cellulase Onozuka R-10 and 40 mg Pectolyase Y23. The protoplasts were isolated by incubating the cell suspensions in CellStar culture plates for 2-4 hours on a rotary shaker set at ~70 rpm at 23° C. for an hour, then without shaking. Protoplasts were pelleted by centrifuging the contents of the plates at 200×g for 2 minutes. Each of the pellets was re-suspended in 20 ml of 24% sucrose solution.

Transfection of Zinnia elegans Protoplasts

Zinnia protoplasts in 24% sucrose solution were overlaid with 1 ml of W5 solution (154 mM $MgCl_2$, 125 mM $CaCl_2$, 5 mM KCl, 5 mM glucose, pH 5.8-6) and centrifuged at 70×g for 10 minutes at 20° C. with brakes off. Floating protoplasts were harvested and resuspended in 10 ml of W5 solution. Protoplasts were pelleted by centrifuging at 70×g for 10 minutes at 20° C. Protoplasts were resuspended in MaMg medium (density=~5×10$^6$ protoplasts/ml) and aliquoted into individual 15 ml tubes (200 μl: 1.5×10$^6$ protoplasts). Then 8 μg DNA (of each construct) and 50 μg Salmon Testes DNA was added to the protoplast suspension, mixed, and incubated for 5 minutes at 20° C. PEG solution (200 μl at 40%) was added to each aliquot of protoplasts, mixed and incubated for 20 minutes at 20° C. Following this, 5 ml of K3/0.4M sucrose (Bilang et al., Plant Molecular Biology Manual A1:1-16, 1994) was added to each aliquot of leaf-derived transfected protoplasts or transfected protoplasts from mesophyll cells cultured in FK medium, and mixed. Similarly, 5 ml of K3/0.4M sucrose+0.1 ppm NAA+0.2 ppm BA was added to each aliquot of transfected protoplasts from mesophyll cells cultured in FKH medium and mixed. The transfected protoplast suspensions were incubated overnight at 23° C. in the dark.

Harvesting of Transfected Zinnia elegans Protoplasts and Reporter Gene Analysis

Transfected Zinnia protoplast suspensions prepared as described above were individually harvested by adding 9.5 ml of W5 solution, mixing the contents of each tube, and centrifuging at 70×g for 10 minutes at 20° C. For analysis of GUS expression, the protoplast suspensions were transferred into sterile microtubes and pelleted by centrifugation at 2,000 rpm for 2 min at 20° C. The protoplast pellet was assayed for GUS reporter gene expression as described by Jefferson, Plant Mol. Biol. Rep. 5:387-405 (1987). GUS (MUG, 4-methyl-umbelliferyl-glucuronide) assays were performed using a Wallac (Turku, Finland) Victor$^2$ 1420 Multilabel Counter. Umbelliferone was detected using a 355 nm excitation filter and a 460 nm emission filter for 1 second.

For fluorescent protein (FP) reporter gene expression, the protoplast pellet was resuspended in 250 μl of W5 solution. The cell suspension was then transferred to a flow cytometer for injection and analysis. An argon laser at a wavelength of 488 nm was used to excite fluorescent proteins. Emission from EGFP was measured at 489 nm and RedFP (DsRed Express) at 579 nm.

EXAMPLE 4

Determination of Promoter Activity by Transient Expression in Lolium multiflorum Cells The promoter activity of the polynucleotide sequences of the present invention in Lolium multiflorum cells was determined as follows Isolation of Protoplasts from Lolium multiflorum The leaves of 10-day old Lolium multiflorum seedlings were harvested, leaves cut into 5 mm strips and transferred to Petri dishes, 2 g per dish. To each dish, 20 ml of enzyme solution (0.6 M mannitol, 10 mM MES pH 5.7, 1 mM$CaCl_2$, 5 mM 2-mercaptoethanol, 0.1% BSA, 2% Cellulase, 0.4% Pectinase) was added, sealed with parafilm and incubated in the dark on a rotary shaker overnight.

The protoplasts were released from digested ryegrass by shaking on rotary shaker at 80 rpm for 5 minutes. The protoplast solution was then filtered through a 40 uM strainer into 50 ml tubes. The supernatant was centrifuged at 70×g, 20° C. for 2 minutes to pellet the protoplasts before discarding the supernatant. The protoplasts were washed twice in 40 ml of wash solution (0.6 M mannitol, 4 mM MES, 20 mM KCl pH 5.7) and resuspended in 25 μl of wash solution. The protoplast solution was diluted with MaMg medium to a final concentration of 1×10$^6$ protoplasts per 100 μl.

Transfection of Protoplasts from Lolium multiflorum

A 200 μl aliquot of protoplasts was added to 8 μg DNA (of each construct) and 50 μg Salmon Sperm carrier DNA, mixed and incubated for 5 minutes at 20° C. 300 μl of a 50% PEG solution was then added to the protoplast sample and incubated at 22° C. for 20 minutes. W5 solution was then added to 15 ml before mixing and centrifugation at 100×g for 10 minutes, 22° C. The protoplast pellet was resuspended in 3 ml of K3 solution (1× Murashige and Skoog salt and vitamins, 0.55 mM myo-inositol, 1.66 mM xylose, 29.6 μM Thiamin-HCl, 8.12 μM Nicotinic acid, 4.86 μM Pyridoxin-HCl, 0.4 mM sucrose, pH 5.6) and left for 16 hours, 23° C., in the dark. W5 solution was then added to 15 ml, the protoplasts pelleted by centrifugation at 100×g, 10 min, 22° C., and the protoplasts re-suspended in 250 μl of W5 solution ready for flow analysis. The cell suspension was transferred to a flow cytometer for injection and analysis. An argon laser at a wavelength of 488 nm was used to excite fluorescent proteins. Emission from EGFP was measured at 489 nm and RedFP (DsRed Express) at 579 nm.

EXAMPLE 5

Determination of Promoter Activity and Specificity by Expression Analysis in Whole Plants The promoter activity of the polynucleotide sequences of the present invention in whole plants was determined as follows.

To test the function of grass promoters in plants, *Arabidopsis thaliana* was transformed with constructs containing the reporter gene for β-D-glucuronidase (GUS) operably linked to the grass promoter in the pART9 vector described above. Constructs lacking a promoter were used as a negative control. The constructs were introduced into *Arabidopsis* via *Agrobacterium*-mediated transformation.

Agrobacterium tumefaciens Transformation

Agrobacterium tumefaciens strain GV3101 was transformed with these constructs using electroporation as follows. Electrocompetent *A. tumefaciens* cells were prepared according to the method of Walkerpeach and Velten, *Plant Mol. Biol. Man.* B1:1-19, 1994. Construct DNA (4 ng) was added to 40 μl competent *A. tumefaciens* GV3101 cells and electroporation was carried out using a BTX Electro Cell Manipulator 600 at the following settings: Mode: T 2.5 kV Resistance high voltage (HV), Set Capacitance: C (not used in HV mode), Set Resistance: R R5 (129 Ohm), Set charging voltage: S 1.44 kV, Desired field strength: 14.4 kV/cm and Desired pulse strength: t 5.0 msec. 400 μl YEP liquid media (20 g/l yeast, 20 g/l peptone and 10 g/l sodium chloride) was added to the cuvette and left to recover for one hour at room temperature. Transformed bacteria in YEP medium were spread out on solid YEP medium containing 50 mg/l kanamycin and 50 mg/l rifampicin and incubated at 29° C. for two days to allow colony growth.

Confirmation of Transformation of Constructs into *A. tumefaciens*

To confirm that the constructs were transformed into *A. tumefaciens*, DNA from the *A. tumefaciens* colonies from the YEP plates was isolated using standard protocols and amplified using polymerase chain reaction (PCR) with primers designed to the promoter sequence. PCR reactions were set up following standard protocols and 30 PCR cycles were done with extension temperature of 72° C.

Transformation of *A. thaliana* with Transformed *A. tumefaciens*

The optical density of the *A. tumefaciens* bacterial culture was adjusted to 0.7 with infiltration medium (5% sucrose, 0.05% Silwett L-77 surfactant). *A. thaliana* cv. Columbia plants (6 punnets per construct and 10-12 plants per punnet) were pruned by removing secondary bolts. Pruned *A. thaliana* plants in punnets were dipped into infiltration solution and moved back and forth for 5 seconds. Punnets were put on their side to allow excess infiltration medium to drain, covered with a top tray and wrapped in plastic wrap to maintain humidity. Plants were placed in a growth room at ambient conditions for 24 hours. After this period, the top tray and plastic wrap were removed and plants were set upright until siliques formed.

Seeds were harvested and sterilized with a 5% sodium hypochlorite solution to destroy any residual *A. tumefaciens* bacteria and fungal contamination. Under sterile conditions, 100 μl seeds from the transformed *A. thaliana* plants were placed into an Eppendorf tube. One ml sterile water was added and the seeds left to imbibe the water for no longer than an hour. The water was removed by centrifugation, 1 ml 70% ethanol added to the seeds and gently mixed. This step was not allowed to last longer than one minute. The ethanol was removed by centrifugation. 1 ml 5% sodium hypochlorite solution was added to the seeds and gently mixed for up to 5 min. The sodium hypochlorite solution was removed by centrifugation and the seeds washed with sterile water for 1 min. The washing step was repeated three more times with centrifugation. Seeds were finally resuspended in sterile water. 500 μl of seeds in solution were pipetted onto half-strength Murashige and Skoog medium (MS; Gibco BRL) agar plates containing 50 mg/l kanamycin and 250 mg/l timentin, and spread evenly with a flamed wire-loop. The Petri dishes were placed in a refrigerator for 3 days to allow the seeds to stratify. Thereafter the plates were placed in the growth room and grown under lights at 22° C. with a 14 hour photoperiod until germination. Putative transformed seedlings were selected as those growing on the antibiotic-containing medium, with large, healthy-looking dark green leaves and a strong root system. These transgenic plants were removed and placed into soil culture at 22° C. with a 12 hour photoperiod.

Staining of Plant Tissues

Tissue was taken from the flower, leaf, stem and root of *A. thaliana* transformed with the constructs and stained histochemically to determine the expression of the GUS gene under control of the grass promoters. The GUS staining protocol is described by Campisi et al., *Plant J.* 17:699-707, 1999.

*A. thaliana* flower, leaf, stem and root tissues were immersed in staining solution (50 mM $NaPO_4$ pH 7.2; 0.5% Triton X-100; 1 mM X Glucuronide sodium salt (Gibco BRL)) for immunochemical staining. Vacuum was applied twice for 5 min to infiltrate the tissue with the staining solution. The tissue was left in the staining solution for 1 day (with agitation) at 37° C. for color development, and then destained in 70% ethanol for 24 hours at 37° C. (with agitation). The tissues were examined for blue GUS staining using a light microscope and photographed.

EXAMPLE 6

Constitutive Gene Promoters from *Festuca arundinacea*

*F. arundinacea* actin and tubulin cDNA sequences were identified using BLAST searches against homologous plant sequences. The most abundant actin and tubulin genes were identified by selecting the consensus sequence with the greatest number of EST members. Promoter polynucleotides were isolated using the GenomeWalker technique described above in Example 2 with primers designed to the 5' UTR of the actin and tubulin cDNAs (Table 3; SEQ ID NO: 18 and 19). Three *F. arundinacea* actin promoter polynucleotides (SEQ ID NO: 1-3) and one tubulin promoter (SEQ ID NO: 4) were cloned and sequenced. The promoter polynucleotides were analyzed for cis motifs using a set of 340 specific motifs from the PLACE database (Higo et al., *Nucleic Acids Res.* 27: 297-300, 1999). Motifs were highlighted and numbered; the number and details of cis element identification is given in Table 2 above. The motifs identified in the actin promoter sequences (SEQ ID NO: 1-3) are shown in FIGS. 1 to 3, and the motifs in the tubulin promoter sequence (SEQ ID NO: 4) are shown in FIG. 4.

The promoter sequences were cloned with the GUS reporter gene as described above in Example 3 and tested for activity in cell-based assays by transient transfection of FK cells. As shown in FIG. 18, the actin promoter of SEQ ID NO: 1 exhibited the greatest activity (highest expression levels) in this assay. The actin promoter (SEQ ID NO: 1) and the tubulin promoter (SEQ ID NO: 4) with GUS reporter were then transformed into *Arabidopsis thaliana* to test for tissue-specific expression, as described in Example 5. The presence of the correct promoter in transgenic plants was tested using the primers given in SEQ ID NO: 18 (actin promoter) and SEQ ID NO: 20 (tubulin promoter).

TABLE 3

Constitutive Actin and Tubulin promoters

| SEQ ID NO: | Promoter fragment | SEQ ID NO: Gene Specific Primer 1 | SEQ ID NO: Gene Specific Primer 2 |
|---|---|---|---|
| 1 | Actin 1 | 18 | 19 |
| 2 | Actin 2 | 18 | 19 |
| 3 | Actin 3 | 18 | 19 |
| 4 | Tubulin | 20 | 21 |

EXAMPLE 7

Vascular Specific *Lolium perenne* and *Festuca arundinacea* Promoters

*F. arundinacea* 4-coumarate-CoA ligase 3 (4CL3), *L. perenne* caffeic acid O-methyltransferase (COMT3), *L. perenne* phenylalanine ammonia-lyase (PAL) and *F. arundinacea* ferulate-5-hydroxylase (F5H) cDNA sequences were identified using BLAST searches against homologous plant sequences. Promoter polynucleotides were isolated using the GenomeWalker technique, described above, with gene specific primers designed to the 5' UTR of these lignin gene cDNAs. The gene specific primer sequences are given in SEQ ID NO: 22 and 23 (4CL3 promoters), SEQ ID NO: 24 and 25 (COMT3), SEQ ID NO: 26 and 27 (F5H), and SEQ ID NO: 44 and 45 (PAL). Two 4CL3 promoter fragments, one COMT3 promoter fragment, one F5H promoter and two PAL fragments were isolated, cloned and sequenced. The determined sequences are given in SEQ ID NO: 5-8, 44 and 45, respectively. These polynucleotides were analyzed for cis motifs using the PLACE database (see Table 2) and the identified motifs are shown in FIGS. 5-8, 27 and 28, respectively.

TABLE 4

Vascular-specific Promoters

| SEQ ID NO: | Promoter fragment | SEQ ID NO: Gene Specific Primer 1 | SEQ ID NO: Gene Specific Primer 2 |
|---|---|---|---|
| 5 | 4CL3 | 22 | 23 |
| 6 | 4CL3 | 22 | 23 |
| 7 | COMT3 | 24 | 25 |
| 8 | F5H | 26 | 27 |

TABLE 4-continued

Vascular-specific Promoters

| SEQ ID NO: | Promoter fragment | SEQ ID NO: Gene Specific Primer 1 | SEQ ID NO: Gene Specific Primer 2 |
|---|---|---|---|
| 44 | PAL1 | 59 | 60 |
| 45 | PAL2 | 59 | 60 |

Figure 19:
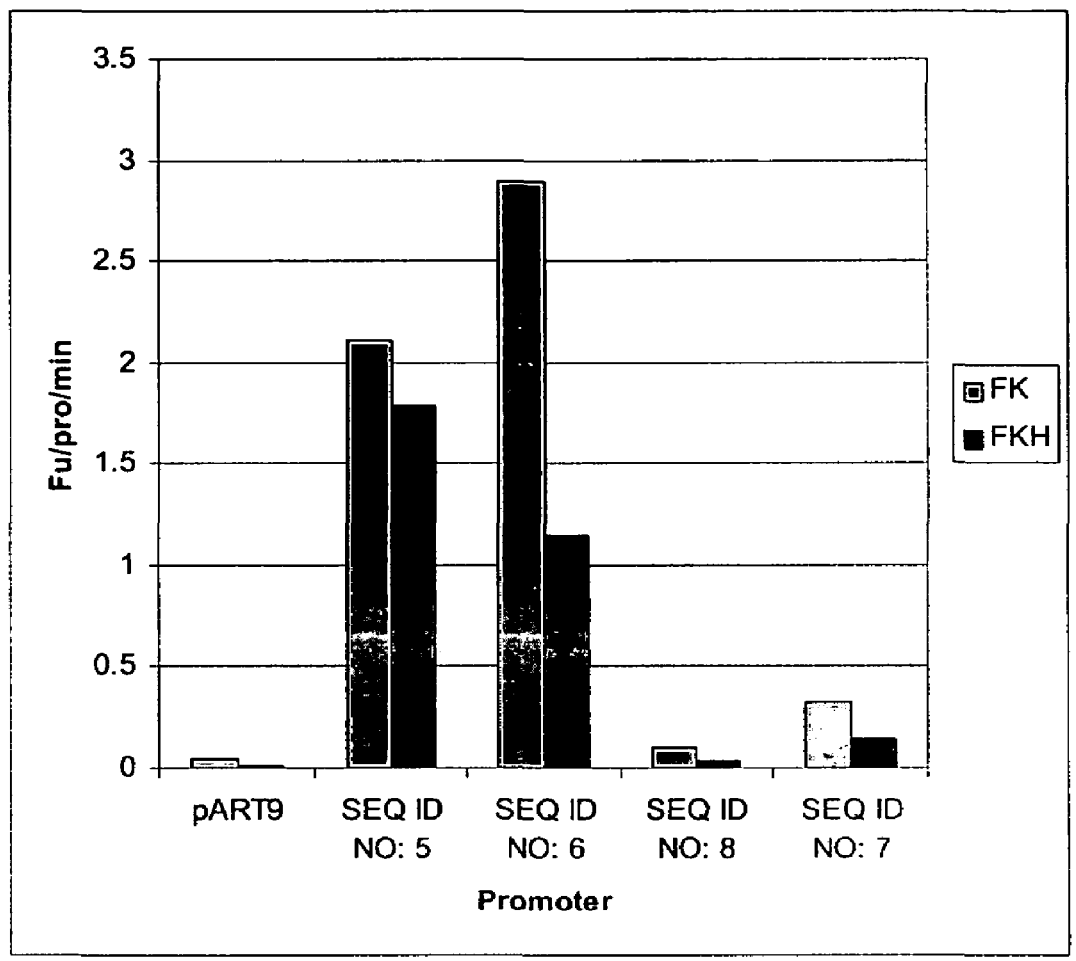
FIG. 19 shows expression levels of the lignin promoters of SEQ ID NO: 5-8 in plant cells, as determined by the level of GUS expression.

The promoter sequences were cloned with the GUS reporter gene as described in Example 3 and tested for activity in cell-based assays by transient transfection of FK and FKH cells. FIG. 19 shows the activity of the 4CL3 (SEQ ID NO: 5, 6), COMT3 (SEQ ID NO: 7) and F5H (SEQ ID NO: 8) promoters. All promoters showed activity above the background negative control. The 4CL3 fragments had the highest activity, with SEQ ID NO: 5 showing highest activity in FKH cells, and SEQ ID NO: 6 showing highest activity in FK cells.

The promoter sequences were cloned with the EGFP reporter gene and tested for activity in the *Lolium* assay system described in Example 4. Three MYB transcription factors (MYB3, MYB17 and MYB19), that potentially play a role in lignin biosynthesis by the activation or repression of lignin biosynthesis genes, were previously isolated from *Lolium perenne*. When transformed into plant cells, the grass promoters disclosed herein will drive basal expression of EGFP protein. Binding of a transcription factor to the promoter, causing enhancement or repression of gene expression, can be measured by changes in the levels of EGFP (fluorescence).

The three grass MYB constructs were co-transfected into *Lolium multiflorum* protoplasts, with the individual lignin promoter::EGFP constructs, as described in Example 4. A vector containing Red Fluorescent protein (under the control of a pine ubiquitin promoter) was used as a co-transfection marker to determine transfection efficiency. The percentage of transfected protoplasts expressing EGFP (% Green) was used to determine EGFP levels and therefore transcription. Transfections without the MYB constructs were used as basal level controls. A % Green reading greater than this control indicated promoter activation and levels below this indicated promoter repression. The experiment was replicated.

Figure 32:
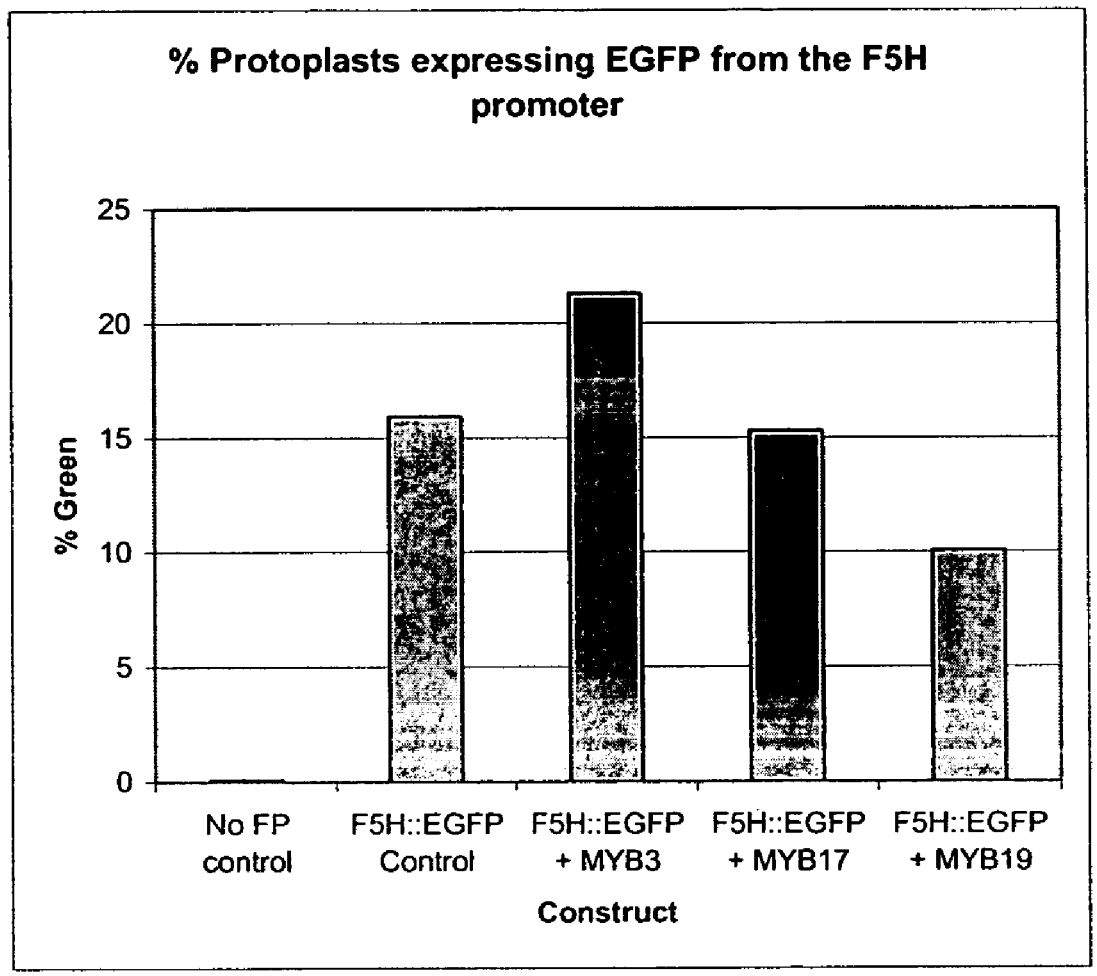
FIG. 32 shows expression of EGFP from Lolium multiflorum protoplasts transfected with the EGFP gene under the control of the grass F5H promoter (SEQ ID NO: 8). The promoter::reporter construct was co-transfected either with a grass MYB transcription factor (TF) or without (basal expression level).

FIG. 32 shows the level of EGFP being expressed in protoplasts transfected with the grass F5H promoter, with and without the MYB transcription factors. The level of EGFP increased when MYB3 was co-transfected into the protoplasts, indicating that MYB3 is a transcriptional activator of the F5H promoter. MYB17 had no effect upon transcription, and MYB19 repressed expression from the F5H promoter.

Figure 33:
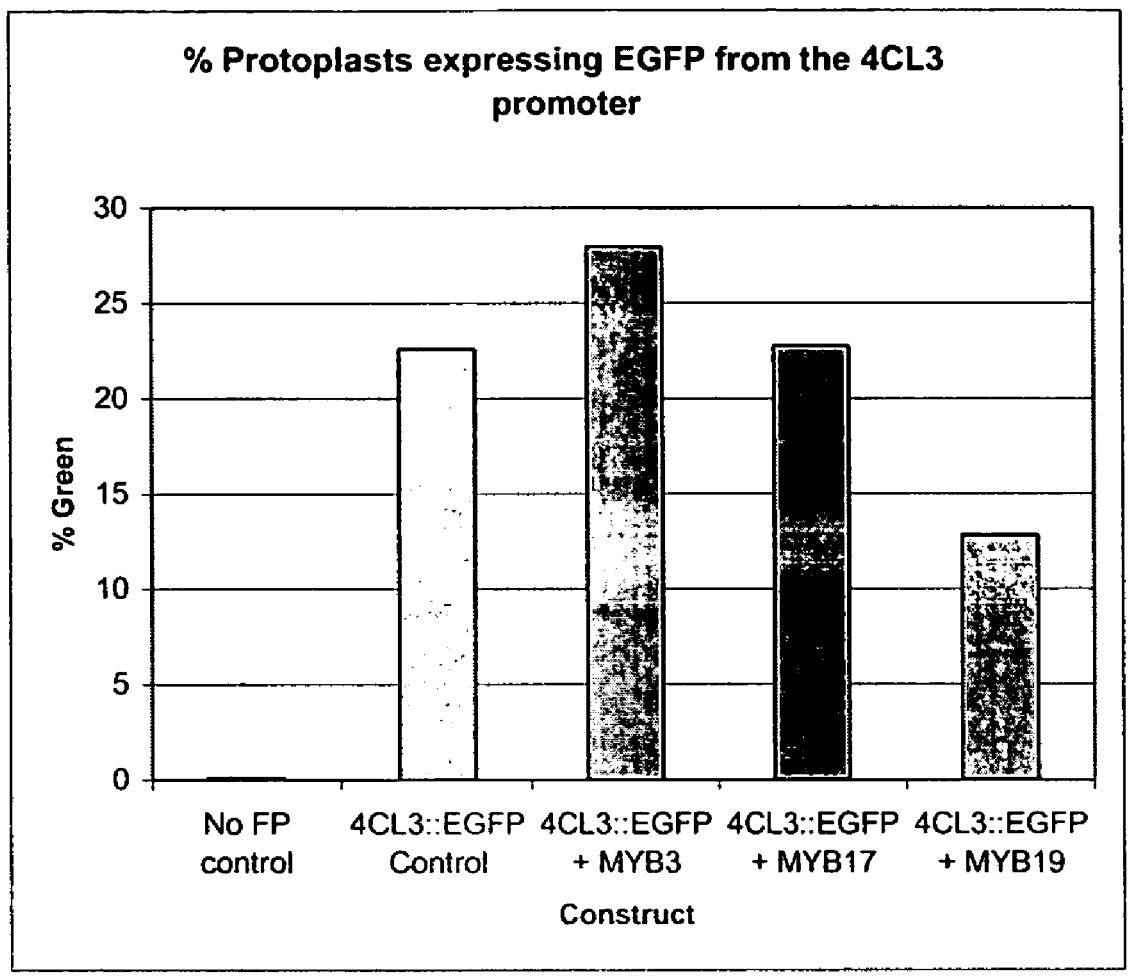
FIG. 33 shows expression of EGFP from Lolium multiflorum protoplasts transfected with the EGFP gene under the control of the grass 4CL3 promoter (SEQ ID NO: 5. The promoter::reporter construct was co-transfected either with a grass MYB TF, or without (basal expression level).

FIG. 33 shows the level of EGFP being expressed in protoplasts transfected with the grass 4CL3 promoter, with and without the MYB transcription factors. As with the F5H promoter, fluorescence increased when MYB3 was co-transfected into the protoplasts with 4CL3::EGFP, indicating that MYB3 is a transcriptional activator of the 4CL3 promoter. MYB17 had no effect upon transcription, and MYB19 repressed expression from the 4CL3 promoter.

The three grass MYB constructs were co-transfected into *Zinnia elegans* protoplasts with the individual lignin promoter::EGFP constructs, as described in Example 3. A vector containing Red Fluorescent protein (under the control of pine ubiquitin promoter) was used as a co-transfection marker to determine transfection efficiency. The transfections were analyzed similarly to the *Lolium multiflorum* protoplast transfections. The results from the *Zinnia* protoplasts mirror those seen in the *Lolium* protoplasts; MYB transcription factors are capable of activating or repressing the 4CL3 and F5H promoters.

EXAMPLE 8

Anthocyanin Gene and Tannin Gene Promoters from *Lolium perenne* and *Festuca arundinacea*

*L. perenne* Chalcone Synthase (CHS) and *F. arundinacea* Dihydroflavonal-4-reductase (DFR) cDNA sequences were identified using BLAST searches against homologous plant sequences. The most abundant chalcone synthase gene was identified by selecting the consensus sequence with the greatest number of EST members. Promoter polynucleotides were isolated using the GenomeWalker technique described above in Example 2, with gene specific primers designed to the 5' UTR of these cDNAs, (Table 5; SEQ ID NO: 28, 29, 49 and 50). Promoter fragments of three different lengths were isolated for the CHS promoter and one fragment was isolated for the DFR promoter. The determined sequences are given in SEQ ID NO: 9-11 and 38, respectively. These polynucleotides were analyzed for the presence of cis motifs using the PLACE database (see Table 2) and the motifs identified are shown in FIGS. 9-11 and 21, respectively.

Figure 20:
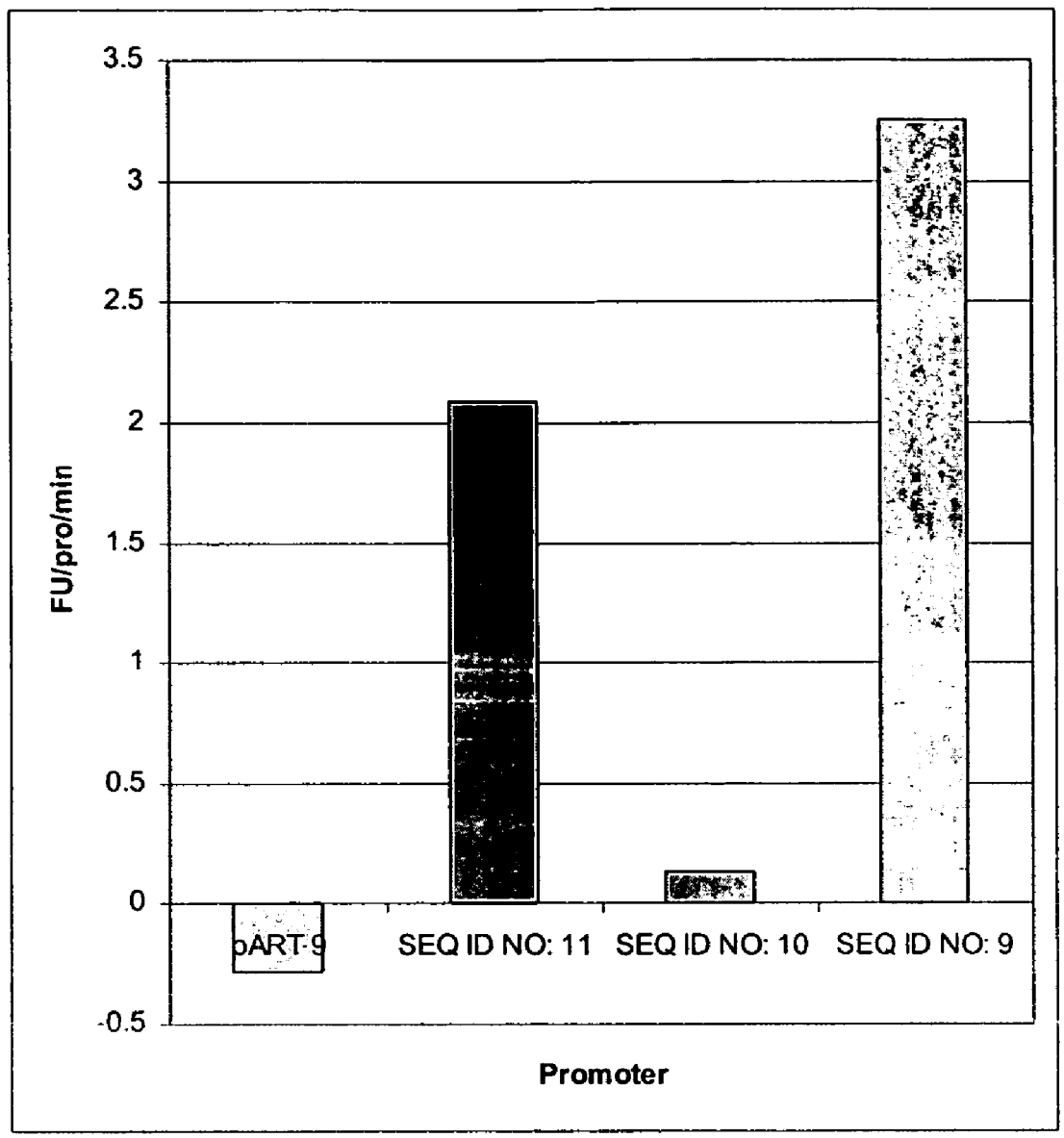
FIG. 20 shows expression levels of the CHS promoters given in SEQ ID NO: 9-11 in plant cells, as determined by the level of GUS expression. The longest promoter fragment (SEQ ID NO: 9) had the highest expression levels.

The promoter sequences were cloned with the GUS reporter gene as described in Example 3 and tested for activity in cell-based assays by transient transfection of FK cells. FIG. 20 shows the expression levels of the CHS promoters (SEQ ID NO: 9, 10 and 11). All three promoters had activity above the background control, with the longest promoter fragment (SEQ ID NO: 9) having the highest expression levels as measured by the level of GUS expression.

The CHS promoter of SEQ ID NO: 9, with GUS reporter, was then transformed into *Arabidopsis thaliana* to test for tissue-specific expression, as described in Example 5. Presence of the correct promoter in transgenic plants was tested using the primers described in Table 5.

TABLE 5

Tannin Promoters

| SEQ ID NO: | Promoter fragment | SEQ ID NO: Gene Specific Primer 1 | SEQ ID NO: Gene Specific Primer 2 |
|---|---|---|---|
| 9 | Chalcone Synthase | 28 | 29 |
| 10 | Chalcone Synthase | 28 | 29 |
| 11 | Chalcone Synthase | 28 | 29 |
| 38 | Dihydroflavonal-4-reductase (DFR) | 49 | 50 |

EXAMPLE 9

Floral Specific and Flowering Time Gene Promoters from *Lolium perenne* and *Festuca arundinacea*

*L. perenne* FT (Flowering Locus T) cDNA sequences were identified using BLAST searches against homologous plant sequences. Promoter polynucleotides were isolated using the GenomeWalker technique described in Example 2, with gene specific primers designed to the 5' UTR of this cDNA (Table 6; SEQ ID NO: 30 and 31). A 443 bp promoter fragment was isolated. The determined sequence is given in SEQ ID NO: 12. This polynucleotide was analyzed for cis motifs using the PLACE database (see Table 2) and the motifs identified are shown in FIG. 12.

TABLE 6

Floral-specific and Flowering Time Promoters

| SEQ ID NO: | Promoter fragment | SEQ ID NO: Gene Specific Primer 1 | SEQ ID NO: Gene Specific Primer 2 |
|---|---|---|---|
| 12 | Flowering Locus T (FT) | 30 | 31 |

EXAMPLE 10

Antifreeze Protein Gene Promoters from *Lolium perenne* and *Festuca arundinacea*

*Lolium perenne* antifreeze protein cDNA sequences were identified and promoter polynucleotides were isolated using the GenomeWalker technique described in Example 2, with gene specific primers designed to the 5' UTR of this cDNA (Table 7; SEQ ID NO: 32 and 33). Three promoter fragments from the AFP1 gene were isolated. The determined sequences are given in SEQ ID NO: 13-15. These polynucleotides were analyzed for cis motifs using the PLACE database (see Table 2) and the motifs identified are shown in FIGS. 13-15, respectively.

TABLE 7

Antifreeze Protein Promoters

| SEQ ID NO: | Promoter fragment | SEQ ID NO: Gene Specific Primer 1 | SEQ ID NO: Gene Specific Primer 2 |
|---|---|---|---|
| 13 | Antifreeze protein | 32 | 33 |
| 14 | Antifreeze protein | 32 | 33 |
| 15 | Antifreeze protein | 32 | 33 |

EXAMPLE 11

Anthocyanin Gene and Tannin Gene Promoters from *Arabidopsis thaliana*

A number of dihydroflavonol-4-reductase-like (DFR) genes were identified from *Arabidopsis thaliana*; the protein homology is given in Table 1. Using the publicly available *Arabidopsis thaliana* genome sequence, primers were designed to amplify 1,500 nucleotides upstream of the coding region. Promoter fragments were amplified from *Arabidopsis thaliana* ecotype Columbia total genomic DNA using standard PCR protocols and the specific primers described in Table 8 and given in SEQ ID NO: 34-37. The promoter fragments were cloned and sequenced to verify that the correct sequence fragment was isolated using the primers given in Table 8. The AtDFR1 (SEQ ID NO: 16) and AtDFR2 (SEQ ID NO: 17) promoters were analyzed for cis motifs using the PLACE database (see Table 2) and the motifs are shown in FIGS. 16 and 17, respectively.

The promoter fragments of SEQ ID NO: 16 and 17 were cloned into the binary plasmid pART27 containing the GUS reporter gene and transformed into *Arabidopsis thaliana* to test for tissue-specific expression, as described in Example 5. The expression profile in *Arabidopsis* of the AtDFR2 promoter (SEQ ID NO: 17) is given in Table 8.

TABLE 8

A. thaliana Anthocyanin and Tannin Promoters

| SEQ ID NO: Promoter fragment | SEQ ID NO: Forward Primer | SEQ ID NO: Reverse Primer | Expression Profile in Arabidopsis thaliana |
|---|---|---|---|
| 16 Dihydroflavonol-4-reductase-like (DFR) | 34 | 35 | |
| 17 Dihydroflavonol-4-reductase-like (DFR) | 36 | 37 | GUS expression in anthers in Arabidopsis thaliana. Wound induced expression in leaves. |

EXAMPLE 12

Transcription Factor Gene Promoters from *Lolium perenne* and *Festuca arundinacea*

One MYB transcription factor gene (MYB21) cDNA sequence from *L. perenne*, two MADs BOX (MADs6 and MADs29) cDNAs from *L. perenne* and one *F. arundinacea* (MADs9) cDNA sequence were identified using BLAST searches against homologous plant sequences. Promoter polynucleotides were isolated using the GenomeWalker technique described in Example 2, with gene specific primers designed to the 5' UTR of these cDNAs. The gene specific primer sequences are given in SEQ ID NO: 51 and 52 (MYB21), SEQ ID NO: 63 and 64 (MADs6), SEQ ID NO: 65 and 66 (MADs9) and SEQ ID NO: 61 and 62 (MADs29). One promoter fragment was isolated from each sequence, cloned and sequenced. The determined promoter sequences are given in SEQ ID NOS: 39, 47, 48 and 46, respectively. These polynucleotides were analyzed for cis motifs using the PLACE database (see Table 2) and the identified motifs are shown in FIGS. 22, 30, 31 and 29, respectively.

TABLE 9

Transcription Factor Gene Promoters

| SEQ ID NO: | Promoter fragment | SEQ ID NO: Gene Specific Primer 1 | SEQ ID NO: Gene Specific Primer 2 |
|---|---|---|---|
| 39 | MYB21 | 51 | 52 |
| 47 | MADs6 | 63 | 64 |
| 48 | MADs9 | 65 | 66 |
| 46 | MADs29 | 61 | 62 |

EXAMPLE 13

Peroxidase Gene Promoters from *Lolium Perenne*

Two *Lolium perenne* peroxidase cDNA sequences were identified (PER1 and PER3) and promoter polynucleotides were isolated using the GenomeWalker technique described in Example 2, with gene specific primers designed to the 5' UTR of these cDNAs (See Table 10; SEQ ID NO: 53 and 54 for PER1, SEQ ID NO: 55 and 56 for PER3). One promoter fragment for each peroxidase gene was isolated. The determined sequences are given in SEQ ID NO: 40 and 42. The length of the promoter sequence of PER1 was 468 bp. Primers were designed using this sequence to obtain promoter sequence further upstream (See Table 10; SEQ ID NO: 53 and 54). This new, extended fragment, termed PER1b is given in SEQ ID NO: 41. All of these polynucleotides were analyzed for cis motifs using the PLACE database (see Table 2) and the motifs identified are shown in FIGS. 23-25.

TABLE 10

Peroxidase Gene Promoters

| SEQ ID NO: | Promoter fragment | SEQ ID NO: Gene Specific Primer 1 | SEQ ID NO: Gene Specific Primer 2 |
|---|---|---|---|
| 40 | PER1 | 53 | 54 |
| 41 | PER1b | 53 | 54 |
| 42 | PER3 | 55 | 56 |

EXAMPLE 14

Fructosyltransferase Gene Promoters from *Lolium perenne*

A sucrose-fructan 6-fructosyltransferase (6-SFT) cDNA from *L. perenne* sequence was identified using BLAST searches against homologous plant sequences. Promoter polynucleotides were isolated using the GenomeWalker technique described in Example 2, with gene specific primers designed to the 5' UTR of this cDNA. The gene specific primer sequences are given in SEQ ID NO: 57 and 58. One promoter fragment of 629 bp was isolated, cloned and sequenced. The determined sequence is given in SEQ ID NO: 43. This polynucleotide was analyzed for cis motifs using the PLACE database (see Table 2) and the identified motifs are shown in FIG. 26.

TABLE 11

Sucrose-fructan 6 fructosyltransferase (SFT) Gene Promoters

| SEQ ID NO: | Promoter fragment | SEQ ID NO: Gene Specific Primer 1 | SEQ ID NO: Gene Specific Primer 2 |
|---|---|---|---|
| 43 | 6-SFT | 57 | 58 |

SEQ ID NO: 1-73 are set out in the attached Sequence Listing. The codes for nucleotide sequences used in the attached Sequence Listing, including the symbol "n," conform to WIPO Standard ST.25 (1998), Appendix 2, Table 1.

All references cited herein, including patent references and non-patent publications, are hereby incorporated by reference in their entireties.

While in the foregoing specification this invention has been described in relation to certain preferred embodiments, and many details have been set forth for purposes of illustration, it will be apparent to those skilled in the art that the invention is susceptible to additional embodiments and that certain of the details described herein may be varied.

We claim:

1. An isolated polnucleotide comprising SEQ ID NO: 5 or 6.

2. An isolated polynucleotide comprising a sequence having at least 95% identity to the whole length of SEQ ID NO:5 or 6, wherein the polynucleotide is capable of driving expression of an operably linked polynucleotide in a plant cell.

3. A genetic construct comprising a polynucleotide according to claim 1.

4. A genetic construct comprising, in the 5'-3' direction:
   (a) a promoter sequence,
   (b) a DNA sequence of interest; and
   (c) a gene termination sequence,
   wherein the promoter sequence comprises an isolated polynucleotide according to claim 1.

5. The genetic construct of claim 4, wherein the DNA sequence of interest comprises an open reading frame encoding a polypeptide of interest.

6. The genetic construct of claim 4, wherein the DNA sequence of interest comprises a non-coding region of a gene encoding a polypeptide of interest.

7. A transgenic cell comprising a genetic construct of claim 4, wherein the cell is a bacterial or plant cell.

8. An organism comprising a transgenic cell according to claim 7, wherein the organism is a bacteria or a plant.

9. A transgenic plant comprising a transgenic cell according to claim 7, or a part or propagule or progeny thereof, wherein the part, propagule or progeny thereof comprises a genetic construct of claim 4.

10. A method for modifying a phenotype of a target plant, comprising stably incorporating into the genome of the target plant a genetic construct comprising:
    (a) a promoter sequence comprising a polynucleotide of any one of claim 1 or claim 3;
    (b) a DNA sequence of interest; and
    (c) a gene termination sequence.

11. An isolated polynucleotide comprising SEQ ID NO: 5 or 6 operably linked to a heterologous polynucleotide.

12. The polynucleotide of claim 11, wherein the heterologous polynucleotide comprises an open reading frame.

13. A genetic construct comprising a polynucleotide according to claim 2.

14. A genetic construct comprising, in the 5'-3' direction:
(a) a promoter sequence,
(b) a DNA sequence of interest; and
(d) a gene termination sequence,
wherein the promoter sequence comprises an isolated polynucleotide according to claim 2.

15. The genetic construct of claim 14, wherein the DNA sequence of interest comprises an open reading frame encoding a polypeptide of interest.

16. The genetic construct of claim 14, wherein the DNA sequence of interest comprises a non-coding region of a gene encoding a polypeptide of interest.

17. A transgenic cell comprising a genetic construct of claim 14, wherein the cell is a bacterial or plant cell.

18. An organism comprising a transgenic cell according to claim 17, wherein the organism is a bacteria or a plant.

19. A transgenic plant comprising a transgenic cell according to claim 17, or a part or propagule or progeny thereon wherein the part, propagule or progeny thereof comprises a genetic construct of claim 14.

* * * * *

UNITED STATES PATENT AND TRADEMARK OFFICE
CERTIFICATE OF CORRECTION

PATENT NO.         : 7,718,789 B2
APPLICATION NO.    : 11/138987
DATED              : May 18, 2010
INVENTOR(S)        : Clare K. Elton, Claire Hall and Jeroen Demmer It is certified that error appears in the above-identified patent and that said Letters Patent is hereby corrected as shown below:

| Col. No. | Line(s) | Edits |
|---|---|---|
| 83 | 46 | Replace "An isolated polnucleotide" with --An isolated polynucleotide-- |

Signed and Sealed this

Third Day of August, 2010

David J. Kappos
*Director of the United States Patent and Trademark Office*

SEQUENCE LISTING

<160> NUMBER OF SEQ ID NOS: 73

<210> SEQ ID NO 1
<211> LENGTH: 861
<212> TYPE: DNA
<213> ORGANISM: Festuca arundinacea

<400> SEQUENCE: 1

```
aaagtgtcca tctactaaaa cagttgtgga ggacatatca aataatttat tcccgtgagt    60
tgtacatatc agtaaacatg aaattaagga cttgttaagg tgggattaaa ctagcagttt   120
taatattcat tattcaaata taggcgttcc acactgttgt taggtccaaa gaaataactt   180
cgaaaggata tcttcgatgc cctttttgtgt ctagaatcct tgcatttttcc tttcacgcgt   240
gtgttggatc aacatttcat gagtttattt agcgtaattt ttggttcttc taaacatacc   300
cggtacacat aaacataacg ttcacgtgtt attttgtact cgcttcgatc cataataagt   360
atcggaaact tagtacaaaa gttgtactta ctagtacaaa attctcaaca ttttttatag   420
atcggaggga gggagtagta gttttcaaac aacatgattc caactctcaa aacatggctt   480
ttttgtgagg tacacaattt tacaaactct aattcaaatc tttgctagag aatacctgtc   540
gaaaagtag aaggtcttaa ttgtttgtta ttccatgcca accatttttct ctctttccat   600
ttcccaccaa aactgacaga aaaatacttt attttttccca agaaaatca cgagagggct   660
gagtaaaaaa aagatgtcca tataaaacag ggcacaaggc caaggctagc gcttggttct   720
cctgcctctt gccttagttc gccaccaccg ccgccaccta ccccctcatc ctttctcctc   780
ccccgctctc gcagcgtccg ctcatctcgg tgagaggtct tcaggcgagc aggttccct   840
acatcccccg agtcacttaa t                                             861
```

<210> SEQ ID NO 2
<211> LENGTH: 672
<212> TYPE: DNA
<213> ORGANISM: Festuca arundinacea

<400> SEQUENCE: 2

```
atcttcgatg cccttttgtg tctagaatcc ttgcattttc ctttcacgcg tgtgttggat    60
caacatttca tgagtttatt tagcgtaatt tttggttctt ctaaacatac ccggtacaca   120
taaacataac gttcacgtgt tattttgtac tcgcttcgat ccataataag tatcggaaac   180
ttagtacaaa agttgtactt actagtacaa aattctcaac attttttata gatcggaggg   240
agggagtagt agttttcaaa caacatgatt ccaactctca aaacatggct ttttgtgag   300
gtacacaatt ttacaaactc taattcaaat ctttgctaga gaatacctgt cgaaaagta   360
gaaggtctta attgtttgtt attccatgcc aaccattttc tctctttcca tttcccacca   420
aaactgacag aaaaatactt tattttttccc aagaaaatc acgagagggc tgagtaaaaa   480
aaagatgtcc atataaaaca gggcacaagg ccaaggctag cgcttggttc tcctgcctct   540
tgccttagtt cgccaccacc gccgccacct accccctcat cctttctcct ccccgctct   600
cgcagcgtcc gctcatctcg gtgagaggtc ttcaggcgag caggttcccc tacatccccc   660
gagtcactta at                                                       672
```

<210> SEQ ID NO 3
<211> LENGTH: 594
<212> TYPE: DNA
<213> ORGANISM: Festuca arundinacea

<400> SEQUENCE: 3

```
agtttatttta gcgtaattttt tggttcttct aaacataccc ggtacacata aacataacgt    60
tcacgtgtta ttttgtactc gcttcgatcc ataataagta tcggaaactt agtaaaagtt   120
gtacttacta gtacaaaatc ctcaacattt tttatagatc ggagggaggg agtagtagtt   180
ttcaaacaac atgattccaa ctctcaaaac atggctttt tgtgaggtac acaattttac    240
aaactctaat tcaaatcttt gctagagaat acctgtcgaa aaatagaag gtcttaattg     300
tttgttattc catgccaacc attttctctc tttccatttc ccaccaaaac tgacagaaaa   360
atactttatt tttcccaaag aaaatcacga gagggctgag taaaagatgt ccatataaaa   420
cagggcacaa ggccaaggct agcgcttggt tctcctgcct cttgccttag ttcgccacca   480
ccgccgccac ccaccccctc atcctttctc ctcccccgct ctcgcagcgt ccgctcatct   540
cggtgagagg tcttcaggcg agcaggttcc cctacatccc ccgagtcact taat          594
```

<210> SEQ ID NO 4
<211> LENGTH: 801
<212> TYPE: DNA
<213> ORGANISM: Festuca arundinacea

<400> SEQUENCE: 4

```
aaaaatgtca aaaattctg aaacaaaatt tctggtgtac atcatgatat tctatgttcg     60
tacacaaatt tcgtgggaaa caacattttt atgtggcatg tacaaaaaag acaaaaaaat   120
atcatgtacg tagtcgtgtt ggagcataaa aaattgtctt ttttacacgg gacacaaaaa   180
aaatattatt tttcccgaaa acttgtgcac gaacatagaa tgtctagatg tacatgtgca   240
attttatttc aaatttttt gatattttga atatgttttt tcacacactg ggttcatatg    300
cacccatgag ccgaaataaa tatcctgttt gttttaagtc aaactactct aggtttcatc   360
aggtttataa aaaaaacatc accaacttag tttcattaga ttcatcataa cattatatta   420
acataatttc ttataaactc gatcgaactt agaaaaaata tgttaatata tatagaaaac   480
ctcaattatt ttggaaccgt ttcccttcgt gacttttgtt ttcgattttt tttcttgaa    540
acgtgactgc cataggtaac tgaccggaac ggcgggaagc attggccggc tcacgtgaat   600
cgtgtccacg gagcattggc ccacgtaaaa gcaaccgctc ctcaccgccg cacccagaaa   660
ctaccccga tctctcatcc ccttctcccc cctctctcct ccgccctgcc cccttttatc     720
tcccgatctc acacgttttg ggaagagaga gaaagagagc ggtttcgaga gggccattct   780
tcgtacccaa ggagagatcc a                                              801
```

<210> SEQ ID NO 5
<211> LENGTH: 1077
<212> TYPE: DNA
<213> ORGANISM: Festuca arundinacea

<400> SEQUENCE: 5

```
ctgaaagcga agtaattgtg aagagaggga gtacaaacta gtaatacgca taccaactta    60
gctcatacaa aaaggttgtt gttggccagg agaaactatg gaagtttgtt cctttttaaaa  120
aggcactttt ttacgtgtac acatttgagt ttcgttcgtc gaagaccaag taaaaatggg   180
cgaacagaaa cggcgacttt gagagttgag acatggttgt caaatggaac gatcaccgta   240
gaccacaaaa tcaacaaatt tgaaccccaa aatacgagga agtctagcat gaaagttgta   300
ccaaccgctg ctatttccgt ctccttcacc agatatggaa tacagccctg ccgctggtga   360
```

```
cacatgtatc tgagcaggtt ttgggcatga cctgggacat ggatgtcaaa tggaacaatc    420
accgtagacc actaaatatc aacaaacttg accccaaaa taccaggaag cctaatatat    480
aacatgaaag ttgtaccaac ctctgctatt tctgtctcct tcacctgaga tggtgtaatg    540
caaaatacag ccttgaatgt ggtgacacat gttttatttt cgaaaaaaga aaggtgaca     600 gatgtatctg aagcaggttt gggcatgact ttttgcagcc tgagaagcaa ccatcgtcac    660
caaccccggc gcacgaatga ccgaccaatg cggggaggat tctgtcgaac ggctggccaa    720
gccaagctgc cgcttttttt tttttttttt gcgaaggaag ccaagctgcc gctgatcatg    780
gagtaggtaa acgaggtcga cgtggcaccc cctgccccag tcaacgaacc ccagccattc    840
tctccctgtc tcgccaaccc tcccactctg actgccatgt tggtcccaca cgtcatcctc    900
tcaggcccca ctcaccaact ccccgactcc ttccccgta tattacaccc gccatcttcc    960
gttcctccct tcttcttcag gagatcaagt aagcacgcgc acgcagtcgc acaagccatc   1020
tccgacgact aatttaacca ccttagaaga tttagtctcc gtttctctct cgatcgc      1077

<210> SEQ ID NO 6
<211> LENGTH: 961
<212> TYPE: DNA
<213> ORGANISM: Festuca arundinacea

<400> SEQUENCE: 6
aaaaaggcac ttttttacgt gtacacattt gagtttcgtt cgtcgaagac caagtaaaaa     60
tgggcgaaca gaaacggcga ctttgagagt tgagacatgg ttgtcaaatg gaacgatcac    120
cgtagaccac aaaatcaaca aatttgaacc ccaaaatacg aggaagtcta gcatgaaagt    180
tgtaccaacc gctgctattt ccgtctcctt caccagatat ggaatacagc cctgccgctg    240
gtgacacatg tatctgagca ggttttgggc atgacctggg acatggatgt caaatggaac    300
aatcaccgta gaccactaaa tatcaacaaa cttgaccccc aaaataccag gaagcctaat    360
atataacatg aaagttgtac caacctctgc tatttctgtc tccttcacct gagatggtgt    420
aatgcaaaat acagccttga atgtggtgac acatgtttta ttttcgaaaa agaaaaggt    480 gacagatgta tctgaagcag gtttgggcat gacttttgc agcctgagaa gcaaccatcg    540
tcaccaaccc cggcgcacga atgaccgacc aatgcgggga ggattctgtc gaacggctgg    600
ccaagccaag ctgccgcttt tttttttttt ttttgcgaag gaagccaagc tgccgctgat    660
catggagtag gtaaacgagg tcgacgtggc accccctgcc ccagtcaacg aaccccagcc    720
attctctccc tgtctcgcca accctcccac tctgactgcc atgttggtcc cacacgtcat    780
cctctcaggc cccactcacc aactccccga ctccttcccc cgtatattac acccgccatc    840
ttccgttcct cccttcttct tcaggagatc aagtaagcac gcgcacgcag tcgcacaagc    900
catctccgac gactaattta accaccttag aagatttagt ctccgtttct ctctcgatcg    960
c                                                                    961

<210> SEQ ID NO 7
<211> LENGTH: 740
<212> TYPE: DNA
<213> ORGANISM: Lolium perenne

<400> SEQUENCE: 7
cctggagtga atccaggaag tgttagtgcc attagttagt ggagtagtgg gtcagagagt     60
ggcgtgagtt gcgtggcaga gaagtgccta aacttgtata tatattctgc attgagttaa    120
tgagaagata gcccgtgacg gctgaagaga aaagatgtag cctctctcgt acaccatgga    180
```

```
tagaattcct cttggcaaag ccatggttat ttctccatgg tgtgtgcgcg tgtgtcttct    240
ttcttgagtt ttcctgatct ttctcaccat gtgtgtgttc ttgtgaggtg agagagacaa    300
gagagattgt gagagatcag aggtagaaga agaagatggg gcttcgagat gcagccccca    360 acacccccgcc ctcgaagaag gaacccttga gagtgctcgc cgcctgccac ctcgcgatcg   420
ctctgatgac catcgcgggc tggcctctct ccgcaataca ggtaaaatta tttcattcag    480
aaaataattg taccattaac cgaaattttt gtgccataac cggctgtagc tatagtcggc    540
cgatccccgg agttcgccag acaaaaaagg agtaggtagt gtgtgtggta ggtgaaggga    600
gaaagcccca tatatatagc cccttctcac cctccctcca atgtacacct gatcgctcgg    660
gtctctcgct catactacca aaaacaccca gcagcacacc agcgtctctc ggcccaggag    720
aagcagacac aggcagagat                                                740

<210> SEQ ID NO 8
<211> LENGTH: 460
<212> TYPE: DNA
<213> ORGANISM: Festuca arundinacea

<400> SEQUENCE: 8
aaatgagatc tagtttgatc atgaattaaa agtggtctga aaatagactt aaattctgtt     60
aaacttctaa tatatatggt aaatgcacgg cgttcatacc atattaatac tttcataatt    120
tgttttttca tctgatactt agtttagaag caaatttatt cgaatcctct tctttcacca    180
gttcttccca gtccccacta ccaatcttag aagtatcttt gcatcttaat cctctccttt    240
ctgatgcccc ggaaacaaat taaaatggaa atatatatgc ggcgctgcac gccatcaccg    300
tacgtgtctc aacctaatct agaaaatctc ccatcctcct cacgacctca cctacccctc    360
caactatata taccagcca ccctccacct ttgtcctcag ctctactcca agagcatcaa     420
tctaaaaccc acgcgatcga acacccctag aaaaaaaaac                          460

<210> SEQ ID NO 9
<211> LENGTH: 911
<212> TYPE: DNA
<213> ORGANISM: Lolium perenne

<400> SEQUENCE: 9
cctcttctcc actagtgaat gggtgggtcc cttttctact agtgtgacgc acctggcgca     60
ggatcgagaa ggatccgagg aggatagcgg gcttcctcgg caacaggaac ttccctttgg    120
accatccacc gccgcctcgt catcgaaatg cgtcgccccg ctgggagata ccctaaatct    180
agatgctaca tgcccatac cccacgttac ttagtgcacc agcgaacaag gacagaacaa     240
ccggtctttc tgtattcatc aacccatacg gacaaaatca gacaccacag ccgcgttgga    300
gtttccctta cgtcacacac acacaccagg gacgtgagtt ctgtggtttg ttatcggtag    360
ctgtaatcca gttccctctc tgaatcaata catatcggag tagcacacat tttttgttg     420 aaatatatta gtgctgggct acgtgctacg atcgatcgat atagctgggt agacttctcg    480
aaggttatac tcgggcagca gaaatcacac atgcatgccg tgcgtgtagc attgatgtat    540
ctagactgcg tgactggttg ttcctaaaga tccaagagga tccataaggt cgacataggg    600
cgggagcgca tccaagcagc tgggcaggcc caaggccaag cgagccaact aactcccatt    660
cggccggatt ggttggtaga cgtgtcgcac gcgccaccca tccctccct ccgcaggcgt    720 ggccttccat cctcccgtcc aactgaccta accctcaccc ccgcggccgg ctctccttca   780
```

| | |
|---|---|
| accacccttc ccgcctatat atctcgtccg cgcacacatg gcaccacacc acagcagtac | 840 |
| tacaacaagg agcaactgtc actcattcat ctgtcgtctc ctgcttccct caagcttaga | 900 |
| tcgattgcag c | 911 |

<210> SEQ ID NO 10
<211> LENGTH: 826
<212> TYPE: DNA
<213> ORGANISM: Lolium perenne

<400> SEQUENCE: 10

| | |
|---|---|
| agcgggcttc ctcggcaaca ggaacttccc tttggaccat ccaccgccgc ctcgtcatcg | 60 |
| aaatgcgtcg ccccgctggg agatacccta aatctagatg ttacatgccc cataccccac | 120 |
| gttacttagt gcaccagcga acaaggacag aacaaccggt ctttctgtat tcatcaaccc | 180 |
| atacggacaa aatcagacac cacagccgcg ttggagtttc ccttacgtca cacacacaca | 240 |
| ccagggacgt gagttctgtg gtttgttatc ggtagctgta atccagttcc ctctctgaat | 300 |
| caatacatat cggagtagca cacattttt tgttgaaata tattagtgct gggctacgtg | 360 |
| ctacgatcga tcgatatagc tgggtagact tctcgaaggt tatactcggg cagcagaaat | 420 |
| cacacatgca tgccgtgcgt gtagcattga tgtatctaga ctgcgtgact ggttgttcct | 480 |
| aaagatccaa gaggatccat aaggtcgaca tagggcggga gcgcatccaa gcagctgggc | 540 |
| aggcccaagg ccaagcgagc caactaactc ccattcggcc ggattggttg gtagacgtgt | 600 |
| cgcacgcgcc acccatcccc tccctccgca ggcgtggcct tccatcctcc cgtccaactg | 660 |
| acctaacccc tcaccccgcg gccggctctc cttcaaccac ccttcccgcc tatatatctc | 720 |
| gtccgcgcac acatggcacc acaccacagc agtactacaa caaggagcaa ctgtcactca | 780 |
| ttcatctgtc gtctcctgct ccctcaagc ttagatcgat tgcagc | 826 |

<210> SEQ ID NO 11
<211> LENGTH: 742
<212> TYPE: DNA
<213> ORGANISM: Lolium perenne

<400> SEQUENCE: 11

| | |
|---|---|
| accctaaatc tagatgttac atgccccata ccccacgtta cttagtgcac cagcgaacaa | 60 |
| ggacagaaca accggtcttt ctgtattcat caacccatac ggacaaaatc agacaccaca | 120 |
| gccgcgttgg agtttccctt acgtcacaca cacacaccag gacgtgagt tctgtggttt | 180 |
| gttatcggta gctgtaatcc agttccctct ctgaatcaat acatatcgga gtagcacaca | 240 |
| ttttttgtt gaaatatatt agtgctgggc tacgtgctac gatcgatcga tatagctggg | 300 |
| tagacttctc gaaggttata ctcgggcagc agaaatcaca catgcatgcc gtgcgtgtag | 360 |
| cattgatgta tctagactgc gtgactggtt gttcctaaag atccaagagg atccataagg | 420 |
| tcgacatagg gcgggagcgc atccaagcag ctgggcaggc ccaaggccaa gcgagccaac | 480 |
| taactcccat tcggccggat tggttggtag acgtgtcgca cgcgccaccc atccctccc | 540 |
| tccgcaggcg tggccttcca tcctcccgtc caactgacct aaccctcac ccgcggccg | 600 |
| gctctccttc aaccaccctt cccgcctata tatctcgtcc gcgcacacat ggcaccacac | 660 |
| cacagcagta ctacaacaag gagcaactgt cactcattca tctgtcgtct cctgcttccc | 720 |
| tcaagcttag atcgattgca gc | 742 |

<210> SEQ ID NO 12
<211> LENGTH: 443

<212> TYPE: DNA
<213> ORGANISM: Lolium perenne

<400> SEQUENCE: 12

| | | | | | |
|---|---|---|---|---|---:|
| aaattatgta | aatagcggta | ttttttttgc | ggtattattg | acataccatt | cgagaaaaaa | 60 |
| aaacttgacc | cagattacat | acaaaagagg | gacccaattc | attattctcc | tgtgtaggcg | 120 |
| aagcagtttc | cctgccacta | agacaacgtg | tttgtgtact | ctacaaagca | atttagcttg | 180 |
| acggaaaacg | tacctagaaa | aacatcgagg | tgatcaagac | tgttgcatat | tcgctctcgg | 240 |
| cctctcctgc | gccgcccgta | caagtgcact | agcatttgcc | cctttcctag | acgagctagc | 300 |
| aaacaggaat | aggccatttg | acccacccac | tcccccttc | ccaaacacgt | ctcttctctt | 360 |
| ctctcttcgt | catcaccacc | agcacgcgcg | cgcgcgcgag | tagtagtagt | agccctccag | 420 |
| agagtccacc | agacagagag | taa | | | | 443 |

<210> SEQ ID NO 13
<211> LENGTH: 1496
<212> TYPE: DNA
<213> ORGANISM: Lolium perenne

<400> SEQUENCE: 13

| | | | | | |
|---|---|---|---|---|---:|
| ccttgatgga | ggatgcttgg | ctcttggatg | tttctggaga | gttgtccatt | gatgggtgga | 60 |
| tgcaatgcac | cctactttgg | gaagagttgg | ggagagtgcc | tcgtgatgaa | ataggccgg | 120 |
| atcaaatcac | ttggaaagga | tcggcgtcta | ggcggtactc | caccagggag | acttacaaca | 180 |
| tgctttgcat | ggggaggatt | acttggagta | tggccaagcc | aatttgaaga | tccttttgcac | 240 |
| ctctcaagtg | caaaatcttc | agatggttgg | cgataaagcg | ccggctatag | acttcggata | 300 |
| ggagggctag | gcatggccta | caggcctgac | ccatgtgcca | catgccttca | ggaggaggat | 360 |
| aatgttgatc | atattctggc | acagtgccca | tacaccaaga | tggtctggtt | cggctgtctg | 420 |
| agaagaatgg | gatcgcagct | acaggagccg | caggagaaca | caaatttgga | gagatggtgg | 480 |
| atggaagcga | ggaaaaggct | gcgtagggag | gacaagagag | gcttcgacac | attcgttttg | 540 |
| ttgatcgcct | ggacgctttg | gaagcaaagg | aacgcccggg | tgtttgggaa | cttggataga | 600 |
| caactctcca | cggcgcagat | cattgataca | gtcctcgagg | agtttagcct | ttggtgggct | 660 |
| gcgaggggag | gagagcggcg | agtgatgctg | cgagagtagg | cgtgagtcct | gggtgtgtgc | 720 |
| gtgggttggc | caagggcaga | tgttcgcatc | cccctctggt | ttcttgtaat | tgttgttgct | 780 |
| cccttctata | aagattcggc | acgcttttcg | cgtgcccgcg | aaaagaata | tcaataggt | 840 |
| ccctactatt | aacagatttc | tcccagattt | tagattagta | tatttgaaat | tactttaaaa | 900 |
| cagtatgaac | tttcaaaaaa | taatcaatac | aaaaatgttt | cacaatttct | gtagattact | 960 |
| gcactacaac | cggttataga | ataccccggc | tatatatata | tatatctatt | tataagtact | 1020 |
| agcaagagca | aattaaagtc | tgactttgat | gacaattcgc | acgccgcatt | attggactgg | 1080 |
| tcacggggaa | atgacaacgc | agccaagagc | caagcgtgtc | ggttacacag | ctcgccgtcg | 1140 |
| tctctctagg | atagattcat | cgtccgtgtg | accgtgtctg | cataataaaa | tctcccaaag | 1200 |
| gatatttttgt | gtcctcatac | tgcaatgtgg | cctctcttat | ctaattacct | atccagctca | 1260 |
| cctccgaccc | tatatggact | agaattggtc | catgccagcc | acggatttca | gtcgacgcac | 1320 |
| aacaacaaaa | acgaaggttg | aattgggagg | cagttgtggg | ccacaaacta | gctagtactg | 1380 |
| agccccttgc | aacctcgcat | gcttacaaac | acacagagga | cactataaga | tgggatgcac | 1440 |
| atgcaccacc | cagacaacaa | cacttgcgag | tcacttgcat | tgcaggaaag | gtttct | 1496 |

<210> SEQ ID NO 14
<211> LENGTH: 1421
<212> TYPE: DNA
<213> ORGANISM: Lolium perenne

<400> SEQUENCE: 14

| | | | | | |
|---|---|---|---|---|---|
| atcatttta | acaaattcca | aacagtgcga | atagaattct | attgggatac | tatcagttcc | 60 |
| aggagatttt | ttctccgttg | caaataaggc | aaatttcacc | tcatattcag | aaaaaggttt | 120 |
| tatcatatca | ctattatctt | cctcattaag | cttttcatta | ggactccata | agttttggtc | 180 |
| aatacggaaa | aaattgccat | gggcaggacc | aaaaagatct | tataatact | tcagtagcat | 240 |
| gattgaccga | gttgtatgcc | ccttccacaa | tgataccatt | attatccaag | gagagtcctc | 300 |
| ccattagcaa | ttatatgaaa | gtaagcagta | ttttgatcct | cttctaacaa | ccatttccat | 360 |
| gggccttttg | atggcaataa | ctttcctcct | cctcataaag | tttaaacaat | tcttcctgca | 420 |
| tcttaactct | gtaagacatt | tcatctgtag | ttaacttccc | attctcctct | ggaaattcca | 480 |
| gcaccaaaag | ctccttcttg | agctctaact | tcctctttt | attactacca | agtaccaaa | 540 |
| agtatttgca | ccccaacctt | taccatactt | attaatcctc | actatcttga | tattaagaat | 600 |
| gtcaatacta | ttaacaggtt | tctcctagat | tttagattag | tatatttgag | attactttaa | 660 |
| aactgtataa | atttcaaaaa | ataatcaata | caaaatgtt | tcacaatttc | tgtagctatc | 720 |
| caacggtata | tcattttctc | aattccgatt | agctattgaa | aaaccgtagt | gaaaaaacag | 780 |
| tagatataag | tactatagcg | ggaaattcaa | gagtttaagg | aagtacatgg | gaagttcatc | 840 |
| tgcatttatg | aaagaagttc | ataatcggtt | gtagattact | gcactacaac | cggttataga | 900 |
| atagctcggc | tatatatatc | tatatataag | tactagcagg | agcaaattaa | agtctgactt | 960 |
| tgatgacaat | tcgcacgccg | cattattgga | ctggtcacgg | ggaaatgaca | acgtacgcag | 1020 |
| ccaagagcca | agcctgtcag | ttacacgtac | agctcgccat | cgtctctcta | ggatagattc | 1080 |
| atcgtccgtg | tctgcataat | aaaatctccc | aaaggatatt | ttgtgtcctc | atactgcaat | 1140 |
| gtggcctctc | ttatctaatt | acctatccag | ctcacctccg | accctatatg | gtaggttcat | 1200 |
| ggactagaat | tggtccatgc | cagccacgga | tttcagtcga | cgcacaacaa | caaaaacgaa | 1260 |
| ggttgaattg | ggaggcagtt | gtgggccaca | aactagctag | tactgagccc | cttgcaacct | 1320 |
| cgcatgctta | caaacacaca | gaggacacta | taagatggga | tgcacatgca | ccacccagac | 1380 |
| aacaacactt | gcgagtcact | tgcattgcag | gaaaggtttc | t | | 1421 |

<210> SEQ ID NO 15
<211> LENGTH: 600
<212> TYPE: DNA
<213> ORGANISM: Lolium perenne

<400> SEQUENCE: 15

| | | | | | |
|---|---|---|---|---|---|
| aaaacagtat | gaactttcaa | aaaataatca | atacaaaaat | gtttcacaat | ttctgtagat | 60 |
| tactgcacta | caaccggtta | tagaataccc | cggctatata | tatatatatc | tatttataag | 120 |
| tactagcaag | agcaaattaa | agtctgactt | tgatgacaat | tcgcacgccg | cattattgga | 180 |
| ctggtcacgg | ggaaatgaca | acgcagccaa | gagccaagcg | tgtcggttac | acagctcgcc | 240 |
| gtcgtctctc | taggatagat | tcatcgtccg | tgtgaccgtg | tctgcataat | aaaatctccc | 300 |
| aaaggatatt | ttgtgtcctc | atactgcaat | gtggcctctc | ttatctaatt | acctatccag | 360 |
| ctcacctccg | accctatatg | gactagaatt | ggtccatgcc | agccacggat | ttcagtcgac | 420 |
| gcacaacaac | aaaaacgaag | gttgaattgg | gaggcagttg | tgggccacaa | actagctagt | 480 |

```
actgagcccc ttgcaacctc gcatgcttac aaacacacag aggacactat aagatgggat    540
gcacatgcac cacccagaca acaacacttg cgagtcactt gcattgcagg aaaggtttct    600
```

<210> SEQ ID NO 16
<211> LENGTH: 1501
<212> TYPE: DNA
<213> ORGANISM: Arabidopsis thaliana

<400> SEQUENCE: 16

```
accacttagg aggaaggtac tgaacattct gcgcgtttac ctgattctta tggttgaaac     60
tgaaattgta tttggcttga ccgtcgaaag tgaacactcc ccagtgcctc tcaaagttcc    120
cagcagataa gtttctctga tcttcgtcca agagactttc aatgtaggtt tcaacaggag    180
gacgcgggag agaggccgtc tttttctcca agtgaactat cagtcccttta aagaacgcct    240 cagcagtcag tgatgttgca ttttctgctc catctgtagg ccaaccgatc tttgacacaa    300
cgatatccac ctccgaaaac ccaattgtga acaatgcaga gacaagtgtg tcatagctta    360
gatcaaagct gtttctgtag gttttacgtc cgtctttgtg agcctttgct gtttctttaa    420
agaggctaaa gtcaagggag atgttcttgt tctggtgaaa gcttaggaaa ggagagattg    480
tcacaaaaaa aggagagtgg tgcttttgtga gaaggagag gagttcaatc atcgtcttgt    540
tgaggtcagc cctaaagtgt cctgaagaag gtcgaccaga ttcagaaaga aaggaatcaa    600
agcttgaggg gactacaacc ttcacttcat ttgccaagtt cgccttaact aaagcatttt    660
ggatattcat agctgcccca atcacaaaag gcttatactg attgccatag ctctggagaa    720
atggctcttc tccaactgct acatacctga aaatcaattc tttttcttaa tgataatttc    780
acaataagaa gattggcaat ttggcattga acaaatccg actcattcac attccataag    840
ttaaattcca gcttaaaaat cttaaatcta tatatatata actggataag cagaagagaa    900
ggagaaagaa gatactcgat tcgaactctg tttccaccgt tgaagtaacg agtgacattg    960
tcatgtaccc agctctctgc tacctttacg gatgcattca agctcttgag catcgaattt    1020
tggattccga tagtgacacc aatattagaa ccagagagag ctcggagaac ttttgggtcg    1080
gcatcgaaga gcttcacttt gacaatgccg tttgatttca gaagctctac aaccctttgaa    1140 ggcggaagag ggtgcgacgc ttctgtcccc caatttatgc caactgctct gacgttgtt    1200 cccgtcaagc tcaaccctgc cgtgacggcg aggaggagga gaaacagccg acgagccatc    1260
aaatccagtg aatctcgtac ttccacgata atgtcgggcc gagaaattca atgtttaaaa    1320
aaacaaaaca ctgcgtgccg tttcacgact cagcatctca ctgttattta gctatcaaaa    1380
cgacacggtg tttagaaatt gggcttgggc ttcacattcc ctaatcatca tcatctctga    1440
aatagaaatt atctgaaact tagagagaca gagagagaga aagctcaaat tcaatcatca    1500
a                                                                   1501
```

<210> SEQ ID NO 17
<211> LENGTH: 1501
<212> TYPE: DNA
<213> ORGANISM: Arabidopsis thaliana

<400> SEQUENCE: 17

```
tagtctgaaa taactatttc tttgatcatt aattgaagca tttctttggc ttaggatatt     60
tttgttaatg acatctgttc gaggagtgga ggaaaatgta aagtgccatg gactgttaca    120
cctgatatgg atcttctcgc tgcccaaaca atcatgaaca agcatgaact ttctcatgtt    180
```

```
gcagtcgttt caggcagcat tgatgctccc agaatacacc ctgttggggt cctggataga    240
gaatgtatca ctctaacacg caggtaaacc tgcatctatt tccctcggt ttaactgttt    300 gtcccaagat caccttttca tatggattgt ttttaatgaa cctaactgac taacctagtc    360
ttccatatga caagagtgtg tagagagtct gtgtaactat aacttgggct gccaggtttc    420
ccacattgga tgtagtagaa gttaaattag ttaaaaaaaa ttacttgcaa cttttttgttt   480 gctcatcaga ggaaaggagt gagtcgcaaa gtccagtttg ctagatttt aattttagag    540 ctttcatctg tattagagtt gataccgaaa atattgaccc agcaaataag gttcctcaat    600
tcatttgaaa cttttcggtg tagatgctgc attggagatg atactggttt tcttaacct    660 tttctcttgc ttgacctggc agggctctag caaccagaat gtacctccta aattcgctgt    720
atctgtaaat ggtcttgctt tgtaactctt ctgagctgac cagggtgatt tcaatttgtt    780
tcttctgtga ggctccgggc caattttgt tctttgtatt aagagatttg gggagaatga    840 gttgctggt gcagcgtgga tgttttttgt ctactccatc tgttggttta aatggtgaag    900
cccccatttc tcacttaagg tgctgagcaa tccaaaggga atcgaaacat ggagcgtggt    960
tctgagaaaa tcttcagaaa ttttcctgaa accaaagata tgtgctcagg tgattcgtta    1020
ccatttacac ttttttctta cagattgtta ctgtaccta cttagtattg tctattttgt    1080
aaagtgcttt ctgacttata tcatattgag aaagttttga ctacttaaag actaacagtg    1140
tcaacaattg taagggtttc cttgtccact attttgtata ttgaagaaca ttgaaatata    1200
ttggaatgcc cttatttctg tgtgtgtgt ctctctcggt gagccgcaag ggcatgttga    1260
catctaattg tatggatatt tttctctaag aaaattccta gagaaaacag tagtcaggcc    1320
attgtgttgg ttaaacaacc ctcctaaaac cttttaggta aagaagaagc aaccccgcat    1380
gggttgaatg acctacctaa cctatactta cctccatcat gatatagcta gtaccctctg    1440
aacatgcatg gatacacatg ctatataatc attcgggtgt gattccattt ataccggaaa    1500
a                                                                   1501

<210> SEQ ID NO 18
<211> LENGTH: 29
<212> TYPE: DNA
<213> ORGANISM: Artificial Sequence
<220> FEATURE:
<223> OTHER INFORMATION: Made in the lab

<400> SEQUENCE: 18
attaagtgac tcgggggatg taggggaac                                       29

<210> SEQ ID NO 19
<211> LENGTH: 29
<212> TYPE: DNA
<213> ORGANISM: Artificial Sequence
<220> FEATURE:
<223> OTHER INFORMATION: Made in the lab

<400> SEQUENCE: 19
gtcctcaccg tcagccattt gattaagtg                                       29

<210> SEQ ID NO 20
<211> LENGTH: 28
<212> TYPE: DNA
<213> ORGANISM: Artificial Sequence
<220> FEATURE:
<223> OTHER INFORMATION: Made in the lab

<400> SEQUENCE: 20
```

```
tggatctctc cttgggtacg aagaatgg                                          28

<210> SEQ ID NO 21
<211> LENGTH: 28
<212> TYPE: DNA
<213> ORGANISM: Artificial Sequence
<220> FEATURE:
<223> OTHER INFORMATION: Made in the lab

<400> SEQUENCE: 21
gctgatgatc tccctcatct tccctctc                                          28

<210> SEQ ID NO 22
<211> LENGTH: 28
<212> TYPE: DNA
<213> ORGANISM: Artificial Sequence
<220> FEATURE:
<223> OTHER INFORMATION: Made in the lab

<400> SEQUENCE: 22
gcgatcgaga gagaaacgga gactaagg                                          28

<210> SEQ ID NO 23
<211> LENGTH: 29
<212> TYPE: DNA
<213> ORGANISM: Artificial Sequence
<220> FEATURE:
<223> OTHER INFORMATION: Made in the lab

<400> SEQUENCE: 23
gcacagaccc catggtaatg atctacgag                                         29

<210> SEQ ID NO 24
<211> LENGTH: 27
<212> TYPE: DNA
<213> ORGANISM: Artificial Sequence
<220> FEATURE:
<223> OTHER INFORMATION: Made in the lab

<400> SEQUENCE: 24
atctctgcct gtgtctgctt ctcctgg                                           27

<210> SEQ ID NO 25
<211> LENGTH: 27
<212> TYPE: DNA
<213> ORGANISM: Artificial Sequence
<220> FEATURE:
<223> OTHER INFORMATION: Made in the lab

<400> SEQUENCE: 25
gtgttcttca gcgtcattgg gaggatc                                           27

<210> SEQ ID NO 26
<211> LENGTH: 28
<212> TYPE: DNA
<213> ORGANISM: Artificial Sequence
<220> FEATURE:
<223> OTHER INFORMATION: Made in the lab

<400> SEQUENCE: 26 gtttttttt ctaggggtgt tcgatcgc                                           28

<210> SEQ ID NO 27
<211> LENGTH: 28
<212> TYPE: DNA
```

```
<213> ORGANISM: Artificial Sequence
<220> FEATURE:
<223> OTHER INFORMATION: Made in the lab

<400> SEQUENCE: 27
aagcccacca tcgattgata ctcaaacc                                           28

<210> SEQ ID NO 28
<211> LENGTH: 28
<212> TYPE: DNA
<213> ORGANISM: Artificial Sequence
<220> FEATURE:
<223> OTHER INFORMATION: Made in the lab

<400> SEQUENCE: 28
gttttttttt ctagggtgt tcgatcgc                                            28

<210> SEQ ID NO 29
<211> LENGTH: 28
<212> TYPE: DNA
<213> ORGANISM: Artificial Sequence
<220> FEATURE:
<223> OTHER INFORMATION: Made in the lab

<400> SEQUENCE: 29
ctggatctct ccttacgtcc gctcgtac                                           28

<210> SEQ ID NO 30
<211> LENGTH: 30
<212> TYPE: DNA
<213> ORGANISM: Artificial Sequence
<220> FEATURE:
<223> OTHER INFORMATION: Made in the lab

<400> SEQUENCE: 30
ttactctctg tctggtggac tctctggagg                                         30

<210> SEQ ID NO 31
<211> LENGTH: 29
<212> TYPE: DNA
<213> ORGANISM: Artificial Sequence
<220> FEATURE:
<223> OTHER INFORMATION: Made in the lab

<400> SEQUENCE: 31
aagacgccgt ccattttact ctctgtctg                                          29

<210> SEQ ID NO 32
<211> LENGTH: 29
<212> TYPE: DNA
<213> ORGANISM: Artificial Sequence
<220> FEATURE:
<223> OTHER INFORMATION: Made in the lab

<400> SEQUENCE: 32
agaaaccttt cctgcaatgc aagtgactc                                          29

<210> SEQ ID NO 33
<211> LENGTH: 29
<212> TYPE: DNA
<213> ORGANISM: Artificial Sequence
<220> FEATURE:
<223> OTHER INFORMATION: Made in the lab

<400> SEQUENCE: 33
gccatggatt cagcagtgct atgctatag                                          29
```

<210> SEQ ID NO 34
<211> LENGTH: 20
<212> TYPE: DNA
<213> ORGANISM: Artificial Sequence
<220> FEATURE:
<223> OTHER INFORMATION: Made in the lab

<400> SEQUENCE: 34
ctgaacattc tgcgcgttta                                               20

<210> SEQ ID NO 35
<211> LENGTH: 20
<212> TYPE: DNA
<213> ORGANISM: Artificial Sequence
<220> FEATURE:
<223> OTHER INFORMATION: Made in the lab

<400> SEQUENCE: 35
tagggaatgt gaagcccaag                                               20

<210> SEQ ID NO 36
<211> LENGTH: 20
<212> TYPE: DNA
<213> ORGANISM: Artificial Sequence
<220> FEATURE:
<223> OTHER INFORMATION: Made in the lab

<400> SEQUENCE: 36
tcgaggagtg gaggaaaatg                                               20

<210> SEQ ID NO 37
<211> LENGTH: 20
<212> TYPE: DNA
<213> ORGANISM: Artificial Sequence
<220> FEATURE:
<223> OTHER INFORMATION: Made in the lab

<400> SEQUENCE: 37
aatggaatca cacccgaatg                                               20

<210> SEQ ID NO 38
<211> LENGTH: 292
<212> TYPE: DNA
<213> ORGANISM: Festuca arundinacea

<400> SEQUENCE: 38
ctggcacgac aggtttcccg actggaaagc gggcagtgag cgcaacgcaa ttaatgtgag    60
ttagctcact cattaggcac cccaggcttt acactttatg cttccggctc gtatgttgtg   120
tggaattgtg agcggataac aatttcacac aggaaacagc tatgaccatg attacgccaa   180
gctatttagg tgacactata gaatactcaa gctatgcatc caacgcgttg ggagctctcc   240
catatggtcg acctgcaggc ggccgcgaat tcactagtga ttggacactg ac           292

<210> SEQ ID NO 39
<211> LENGTH: 350
<212> TYPE: DNA
<213> ORGANISM: Lolium perenne

<400> SEQUENCE: 39
aaacaaaata cggacggtac gtaggacgac cagggagacg ttgaagtata cgatcgcgac    60
ggctcggcgg gcggccaagt ggatgagaag gaggccgtac cctagtaccg ggttgggaga   120

```
agaaggcggc tataagaatc ggcggtcggt cgtctacttg tgtcagccca tagttccgtg    180
cttaattgta accttgctgt gggtgggtgt gagtgagact gactcagtag tacgttggaa    240
gaaggagaag cagacgacga cgcggacggc ccctgttcct ccgccgtgat cgatcgctcg    300
aggagacgcg tgcgtgtcgg tgtgtgtgtg aagatcgctc gagggtttaa              350
```

<210> SEQ ID NO 40
<211> LENGTH: 468
<212> TYPE: DNA
<213> ORGANISM: Lolium perenne
<400> SEQUENCE: 40

```
ctgtacttcc agaatcacat cccgaacttc ccaccoctgg ccacctgctc cttcccggat     60
acaaatggga agccaattcg atgcaccagt tatggccagg ctctgtacag ccttccgggt    120
agtaaactga ttccccaaga agcggcagaa tggttcagag ttttctacca aggtctggac    180
aaccctctct tcatcccctta cagggagtct gaaaattttg aaaacccagt ctccttcagg    240
ttagacagct ttgccgatga tgccgacact cggcagttat attccatcat gatccgccct    300
tgcttcctcc caggttggca tgatcacctc taacatgatc atcaagcctg gttatgagtc    360
ttatcagccg gtcgtagtgg cccggcaact tggtcttggg caggtgcctc ctcatttctt    420
ccttcaccac ctaacagaga gcagagcaga atctcctacc cagaccac                468
```

<210> SEQ ID NO 41
<211> LENGTH: 438
<212> TYPE: DNA
<213> ORGANISM: Lolium perenne
<400> SEQUENCE: 41

```
aaactctctt ccaaaacaga gtgcacaagc tggggtgttt atcttaggat ccacatgaaa     60
accaaaagcc ctgtgacaga taaagagcac acggcttttc tgaatttctg gttggaacat    120
ttcatattct gtggttcttc gcttgctcca accaagaact acctttcctt ggcctatgaa    180
cttgccagag gcactcagct tggcatcggg aaactgttcc ttggagaagt ctatcggtat    240
ctccagctga tgtctgtcaa cctatttcct caaaagacag tcaaaacagg tggtccctgg    300
tggtttattc agttatgggc tcagctgtac ttccagaatc acatcccgaa cttcccaccc    360
ctggccacct gctccttccc ggatacaaat gggaagccaa ttcgatgcac cagttatggc    420
caggctctgt acagcctt                                                  438
```

<210> SEQ ID NO 42
<211> LENGTH: 1736
<212> TYPE: DNA
<213> ORGANISM: Lolium perenne
<400> SEQUENCE: 42

```
aaaaccataa gggattcata tagagcatcg ttagtactag tacagttctt gtctatcaag     60
ttttactagt gcagtataat tttgtacaag tgattgaata tcgtcagtag attcagtcta    120
atcgtgccac ttggaatata acacatacaa ttatttaaca tagtgtcaaa tgtatgagaa    180
acctaaagac gatagtcaag agtagtatct cacaaatact ggagtgccta ctcctgcagg    240
tggacatagt ggcgccacca atggttcatt ggcttggggt ctttgctaca aacgtgaatt    300
gagcccaagc cagagctatt gtgacgacag caacgaattg taccgttgtg ctgaaggagt    360
cgagtactat ggtcgaggcg ccccttcctgt ttactggtca ggctgatatg ttatttctcc    420
cagttgttgt ttattatgaa ctagctgggc caagctattg attttgtatc tacttgtaaa    480
```

```
cgatctgcag gaactacaac tacggtatcg tgggtaaggg cataaagcag gatctgttga    540
accacccaga gttattggaa cagaatgcga ccctagcatt tgaagcggca atctggaggt    600
ggatgactcc aatgaagaga aggcagccat cagcgcatga tgtctttgtt ggcaactgga    660
aaccaaccaa gaaagacacc ttgtccaaga ggtatcctgg ctttggtgct accatgaaca    720
tcttgtatgg cgatctcata tgtggtaaag ggaccattga ccgtatgaat gtcattgtat    780
cccactatca acattatctt aatttgatgg gagttggtga tcagcagtct ggagataact    840
tggattgtgc cgaccaagtt ccattcaatc cgtcatcaaa gaatctagac tcatgagcaa    900
gttgcttgtc agatctatgt atatttcctt taaggcacat ccatcttgct tcccaaacta    960
tagtaatctt gtatgcgaat ctataaggta tattatttag tagctctgag gactactatt   1020
gcgtcttgga agtttgtgat ctacttatgt aatctcgtaa tcttctctca ctatgtgatc   1080
ttgccctgca tattacagga gaaaaattac attctaacat gtgacgcctt tgttactgtc   1140
gtggatatgt tgtcagcaac acatctgtca tcgttctctt gttatgtgga catgattcat   1200
gtaacaatga taacttctaa tcgaactgtg tggagggatc ttgtcttact ttgttttctg   1260
aattccttca gctacacagt ttttcttca aattttctct attttggatt aatatttga   1320 tgttaatttt gtaaggcaca aacagtgaaa ccagactttg ttgtagaagt gtaaacatac   1380
atggaagcat atgtgtggaa aatatccaac atacagacaa aaactcaaaa tctattgtga   1440
atttactgag ataatatgcg tagggagttc agtggcatat tcttgcaaaa ctatagatgg   1500
gttgatattt accactgaaa cagcttatcc aagtgccgga aggggaccgt cctctggaca   1560
ccacacatgg gcctggatag ccaggtacag atagactgac tagagagttc tgtcttttc   1620 ctcttccatt tcagggcagt agaactggca ttcaaacaag gcaagcagga aggggatgaa   1680
gctcaccaat atcccccatc ttgcctcctc ctcctccagc ttcttcttct ccaact       1736
```

<210> SEQ ID NO 43
<211> LENGTH: 629
<212> TYPE: DNA
<213> ORGANISM: Lolium perenne

<400> SEQUENCE: 43

```
cctataaaga agggcggcta tctggcccat gggagtacaa gctccccggg tgagatgtaa     60 atttccaaa taatggttag aaaaatatga aaacatattt gttgtgtcca tgtctgatgt    120
gcatgcaaag ttttattaac aaaaaacaag ttttgtgccc agcaaaaaaa cccagtgctc    180
tatagtgaaa attctctaaa tcgaaacact tattgaacac acaacctcaa ccaccttgtc    240
taattatttc aagaatccag aaaagaaaat tgacatggag ataggcaatt tttcattgaa    300
aacgaacaaa gctatccacg ccactcagaa acgtagctat ggtgggctcc ttttcttata    360
tagaaatggc catgaaatct tcgcatttcg aaaatcgttc cttttcatag agtctggcct    420
gggtgcaact ttgaatttcc cgcgtgtata tacatgcata tagccatagg acggagaacc    480
gattgtgcat caatatatgg cccactccca attttgtttc tattatcgtc cactcagcta    540
tatatcagct ccctcgctca ctgctgaaga gcacacgtac aggcacccat ccaccggagt    600
atactagcca ggaaattcct gcaactcga                                       629
```

<210> SEQ ID NO 44
<211> LENGTH: 1201
<212> TYPE: DNA
<213> ORGANISM: Lolium perenne

<400> SEQUENCE: 44

```
ccttatgtat aaaaccatca tgtgatgtat gattagtatt agaagtacaa tggttgtaca    60
tataagctgt taaagaatta tggttttttct aattctcagc taaccgggat ttagactagt   120
gctcggtcaa ctccaatact atttgattat tgtttcaaga ctcgtgccca ttgtttcaag   180
attcgtgctt atgggctcac ccagctttat ctcttctctt cccttctctt gggcacggcc   240
caacagaaag atgagagaac ccaccgccca cctcgtcgga attgaagccg acgacgtcga   300
gcctggacca agctagagga aaggctgact ctggcgagga agaaacttag gttggggag    360
agggtacgtg atcactggag cgaaccggag aaggtggggg tttagaggga tggccagggg   420
tggcactgca tgcatggacc gacgagaagc aagagcttgg ggcaggacga ggcatcacga   480
tagtgcgccg cccacgggtg ggatggcggc gatcaagtcc atcgtcgatg ctcgccgaag   540
gaggaggaca acaaggcgat aggagggacg atggcgacgt cagtccaatg ggaatttggt   600
taattctccg tcgactgcgc cctaaacgga cctttagaat caatatgatg catgattaaa   660
tatttatacc gtcatactgg aaatttgact atgtgagcac gtacgggaaa atgaacctca   720
gaaaatcatt tttatgttca tcacttcata ccaacgttgg taagagcaag ttagattact   780
gtggatgaaa aacgcacagc agtgcatctg cctgcttaag agaaacgacc aagtccccct   840
cacgaaaagg ccatccgcaa cgctcctccg cctcttcctc gccgtgcacc aaccccctgc   900
cacgaaggtg ccaacgcgct catctacgta gccaccaccc ggtccgtcat ggctcatggc   960
cactggagct ccacccacca atgaccaatc cagacatcca gtggtcaacc tcgccttcca  1020
ggtccatacc aacccacacc ccgacacccg cacctaccct gctctgccta tttaatccct  1080
gccctgcctc cattcccctc caagaagagc ctcacctgct tcctctgcaa ctcgagctcc  1140
tcttcagtct tactcgctct agtagttctt tgcaacgatc aacactgtca gaatccagat  1200
a                                                                 1201
```

<210> SEQ ID NO 45
<211> LENGTH: 1566
<212> TYPE: DNA
<213> ORGANISM: Lolium perenne

<400> SEQUENCE: 45

```
ctgcacaggc gaccaagacg cgaacaaaag cgggtcctca acttgccttg aaatgaacct    60
tcagatgtaa gtggtgtctg ccaggactcc ttagtcctta ttgattgact gacccatttt   120
aaacataact gatcgtgaaa cacgagagac tcttggcagc aaagggattc atatgcagga   180
aaagagccag caagaaaggg tcgtactgca ataggaaata ggaaatactc acggtcacga   240
tcgagctgaa ctcccacatg gccatgtgtg ctagctagct taattgaata tagaatacgt   300
gtggtgaaca actaaaccat ggtgaacaac taaccatcat ctgatattat aaagcttggc   360
caaggcctta tgtataaaac catcatgtga tgtatgatta gtattagaag tacaatggtt   420
gtacatataa gctgttaaag aattatggtt tttctaattc tcagctaacc gggatttaga   480
ctagtgctcg gtcaactcca atactatttg attattgttt caagactcgt gcccattgtt   540
tcaagattcg tgcttatggg ctcacccagc tttatctctt ctcttccctt ctcttgggca   600
cggcccaaca gaaagatgag agaacccacc gccacctcg tcggaattga agccgacgac   660
gtcgagcctg gaccaagcta gaggaaaggc tgactctggc gaggaagaaa cttaggttgg   720
gggagagggt acgtgatcac tggagcgaac cggagaaggt gggggtttag agggatggcc   780
aggggtggca ctgcatgcat ggaccgacga gaagcaagag cttgggcag gacgaggcat   840
```

```
cacgatagtg cgccgcccac gggtgggatg gcggcgatca agtccatcgt cgatgctcgc      900
cgaaggagga ggacaacaag gcgataggag ggacgatggc gacgtcagtc caatgggaat      960
ttggttaatt ctccgtcgac tgcgccctaa acggaccttt agaatcaata tgatgcatga     1020
ttaaatattt ataccgtcat actggaaatt tgactatgtg agcacgtacg ggaaaatgaa     1080
cctcagaaaa tcattttat gttcatcact tcataccaac gttggtaaga gcaagttaga      1140
ttactgtgga tgaaaaacgc acagcagtgc atctgcctgc ttaagagaaa cgaccaagcc     1200
cccctcacga aaaggccatc cgcaacgctc ctccgcctct cctcgccgt gcaccaaccc      1260 cctgccacga aggtgccaac gcgctcatct acgtagccac cacccggtcc gtcatggctc     1320
atggccactg gagctccacc caccaatgac caatccagac atccagtggt caacctcgcc     1380
ttccaggtcc ataccaaccc acaccccgac acccgcacct accctgctct gcctatttaa     1440
tccctgccct gcctccattc ccctccaaga agagcctcac ctgcttcctc tgcaactcga     1500
gctcctcttc agtcttactc gctctagtag ttctttgcaa cgatcaacac tgtcagaatc     1560
cagata                                                              1566
```

<210> SEQ ID NO 46
<211> LENGTH: 1180
<212> TYPE: DNA
<213> ORGANISM: Lolium perenne

<400> SEQUENCE: 46

```
ctgaagtcgt tgccttggcg cccagagtcc acacgaggtg acatattgat ggccacacca       60
ccaccttcgt cgacgtcatg cgaccaccta aggcaccaac aaggagaagg ggagaggggt      120
ggcagtctac gatttccttg agtcacctct gagagagaga tgcaatggag ggtggttgca      180
aaattagtgc tgggtgtcca agaaacccct aaatcgcctt tgtatgtctt ggggctgtac      240
cggctcgcac atgcgataga atttattttg ttcaatagag acagaccatt tctaaagaaa      300
atattacttc ctctatccaa attaaatttc atgaactatt ctaaattcac atgtatctat      360
acatactccc tccaccacaa ataagtggac atctagcccct aaactttgtc cataaaagag     420
tgtactccta tcttcccaat gcactttaat tgcttctctc tcatcgcata gaaatcaaac      480
ctaataatat tgagcatata ttttctttat tttctacaag cacttagctc attacagcta      540
aaataattaa agaggagaga tatatctttc actgcatttt tcacttcact ttataattta      600
tcttgaaaaa cctgcatgta tacttatttg tgaacggagg gagtatatgt tacaagtaat      660
taatttggga cggtgggagt ataaaaggag attaaatagg gaaagaaacc aaagaagtgg      720
ctagaggcag tttttatata atatattaaa aataaaaagg agtgtggcct gcgtttggtt      780
cgaccgtacg aggtgcagag tgcagacaca tcacacatgg cgatggagta aacctgcatt      840
gcagttaatc agcacagggg cacagcagca gcagtatata ctgccatcga ttaattgttt      900
taatccgtat tatcttgttg ctaacagcgc taacacacga taccggggcc aattagcagg      960
gagagactga gcgggtgggg gcacggtgag tgtctccgcc aatcagcgct cgacagcatc     1020
ctgccccccc ccaaaccaca ccccaatta caatccatcc tcttctcctc catcttccct      1080
ctttaaagct gcatcccttg cctggcctcg ccgccgcggt gactcctccg atccactcca     1140
ctccactccg gccaattcct tggtagacag ccggcagcta                           1180
```

<210> SEQ ID NO 47
<211> LENGTH: 1230
<212> TYPE: DNA

<213> ORGANISM: Lolium perenne

<400> SEQUENCE: 47

```
tattggtttt catagacatg gacatagttt cacttattaa cgaggtcata ttattaagga    60
gaataatatg atggacttga cctaatcaaa gcatagcaat tgaccacgtt acatggatct   120
aattgcgaaa cttttccgtt atcatctata ctattccttt gaccataaga ttatacaact   180
ctcgagtatt ggaagaattc ataacttgtt gcaaacgtca cttcgttatt gggtgatcat   240
aaagctatct ctcatgcatt atataagata cttgttgtgt tgtatgttat caagagtggg   300
atttttcaat ccaagtaacg gaaagatatt ctctggccct cttggtaata cgcactcaat   360
ttcttgcaat cccgtgacta ggtcacatga gggtgcgcta ttatgatgag aaaagagtac   420
ttaccagtaa cgagataagg acaatgtatg aaaggtatca acgatcaaat ctcggataac   480
taagataccg caggacatgg gaattatata tgaatgacat aagtggttca ctagataaga   540
tgattgttga atatgtggga gttaatatgg atctctagat ccctctatta accattagct   600
atgtacatag tcatgtccgc ataatcgcga atctgtaggg ttaaacactt aagattcgac   660
gttgctagga tagagagatg tcaagtgcag tattttcggt gtcccgaatg gattcgggga   720
tatcacggtt ggactcggaa gggcaaaaac cccataggaa catatatggg aagtatcgga   780
atggttccgg aaagtcggtt gtaccggaaa gttccaaggg gggaacccac ctagcctagg   840
gccgggtggg cccgacccac gtgccaagtg ggctataatc tgcaaaataa gggccgaagt   900
gtaacaaaaa aaatgcaggt caaattgttg gctcaaactc atatacgtag actcttttttc   960
gttttgatct cacttgggaa atcaaacggc tacacaaaat cttagagcat ctacgtaccc  1020
caagacagag gtgaaaggga aggagcaacc ccaagacaga tagacgtacc gtacgtgcat  1080
gtgtagggta gcaaccacac taatttacat ccatctactc atccatccat cttagcatat  1140
cataaagaga gggaaagtag cactgctagt cctcggcttg gtagtgctat ctgagtaggg  1200
agaaggagca gggagaagaa gagagagatc                                   1230
```

<210> SEQ ID NO 48
<211> LENGTH: 343
<212> TYPE: DNA
<213> ORGANISM: Festuca arundinacea

<400> SEQUENCE: 48

```
aaataaagag cgccctttgt aaaaaaaaac attttgcgtg tacgcgggtg ttcatgcctg    60
gccggttgag acctgccagt agtggtggtg tctagatatg gtagcagtac cctaattaag   120
ctagggcgag tgcgagagcc gagatccaat ccgatctgta ccccacgaaa gggaaaggaa   180
aaagattctt gccttgcccc gccccgcctc cctctcctcg gcaaagctat acaacaccac   240
caccacagcc acagagccac agccagtcgc ccggcacaac tgcagcctga ccagggccct   300
caaagaaaac aaatctagga caatcaagcc gctgctagct agg                     343
```

<210> SEQ ID NO 49
<211> LENGTH: 29
<212> TYPE: DNA
<213> ORGANISM: Artificial Sequence
<220> FEATURE:
<223> OTHER INFORMATION: Made in the lab

<400> SEQUENCE: 49

```
ttcacctcct gcttcatctt cctctcaag                                      29
```

<210> SEQ ID NO 50
<211> LENGTH: 29
<212> TYPE: DNA
<213> ORGANISM: Artificial Sequence
<220> FEATURE:
<223> OTHER INFORMATION: Made in the lab

<400> SEQUENCE: 50
agctagattt cccctgctgc tcttttctg                              29

<210> SEQ ID NO 51
<211> LENGTH: 28
<212> TYPE: DNA
<213> ORGANISM: Artificial Sequence
<220> FEATURE:
<223> OTHER INFORMATION: Made in the lab

<400> SEQUENCE: 51
taaaccctcg agcgatcttc acacacac                               28

<210> SEQ ID NO 52
<211> LENGTH: 29
<212> TYPE: DNA
<213> ORGANISM: Artificial Sequence
<220> FEATURE:
<223> OTHER INFORMATION: Made in the lab

<400> SEQUENCE: 52
gtcgtctgct tctccttctt ccaacgtac                              29

<210> SEQ ID NO 53
<211> LENGTH: 28
<212> TYPE: DNA
<213> ORGANISM: Artificial Sequence
<220> FEATURE:
<223> OTHER INFORMATION: Made in the lab

<400> SEQUENCE: 53
cagagcagga gttgaagggg agagagag                               28

<210> SEQ ID NO 54
<211> LENGTH: 28
<212> TYPE: DNA
<213> ORGANISM: Artificial Sequence
<220> FEATURE:
<223> OTHER INFORMATION: Made in the lab

<400> SEQUENCE: 54
gtggtctggg taggagattc tgctctgc                               28

<210> SEQ ID NO 55
<211> LENGTH: 29
<212> TYPE: DNA
<213> ORGANISM: Artificial Sequence
<220> FEATURE:
<223> OTHER INFORMATION: Made in the lab

<400> SEQUENCE: 55
ataacagtgg gtatttgcag gacctgagg                              29

<210> SEQ ID NO 56
<211> LENGTH: 29
<212> TYPE: DNA
<213> ORGANISM: Artificial Sequence
<220> FEATURE:
<223> OTHER INFORMATION: Made in the lab

```
<400> SEQUENCE: 56
agttggagaa gaagaagctg gaggaggag                                29

<210> SEQ ID NO 57
<211> LENGTH: 27
<212> TYPE: DNA
<213> ORGANISM: Artificial Sequence
<220> FEATURE:
<223> OTHER INFORMATION: Made in the lab

<400> SEQUENCE: 57
aactcgaggt cgagttgcag gaatttc                                  27

<210> SEQ ID NO 58
<211> LENGTH: 29
<212> TYPE: DNA
<213> ORGANISM: Artificial Sequence
<220> FEATURE:
<223> OTHER INFORMATION: Made in the lab

<400> SEQUENCE: 58
tcgagttgca ggaatttcct ggctagtat                                29

<210> SEQ ID NO 59
<211> LENGTH: 29
<212> TYPE: DNA
<213> ORGANISM: Artificial Sequence
<220> FEATURE:
<223> OTHER INFORMATION: Made in the lab

<400> SEQUENCE: 59
ctcggactcc atggatattt gcaaagaac                                29

<210> SEQ ID NO 60
<211> LENGTH: 30
<212> TYPE: DNA
<213> ORGANISM: Artificial Sequence
<220> FEATURE:
<223> OTHER INFORMATION: Made in the lab

<400> SEQUENCE: 60
tatctggatt ctgacagtgt tgatcgttgc                               30

<210> SEQ ID NO 61
<211> LENGTH: 29
<212> TYPE: DNA
<213> ORGANISM: Artificial Sequence
<220> FEATURE:
<223> OTHER INFORMATION: Made in the lab

<400> SEQUENCE: 61
atcttgttct ctatccgctt cagctgcac                                29

<210> SEQ ID NO 62
<211> LENGTH: 27
<212> TYPE: DNA
<213> ORGANISM: Artificial Sequence
<220> FEATURE:
<223> OTHER INFORMATION: Made in the lab

<400> SEQUENCE: 62
tagctgccgg ctgtctacca aggaatt                                  27

<210> SEQ ID NO 63
<211> LENGTH: 30
```

```
<212> TYPE: DNA
<213> ORGANISM: Artificial Sequence
<220> FEATURE:
<223> OTHER INFORMATION: Made in the lab

<400> SEQUENCE: 63 gcccttttcgc ctgacctagt ctctctctag                                    30

<210> SEQ ID NO 64
<211> LENGTH: 31
<212> TYPE: DNA
<213> ORGANISM: Artificial Sequence
<220> FEATURE:
<223> OTHER INFORMATION: Made in the lab

<400> SEQUENCE: 64
gatctctctc ttcttctccc tgctccttct c                                   31

<210> SEQ ID NO 65
<211> LENGTH: 29
<212> TYPE: DNA
<213> ORGANISM: Artificial Sequence
<220> FEATURE:
<223> OTHER INFORMATION: Made in the lab

<400> SEQUENCE: 65
gatgactagg ttggcatgag atttggctc                                      29

<210> SEQ ID NO 66
<211> LENGTH: 29
<212> TYPE: DNA
<213> ORGANISM: Artificial Sequence
<220> FEATURE:
<223> OTHER INFORMATION: Made in the lab

<400> SEQUENCE: 66
cctagctagc agcggcttga ttgtcctag                                      29

<210> SEQ ID NO 67
<211> LENGTH: 10
<212> TYPE: DNA
<213> ORGANISM: Artificial sequence
<220> FEATURE:
<223> OTHER INFORMATION: Made in the lab

<400> SEQUENCE: 67
caagaggatc                                                           10

<210> SEQ ID NO 68
<211> LENGTH: 10
<212> TYPE: DNA
<213> ORGANISM: Artificial sequence
<220> FEATURE:
<223> OTHER INFORMATION: Made in the lab

<400> SEQUENCE: 68
caaaaagatc                                                           10

<210> SEQ ID NO 69
<211> LENGTH: 10
<212> TYPE: DNA
<213> ORGANISM: Artificial sequence
<220> FEATURE:
<223> OTHER INFORMATION: Made in the lab

<400> SEQUENCE: 69
```

```
caacctaatc                                                          10

<210> SEQ ID NO 70
<211> LENGTH: 10
<212> TYPE: DNA
<213> ORGANISM: Artificial sequence
<220> FEATURE:
<223> OTHER INFORMATION: Made in the lab

<400> SEQUENCE: 70
caagagcatc                                                          10

<210> SEQ ID NO 71
<211> LENGTH: 10
<212> TYPE: DNA
<213> ORGANISM: Artificial sequence
<220> FEATURE:
<223> OTHER INFORMATION: Made in the lab

<400> SEQUENCE: 71
caaaatcatc                                                          10

<210> SEQ ID NO 72
<211> LENGTH: 10
<212> TYPE: DNA
<213> ORGANISM: Artificial sequence
<220> FEATURE:
<223> OTHER INFORMATION: Made in the lab

<400> SEQUENCE: 72
caactaaatc                                                          10

<210> SEQ ID NO 73
<211> LENGTH: 11
<212> TYPE: DNA
<213> ORGANISM: Artificial sequence
<220> FEATURE:
<223> OTHER INFORMATION: Made in the lab

<400> SEQUENCE: 73
cctcacctac c                                                        11
```